US009578982B2

(12) United States Patent
Rampersad

(10) Patent No.: US 9,578,982 B2
(45) Date of Patent: Feb. 28, 2017

(54) DISPOSABLE FINGER TONGS FOR HANDLING A FOOD PRODUCT

(71) Applicant: Kenrick Rampersad, Brentwood, NY (US)

(72) Inventor: Kenrick Rampersad, Brentwood, NY (US)

(*) Notice: Subject to any disclaimer, the term of this patent is extended or adjusted under 35 U.S.C. 154(b) by 0 days.

(21) Appl. No.: 14/706,426

(22) Filed: May 7, 2015

(65) Prior Publication Data

US 2016/0157647 A1 Jun. 9, 2016

Related U.S. Application Data

(63) Continuation-in-part of application No. 13/939,070, filed on Jul. 10, 2013, now Pat. No. 9,033,383.

(60) Provisional application No. 61/848,579, filed on Jan. 7, 2013, provisional application No. 61/796,556, filed on Nov. 13, 2012, provisional application No. 61/741,657, filed on Jul. 25, 2012, provisional application No. 61/741,052, filed on Jul. 11, 2012.

(51) Int. Cl.
| | |
|---|---|
| *B65G 7/12* | (2006.01) |
| *A47G 21/10* | (2006.01) |
| *A41D 13/08* | (2006.01) |
| *A47J 43/28* | (2006.01) |
| *A61F 13/10* | (2006.01) |
| *A47G 21/00* | (2006.01) |

(52) U.S. Cl.
CPC ........... *A47G 21/10* (2013.01); *A41D 13/087* (2013.01); *A47G 21/001* (2013.01); *A47J 43/283* (2013.01); *A61F 13/105* (2013.01)

(58) Field of Classification Search
CPC ..... A61F 13/104; A61F 13/105; A47G 21/10; A47G 21/001; A47J 43/283; A41D 13/087
USPC ......... 294/25, 1.3, 16, 99.1–99.2, 902, 55.5, 294/176, 106; 2/20–21, 17, 160, 163, 2/159; 223/111
See application file for complete search history.

(56) References Cited

U.S. PATENT DOCUMENTS 1,235,199 A * 7/1917 Gavin .................. A41D 13/087
                                                               15/246
4,476,588 A * 10/1984 Long .................. A41D 19/0068
                                                               2/159

(Continued)

FOREIGN PATENT DOCUMENTS

WO PCTUS2016031045 A 9/2016

*Primary Examiner* — Stephen Vu
(74) *Attorney, Agent, or Firm* — Alfred M Walker; John F Vodopia

(57) ABSTRACT

A disposal food handling finger tongs have finger pockets for grasping food. The pockets are connected by at least one connecting tab. At least one functional finger/thumb accommodation area is presented and at least one finger/thumb stability is optionally provided. The disposable tongs provide a triple protection to the user by providing soft irregular peripheral edges help prevent paper cuts. Also the central connecting tab between the two jaw pockets can be torn to separate the tongs into two tongs, so that the two food contact sides of the respective pockets can be folded against each other. Third, if both the front and back of pockets are messy, the clean central tab can be torn, and folded over the back and/or front of the messy pockets, thereby keeping the hands, fingers and/or thumb of the user clean during disposal.

29 Claims, 34 Drawing Sheets

(56) References Cited

U.S. PATENT DOCUMENTS

| | | | |
|---|---|---|---|
| 4,677,697 A * | 7/1987 | Hayes | A41D 19/0068 2/159 |
| 5,280,661 A * | 1/1994 | Brown | A47L 13/18 15/214 |
| 6,425,136 B1 * | 7/2002 | Schlamp | A41D 19/0068 2/159 |
| 2002/0043810 A1 * | 4/2002 | Dooley | A01K 23/005 294/1.3 |
| 2006/0108240 A1 * | 5/2006 | MacKinnon | A45C 13/02 206/223 |
| 2007/0118947 A1 | 5/2007 | Lorenzo | |
| 2008/0000011 A1 | 1/2008 | Ayala | |
| 2014/0109284 A1 | 4/2014 | Lefrancois, Jr. | |

* cited by examiner

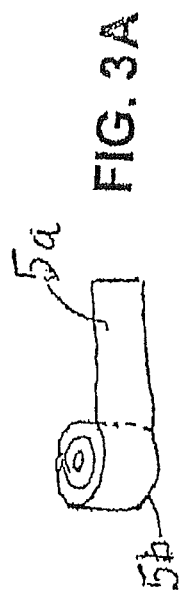
FIG. 2 SIDE VIEW
FIG. 3A
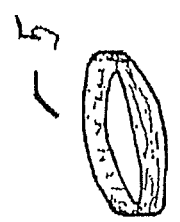
FIG. 3
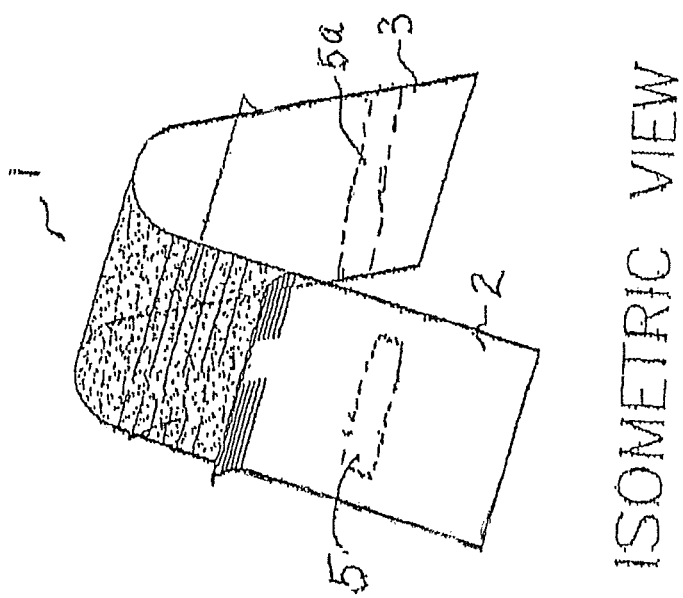
FIG. 1 ISOMETRIC VIEW

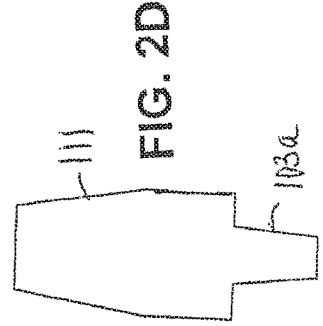
FIG. 2B
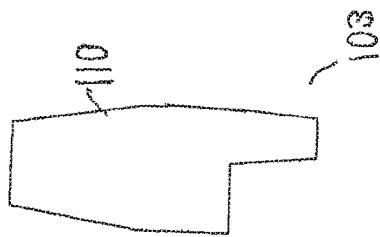
FIG. 2A
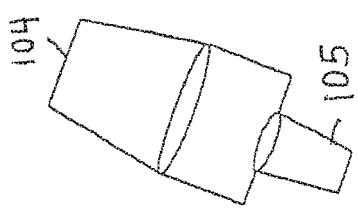
FIG. 2D
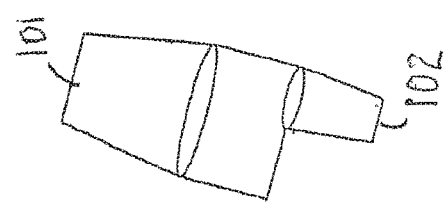
FIG. 2C
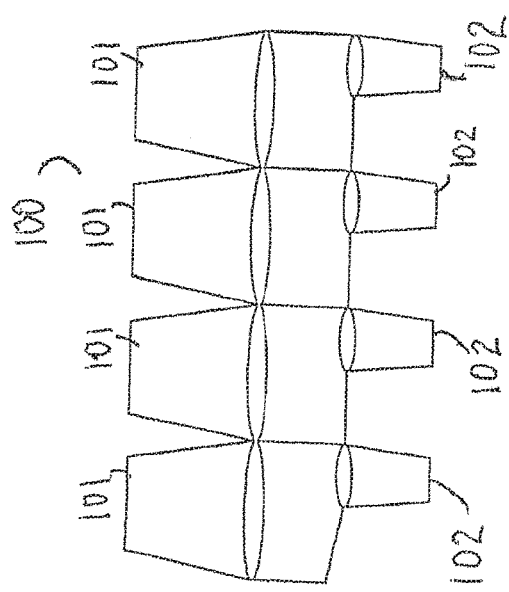
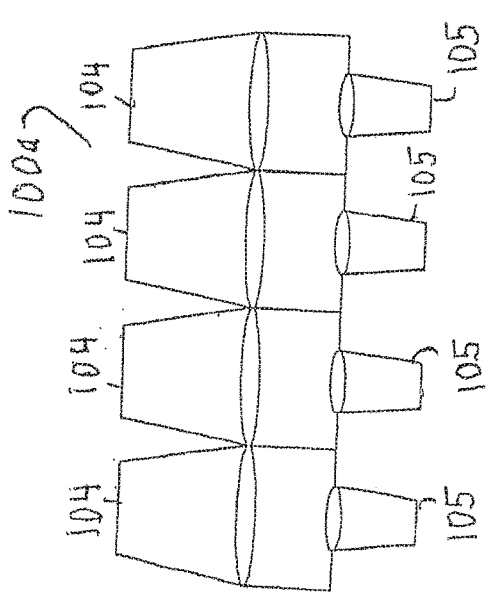

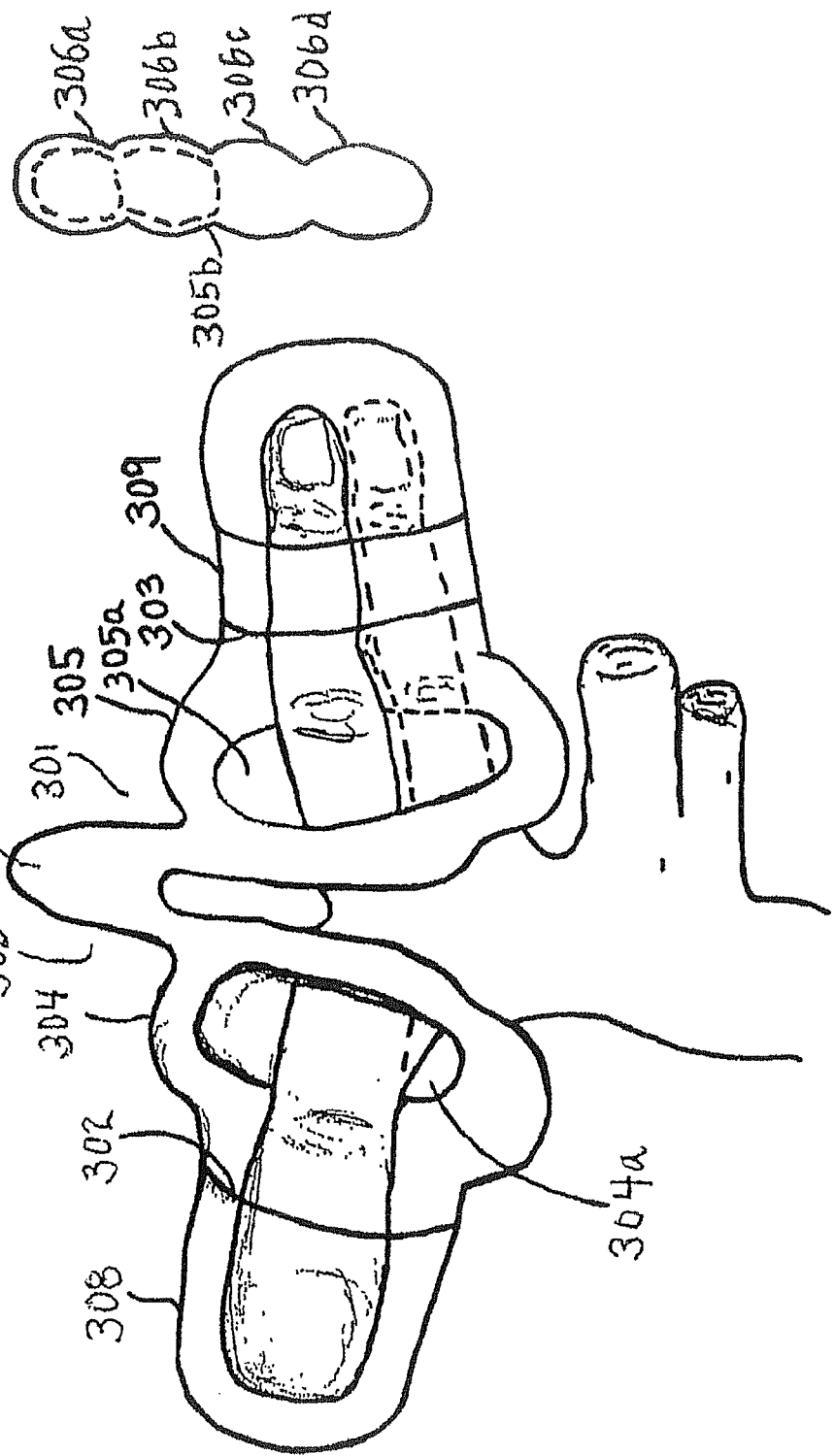

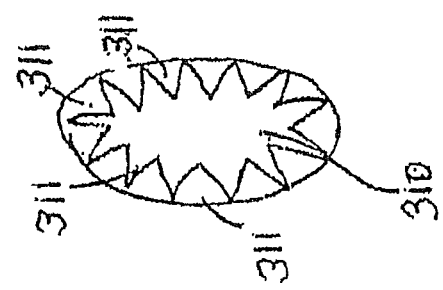
FIG. 5D
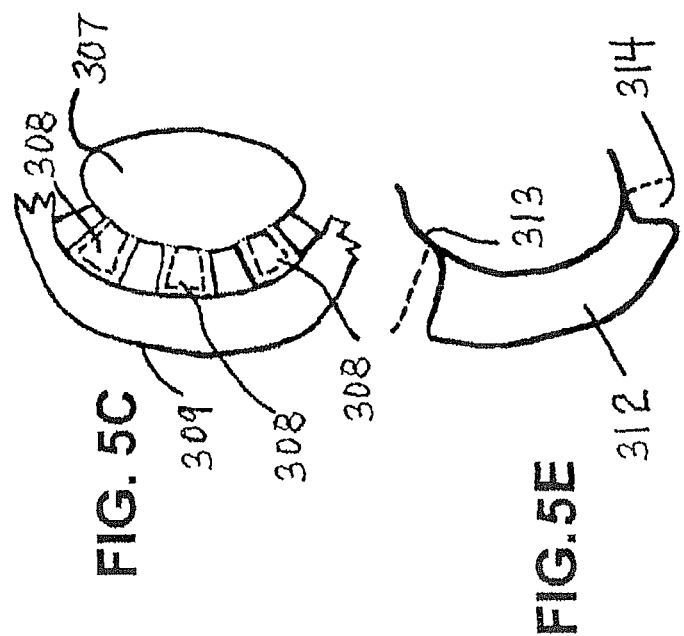
FIG. 5C
FIG. 5E

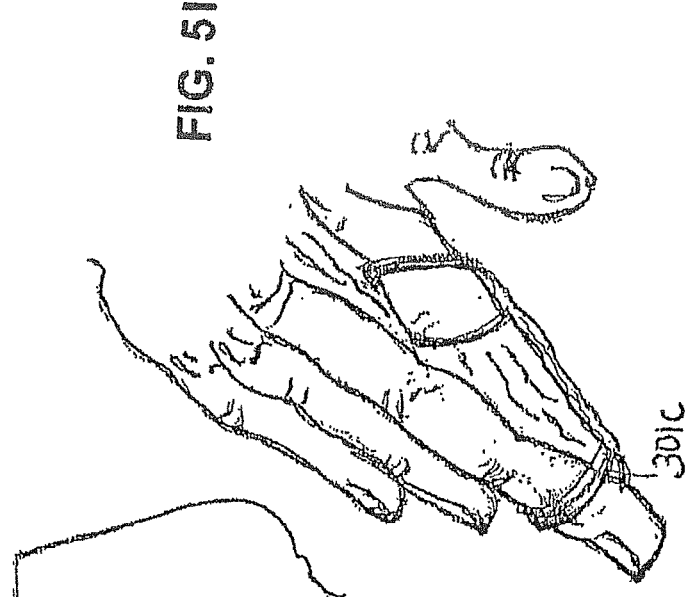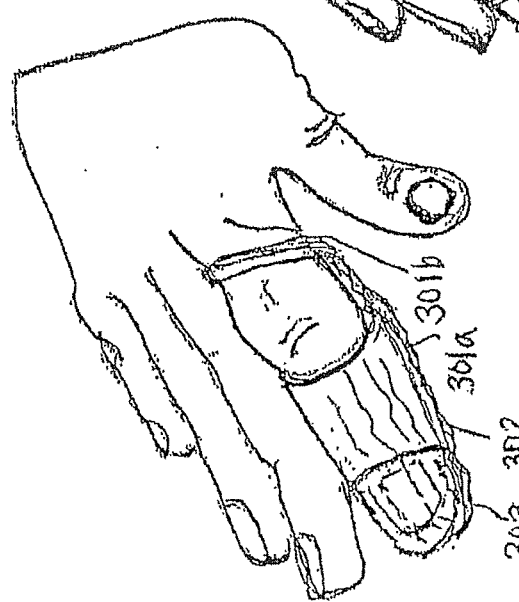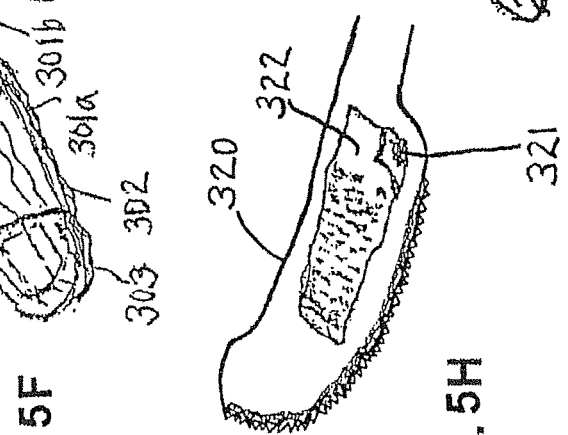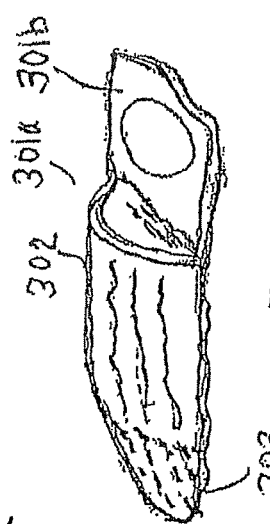

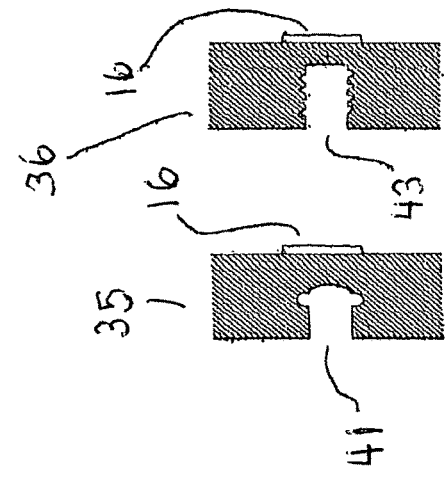
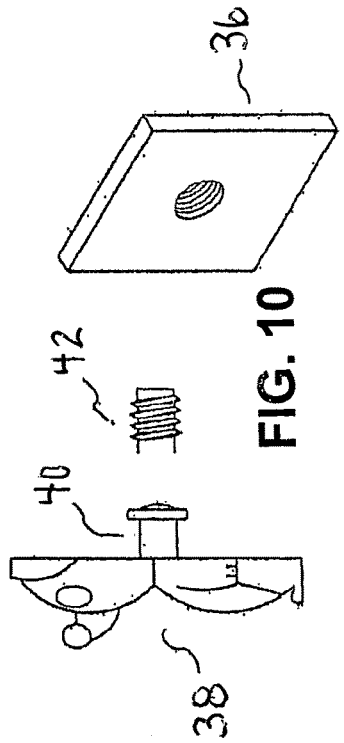
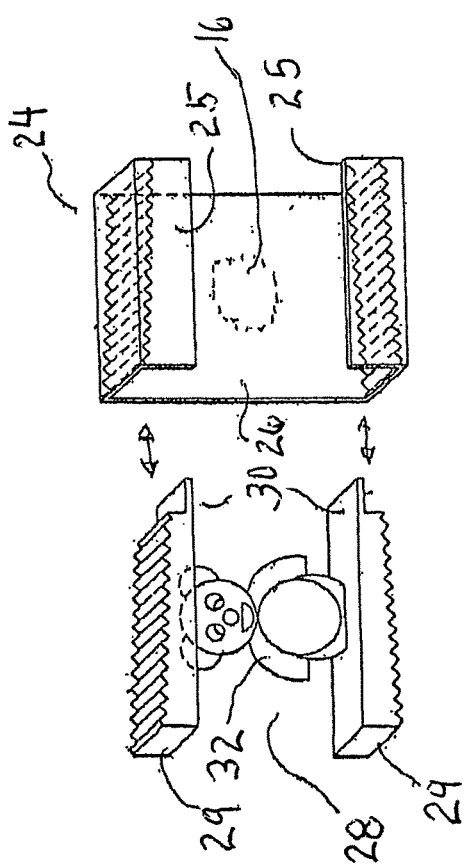
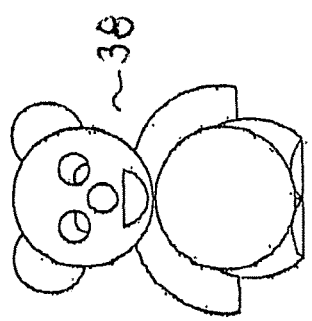

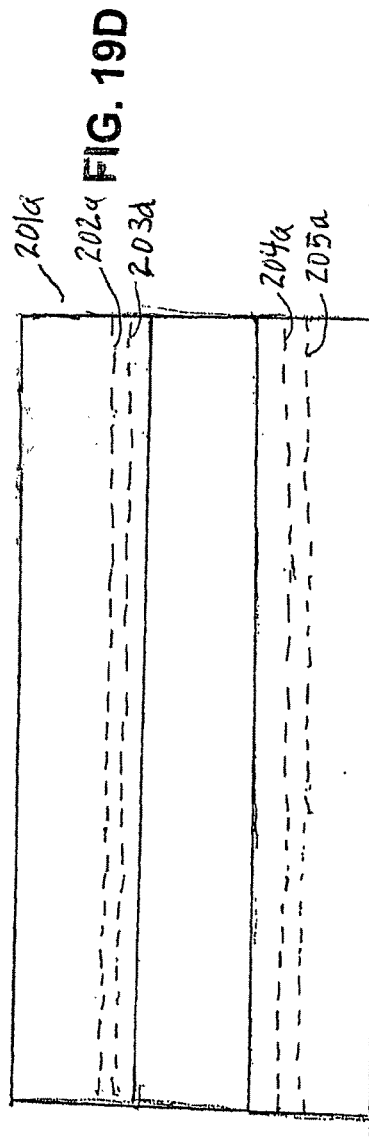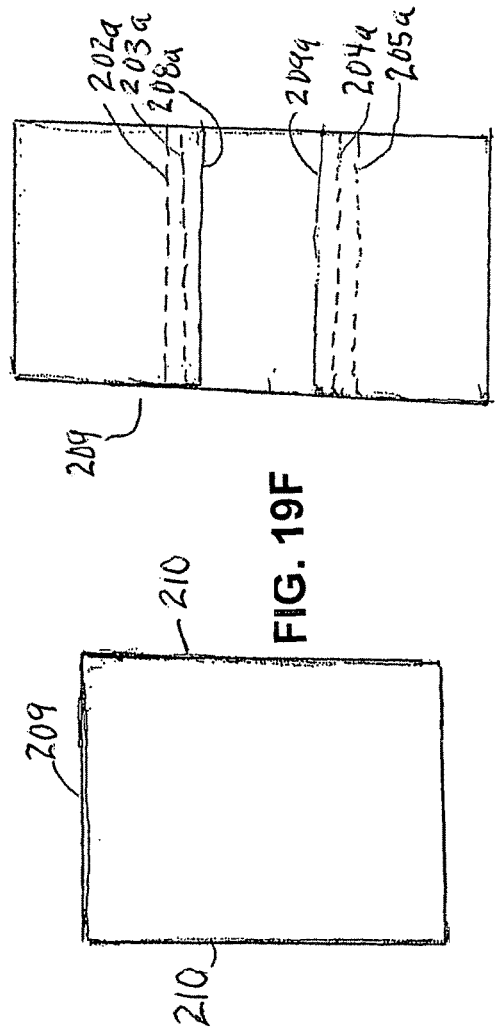

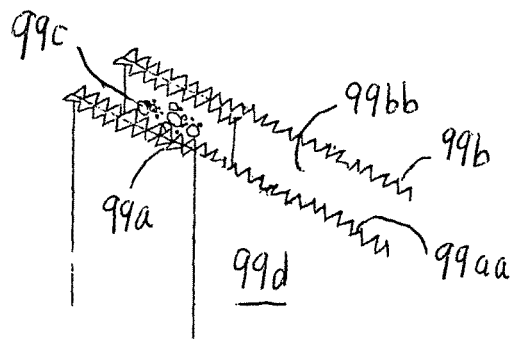
FIG. 20E
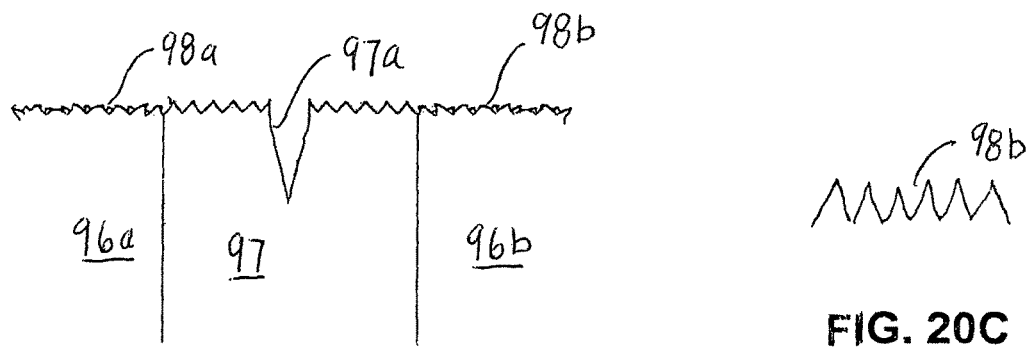
FIG. 20D
FIG. 20C
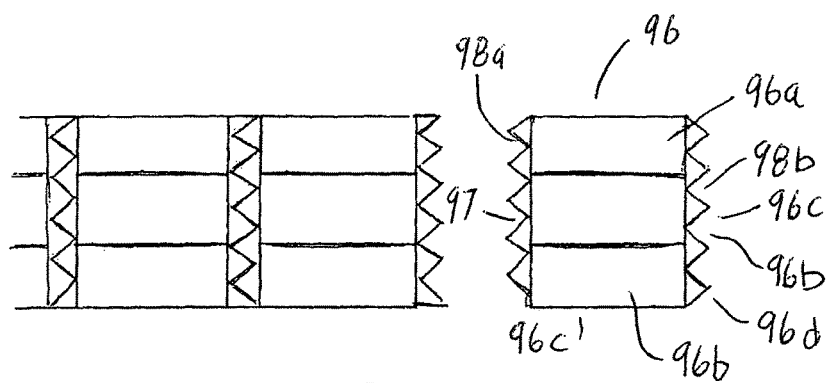
FIG. 20A

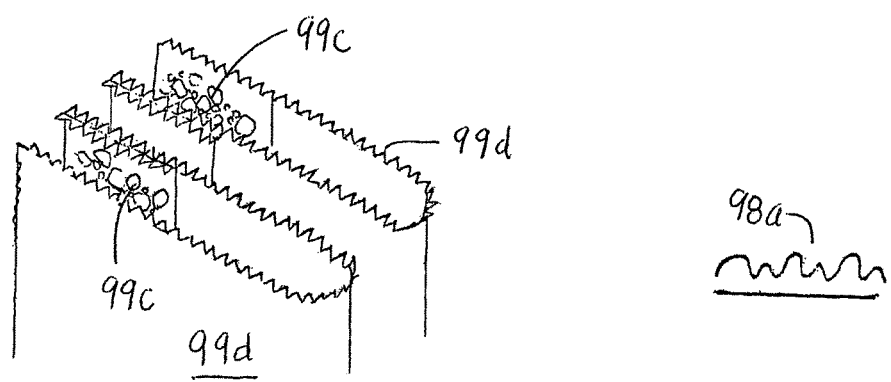

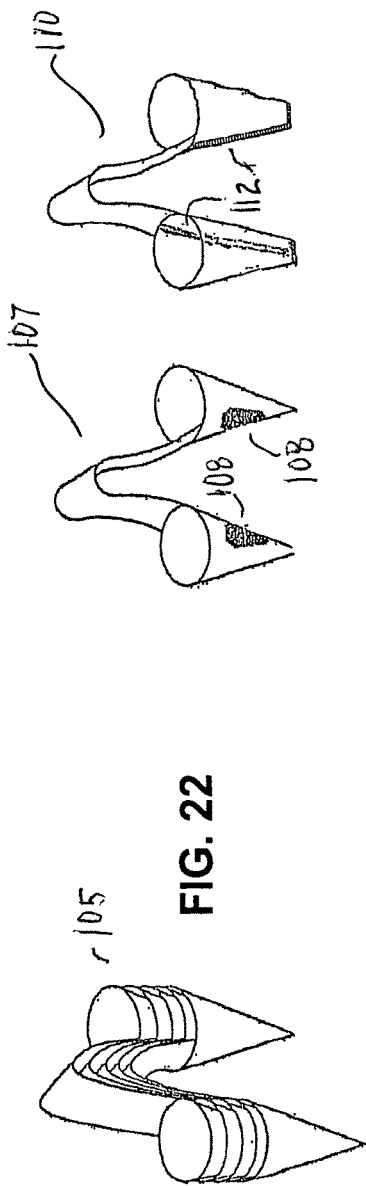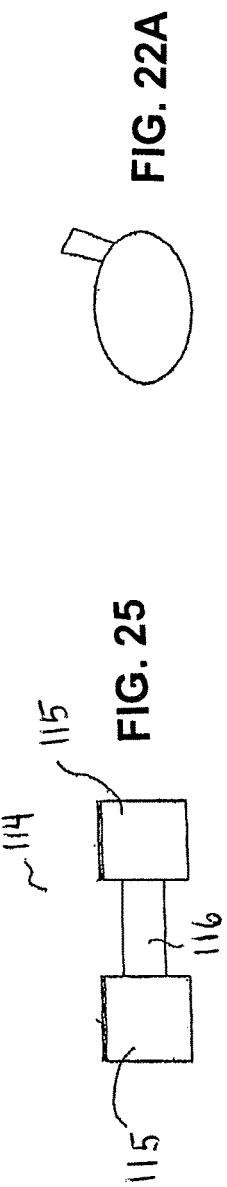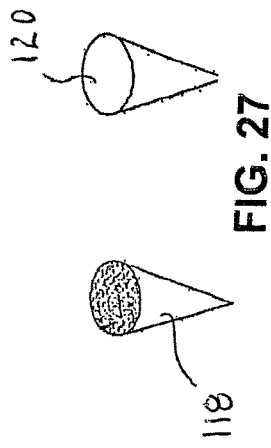

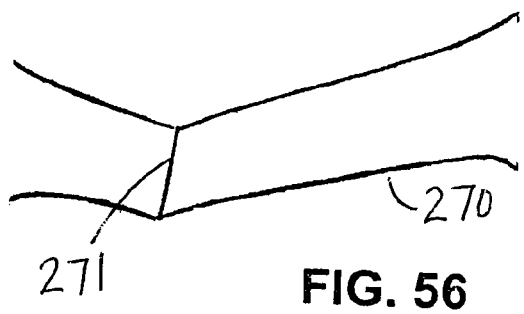
FIG. 56
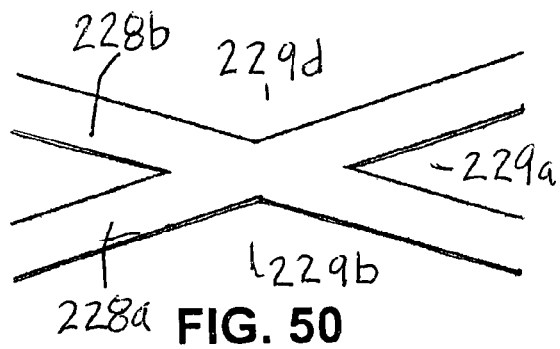
FIG. 50
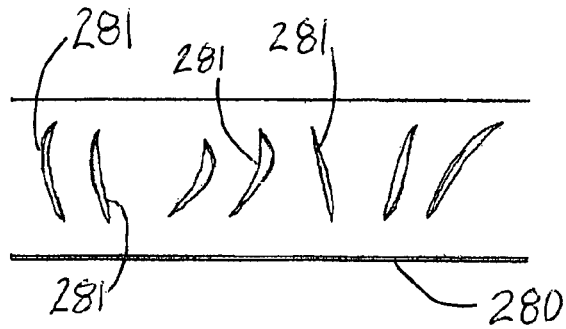
FIG. 57
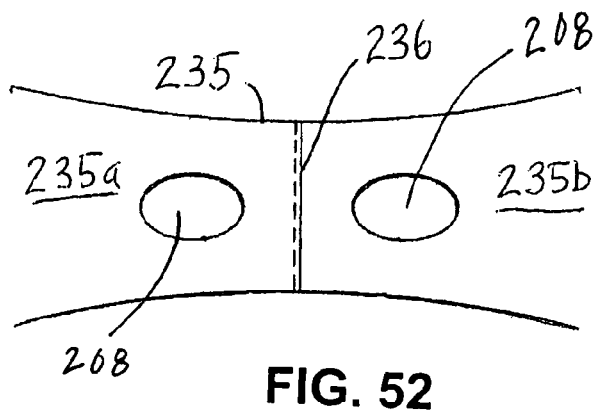
FIG. 52
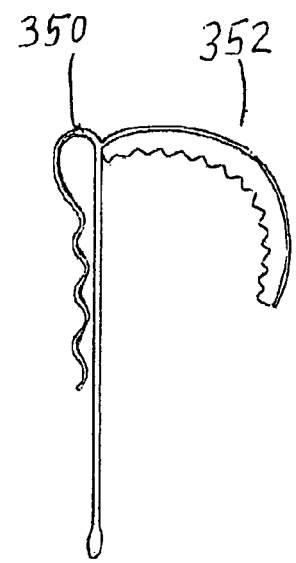
FIG. 60
FIG. 61
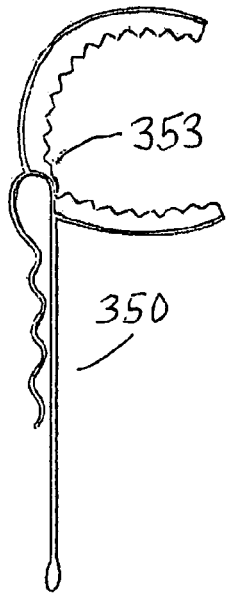

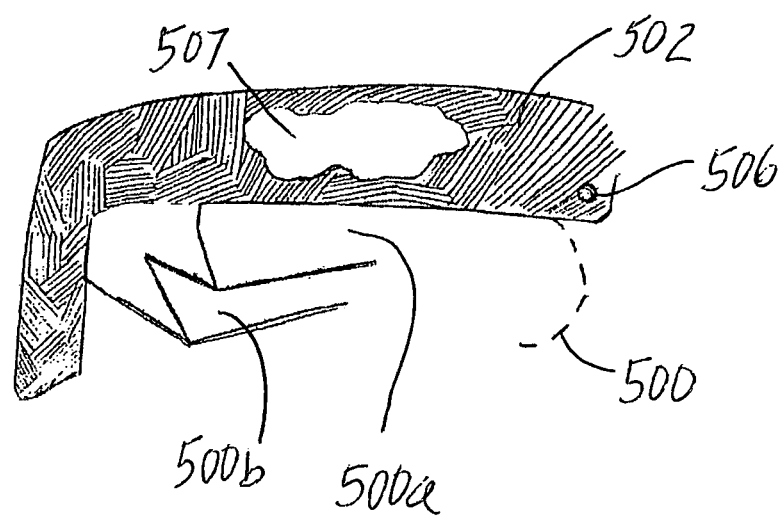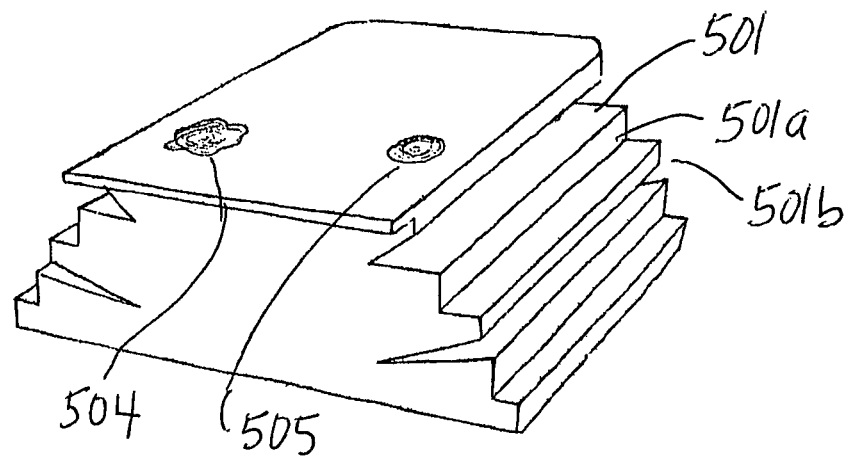
FIG. 63

DISPOSABLE FINGER TONGS FOR HANDLING A FOOD PRODUCT

RELATED APPLICATIONS

This application is a continuation in part of U.S. application Ser. No. 13/939,070 filed Jul. 10, 2013, now issued as U.S. Pat. No. 9,033,383 on May 19, 2015. The '070 application is based upon provisional application Ser. No. 61/741,052, filed Jul. 11, 2012, (the '052 application), 61/741,657 filed Jul. 25, 2012, (the '657 application), 61/796,556, filed Nov. 12, 2012, (the '556 application), and 61/848,579, filed Jan. 7, 2013 (the '579 application). Applicant claims priority from application Ser. No. 13/939,070 under 35 USC §120. The '070 application claims the benefit of the '52, '657, 556 and '579 provisional applications under 35 USC §119(e). These applications are incorporated by reference herein.

FIELD OF THE INVENTION

The present invention relates to disposable finger food holder tongs with enhanced grabbing and reduced tearability.

BACKGROUND OF THE INVENTION

Known prior art is the enclosed U.S. Pat. No. 5,848,928 of Wong which describes finger food tons ("eating utensils") with texturized surfaces, but they appear to be permanently attached, not attached manually in situ by adhesive stickers.

Disposable paper based finger food tongs are described in the Jones, U.S. Pat. No. 3,407,927. However, Jones merely discloses folding a sheet of paper or plastic material to form opposite pockets with mid-facing pocket openings, which are not sealed for sanitary use, and then heat sealing or adhesive gluing of the left and right ride edges of each pocketed food holder before being cut into separate food holders. Jones also does not disclose adherable textured regions with free ends to permit pivoting.

Kaufman, U.S. Pat. No. 3,331,626, described finger tongs with open sided, unsealed pockets.

Known prior art also includes a loosely suspended ring that a thumb is inserted in, in a boxing glove, as noted in U.S. Pat. No. 4,424,595 of Alpert. However, the loose thumb ring of Alpert '595 is not a finger stability enhancing element, and does not constrict against the fingers, while still allowing the fingers to manipulate in using the tongs for holding objects, such as food, for example. Alpert required knotted wrist laces to hold the boxing glove on the hand. In contrast, in the absence of Alpert's knotted wrist laces, Albert does not stabilize a finger or thumb in place in a pocket of an object, such as a food grabbing set of tongs. Also, in Alpert, the fingers are not free and independent to manipulate an object.

Known prior art also includes a recent pending European patent application number WO 2012/117248 of Ly from the United Kingdom of Great Britain which describes disposable paper finger tongs which are coated and textured for better gripping. However, Ly does not show the use of a central patch of adhesive on a central portion the back of the textured sticker patch to reduce ripping caused by full surface adhesive pulling against thin paper tong material. Ly also has complicated pleats to compress multiple folds to prevent unfolding of the pockets due to the resilient bias of his materials. However, Ly requires an extra-long axis of the material to accommodate the folded pleats, as is clearly shown in Ly's FIG. 4, which excessively large areas 8 of adhesive, which are not required in the Applicant's present invention. Ly's fold lines are solely for the folding, not for sealing off Ly's pockets prior to use. Also, Ly's perforations are for scoring the edges of the pocketed handling implements, not for sealing off the finger insertion pockets prior to use.

U.S. Pat. No. 5,328,439 of Goldberg describes forming a safety fringe around the edge of paper product sheets in general, but Goldberg does not describe heat or otherwise sealing of folded paper pockets. Goldberg does not describe any custom method of manufacturing fringes, such as heated knurling.

U.S. Pat. No. 8,424,541 B2 of Crawford describes a chewable tobacco or botanical pouch made of porous paper with rounded, non-sharp smooth sealed edges 12 around various polygon or other shapes, but does not describe soft, injury preventive edges with irregular free ends extending beyond a seal parallel to, and in the vicinity of a periphery of a finger(s)/thumb insertion pocket or strap of a set of tongs, to promote tearing. In fact, Crawford seals his tobacco pouch 14 with a continuous, hardy smooth edged seal 12 that does not promote tearing of the pouch 14, because tearing will be detrimental to the contents in the pouch 14.

U.S. Pat. No. 5,457,842 of Chang describes a set of tongs with soft pads to clean eyeglass lenses, but the arms of the tongs do not contain any finger(s)/thumb insertion pockets or straps that can be used to manipulated an object, such as, for example, a piece of food.

U.S. Pat. No. 3,143,276 of Nichols describes folding paper to form pockets, such as envelopes, with flaps to fold the containers. However, Nichols '276 does not describe forming finger insertion tongs with finger(s)/thumb insertable pockets or straps, with unbonded peripheral free ends of edges, used to make soft, injury preventive edges for tongs.

OBJECTS OF THE INVENTION

It is therefore an object of the present invention to provide disposable finger food holder tongs with enhanced grabbing and reduced tearability.

It is also an object of the present invention to provide disposable finger food holder tongs with optional texturization.

It is also an object of the present invention to provide strong disposable finger food holder tongs with reduced tearing characteristics.

It is also an object of the present invention to provide disposable finger food holder tongs with optional shell cracker accessories.

It is also an object of the present invention to provide disposable finger food holder tongs with optional utensils.

Other objects which become apparent from the following description of the present invention.

SUMMARY OF THE INVENTION

The present invention comprises a combination finger food holder tongs set and surface texturizing set, which includes a set of tongs with finger pockets, whereby the pockets are movable towards and away from each other for grasping an article of food; plus a plurality of adhesively adherable or otherwise fastenable sticker substrates having a first texture imparted side and an opposite adhesive bearing side with a release liner, whereby the texture containing sticker is placed upon the food engaging surface for manual grasping of articles of food.

For example, the finger accommodation areas, can be closed ended pockets, open ended pockets, a portion of a pocket, straps that a finger in inserted behind, an in-between finger(s) vertically extending tab wall, an in-between finger(s) vertically extending wall shaped like an beam, an in-between free finger(s) tabs in a pocket; an in-between free finger(s) tab strap, and/or other recessed or dimpled areas, or, combinations thereof.

The disposable finger holding tongs for handling a food product include a strip of disposable flexible coated material having a central folded region. Distal ends of the strip form jaws of the tongs, with each distal end having a pocket to accommodate a finger, thumb or fingers of a user. An optional removable seal covers the disposable finger tongs prior to use; and respective textured surfaces are provided on grabbing surfaces of the jaws to assist in holding the food product. The textured surfaces may be crimped, embossed, coated or formed in the surface of the jaws of the tongs, or may be provided on adherable stickers or substrates attachable to the jaws of the tongs.

Optionally a one side edge of the strip has perforations so that the tongs are separable from an adjoining strip whereby a plurality of the strips are formed from a single sheet of disposable flexible material, the strips being separable by the perforations. The perforations when using a single foldable sheet must be double perforation lines which will extend perpendicular to the axis of the aligned tongs, and located parallel to and close to the pocket mouth. The tong pockets each are sealed for sanitary purposes. When used, the perforation lined regions are pulled to reveal the open pocket from under the sealed portion or pieced to hug around the finger.

Optionally each pocket contains an elastic or stretchable finger contact member, such as a length of elastic or stretchable strap or ring inside and/or outside of the pockets of the tong jaws, for maintaining an opening into each pocket to assist in holding the tongs upon the respective fingers and thumb of the user.

However, it is further noted, that optionally, the set of tongs can have one or more functional connecting tabs for their specific purposes of connecting the finger accommodating pockets or other finger accommodating areas connected by the one or more connecting tabs.

It is noted however, that there are two kinds of straps optionally used in the present invention. First, straps can be open ended finger accommodating strap.

In contrast, the present invention also optionally includes finger stability straps, in contrast to Alpert '595, where the straps hug and/or are connected in part or in frill, to an interior wall of the pockets of the set of tongs. Other finger stability elements can be thicker walls, a hole in the tab, a strap, a plurality straps, one or more flexible straps, a pierceable seal in a pocket of a finger(s)/thumb accommodating region, a pierceable seal at a mouth of a pocket of finger(s)/thumb accommodating region, a pierceable perforation around an open mouth area in a pocket of finger(s)/thumb accommodating region, full stability wall with a separate material, a partial stability wall prepped onto an original material, a layered wall, a stretchable wall, a drawstring in a pocket of a jaw, a huggable pocket, a width allowance tab, a clip with a hook/ring ability, and/or combination thereof, or, in the optional absence thereof, none of the above.

The edges of the set of tongs can optionally have injury preventive features, such as soft, less sharp irregular edges including a feathered edge, a perforated edge, a fragmented edge, a frayed edge, a segmented edge, a partially straight edge, a zig-zag edge, a teethed edge, a serrated edge, a jagged edge, a rounded teeth edge, a tearable edge, an edge such as described with reference to botany plants and leaves for edges; or, a combination thereof, or in the absence thereof, none of the above. The purpose of the edge being irregular as noted above is that it reduces the peripheral surface portion touching the skin of the user. For example, with peaks and valleys, only the portion of the peaks and immediate adjacent portions of the peripheral edge contact the skin of the user. A portion is removed in creating the peaks and valleys. The other portions down in the valleys of the irregular edges do not all contact the skin, if at all. The removed portion brings the peripheral edge down to a predetermined seal, to promote tearing at that point, where the valleys meet the seal. Unlike U.S. Pat. No. 8,424,541 B2 of Crawford, the present invention describes a set of tongs made of non-porous paper with soft, irregular, non-smooth sealed edges around the set of tongs, with soft, injury preventive edges with irregular free ends extending beyond a seal parallel to, and in the vicinity of a periphery of a finger(s)/thumb insertion pocket or strap of a set of tongs, to promote tearing.

Optionally, at least one of the jaws has a food handling tool extending from a bottom end or other position place thereof, such as a fork, knife, spoon or chopsticks.

The tongs are formed from a sheet of flexible material, such as, but not limited to, paper, plastic, fabric or combinations thereof, in which strips of the flexible material form respective tongs, in which a side edge of the strip has perforations so that the tongs are separable from an adjoining strip whereby a plurality of the strips are formed from the single sheet of disposable flexible material, the strips being separable at the perforations. Optionally, one of the jaws has separate pockets adapted for individual fingers of a user.

The tongs may also be adapted to be stackable.

The textured substrates or stickers optionally include a textured food engaging side and an opposite tong engaging side, the opposite tong engaging side having a centralized adhesive region surrounded by a non-adhesive peripheral region with pivotable free ends, which are not contacting the opposite tong engaging side, to reduce the possibility of the adhesive pulling and ripping the tongs during use.

In another alternate embodiment, the sticker is attached to an elastic or stretchable ring, the elastic or stretchable ring being insertable over a respective tong of the tongs for engaging the sticker to the tong. Optionally the length of strip or ring (which optionally may be formed from two strips joined at the ends to form a closed ring) is elastic, so that when the finger enters the elastic expands and then tightly retracts upon the finger, whereas if the ring or strip(s) are instead stretchable, they will stretch when the finger is contracted, but will not retract thereafter.

In yet another embodiment, the sticker further comprises a three-dimensional C-side shaped immovable jaw member having a set of overhanging immovable jaws and ridges on the top and bottom inner surfaces thereof. The set of tongs may also have an accessory shell cracker or utensil bearing toy removably attachable to the three-dimensional C-side shaped immovable jaw member.

The disposable tongs may be produced by the method of coating a flat sheet of paper with a pre-perforated top layer, heat sealing the paper and, a) cutting the sheet at peripheral edges to form individual tongs, or b) tearing the sheet at the perforated regions, also at peripheral edges, to form individual tongs, and providing the tongs thus formed with textured food grabbing surfaces.

It is noted, however, that in a preferred optional embodiment, the tongs of the present invention also may have other perforations which are perpendicular to the lengthwise axis of the tongs, at least in the mid connecting tab region where the open mouths of the pockets are located and optionally sanitarily sealed before use, so that a sanitary cover seal can be removed or pierced along these perpendicular perforations, to reveal the openings of the pockets of each jaw of the tongs for finger, thumb or fingers being inserted into previously sanitarily sealed regions, extending at least in the central region between the pocket openings (or optionally, extending along the entire region or portion thereof of the flat tongs before use), or to hug the fingers.

The tongs may be provided in a multiple stacked relationship, the stack of tongs being supported upon a stand having a base, a column and a clip, or on a hook extending from a wall, to hold the plurality of tongs Optionally, the tongs may comprise conical members formed from a sheet, the sheet wrapped around to form the conical shape at a sealed linearly extending joint, the sealed joint being provided in such an amount to provide a linearly extending textured food grabbing linear portion. The conical tong members may also be formed from a sheet, where the sheet is wrapped around to form the conical shape, the conical members each being provided with respective three dimensional crimped portions forming the textured food grabbing surfaces.

In another alternate embodiment, the disposable finger holding tongs for handling a food product include a strip of disposable flexible coated material having a central folded region; wherein distal ends of the strip form jaws of the tongs, each distal end having a pocket to accommodate a finger of a user. A removable seal may cover the disposable finger tongs prior to use and respective textured surfaces may be provided on grabbing surfaces of the jaws to assist in holding the food product. In this embodiment, the tongs are formed from a folded sheet of flexible material folded over a set of female dies (or at least one female die) pressed by a set of male dies (or by at least one male die) to form crimped open three dimensional finger and thumb portions (and finger joints) with textured surfaces, the folded materials and the dies being provided under a shroud providing a heat sealing of the tongs. The dies can also form crimps to for three dimensional surfaces corresponding to the palm area of the tongs.

In yet another alternate embodiment, a disposable food grabbing accessory includes a flexible substrate having a flat skin contact side and an opposite textured side, the flexible substrate being attached to an elastic or stretchable band placed over a finger. The textured substrate is attachable by the tensile force of the elastic or stretchable band extending over the finger, wherein the elastic or stretchable band directly holds the textured substrate directly on the finger.

In general, the present invention is a dispensable and retrievable container/system with sanitary paper tongs in a package in relation to the dispenser and a transferable sticker in a container, with a silicone release backer. Adherable texturized stickers are provided for handling lobster and shrimp surfaces needing abrasive rubbing thereon, but which do not touch skin. This invention relates to disposable tongs which are more particularly intended for use in handling unwrapped foods, for example, in shops, restaurants, although the tongs may, if desired, be used in suitable other cases where it is desired to avoid touching substances, such as medical or pharmaceutical particles to be picked up by hand.

A common method of handling foods in an unwrapped condition in shops is to use metal/plastic tongs, which may be used a considerable number of times in the course of a day's trading between cleanings. This is a disadvantage from a hygienic point of view, particularly as in the course of such use, the food-gripping surfaces of the tongs may inadvertently be handled or soiled and disposable sanitary paper and tear under moist conditions when pressure is applied to it and in contact with rough, sharp, pointed surfaces. An object of the present invention is therefore to provide tongs suitable for the use in handling food and food surfaces which can be produced at a cost sufficiently low to make it practicable for the user to throw them away after using once only. Preferably, the tongs can be broken up after use into smaller pieces, making them more environmental sound to prevent choking of wildlife. This is accomplished by having tearable peripheral edges, which enable the user to tear the used set of tongs before disposal. The method of disposal motivates the user to dispose of the used tongs in an environmentally and wildlife friendly manner. In this method, it promotes a second finger protection feature, where, in addition to the first feature of protecting the finger(s) or thumb during use from contact with messy food being held by the tongs, but also, as a second finger protecting feature, the tearable edges of the tongs can also protect the fingers when the user puts the two food contact surfaces of both tongs against each other, so that both tongs can be torn while the user's fingers only contact the clear outer side of the tongs.

Therefore, the disposable tongs of the present invention provide a triple protection to the user. First, the soft irregular peripheral edges help prevent paper cuts to the fingers, mouth, tongue and lips of the user. Second, the tongs preferably have a central connecting tab between the two jaw pockets of the tongs, wherein the central tab can be torn to separate the tongs into two tongs, so that the two food contact sides of the respective pockets can be folded against each other, so that the user only holds the outside, clean, non-food contact area when disposing the used tongs. Third, if both the front and back of pockets are messy, the clean central tab can be torn, and folded over the back and/or front of the messy pockets, thereby keeping the hands, fingers and/or thumb of the user clean during the tear down and disposable of the used set of tongs. In this manner, the hand that is using the torn tongs can press the user's thumb and fingers together, concealing the mess on the front and back of the pockets. Then the hand that is not using the tongs can drag and fold the extended torn connecting tab over the messy front or back of pockets, therefore concealing the mess on the front or back of both pockets. With the same hand, the user can drag the set of tongs off the other hand and start the tearing down process to break the used set of tongs into small, disposable pieces.

Another objective of the invention is to overcome the tearing of the cost effective, disposable tongs. When a full glued base sticker is applied to paper tongs, it can grab multiple surfaces well, but paper tongs tear when pressure is applied to any one particular side. It causes the side of sticker with no pressure to lift, therefore pulling on sanitary paper causing tear and tears occur faster as the paper tongs get moist from food. In a preferred embodiment, to overcome the tearing and still provide a cost effective and practical disposable paper tong, the textured sticker has a central glue base only with the glue at the center of the base of sticker. It allows for the maximum grasping of the food surface and when pressure is applied to any one side of the sticker, the central glue adhesive region allows for a pivoting of the free peripheral ends of the sticker, because the outer base of the sticker is free of glue, which does not stick, is not connected it to the paper, which eliminates the pulling and tearing.

Although a fully glued base or a particularly outer perimeter glue (to save on glue) base can be applied to stronger, more expensive coated, plastic, multilayer, disposable, non-disposable tongs. According to the invention, the stickers and tongs can have optional three dimensional multi surfaces with self-locking, press in novelty or shell cracking accessories or more optionally, a zip track, wherein an accessory is pushed in and permanently or temporarily locks for rugged use and safety (not necessary for connecting tab). Locking can be temporary by the user pinching tabs located on the zip tracks. Also, the accessory can be locked in place by fasteners, such as drawer fasteners or jewelry clasps.

According to the invention, stickers can be made in plastic injections, moldings and embossed sheet systems. Disposable tongs are formed, made by a strip of paper or other poly coated or other flexible, disposable material. By folding and heat sealing, gluing and cutting, there are different methods of producing hygienic, disposable tongs, with a high volume label press, leaving a perforated top pocket connecting tab which completely seals pockets and only when the top perforated tab is torn of its, exposes the bottom pockets' connector tab and reveals the mouth of the pocket. A preferred method is a strip of paper or flexible, disposable material, which is provided at each end with a pocket and is folded about its middle so that its pockets' ends form a connecting tab so that each pocket is at the outside of the tongs and has its mouth presented towards the middle of the strip, whereby the tongs can be held in use by the user inserting a finger or fingers into one pocket and a thumb into the other pocket. Also according to the invention, a plurality of disposable tongs can have a perforated connected ability at its ends or sides with or without a perforated hygienic tab (which does not have to be perforated.) Connecting tongs can be provided in a boxlike dispenser that when pulled, a cutter on the dispensing box will cut a perforated connecting tab. Also the tongs thus produced can be stacked where the food touching side is faced down on a convex base, which allows for the pocket mouth to face up and open. Wheel allows the user to easily insert thumb and finger(s) into pockets.

Also according to an alternate embodiment of the invention, a convex, rectangular base, with two posts at each end can hold sets of tongs, which are placed on the convex base with a hygienic tab up with distal pocket tips in between posts. The narrow sides of rectangle are free moving, of whichever sides up and down so that the two narrow corner posts rest upon the distal tips of pocket. The weight holds tongs in place so the tab can be torn off, exposing respective pockets' mouths and connecting pockets' tab, insuring that only that particular user will put their fingers and thumb into that particular tongs, and none others.

The open mouth, disposable tongs can be produced in current methods of using a production press and filling the tongs in a dispenser container. Optionally the tongs are flexible, with at least one textured surface substrate or sticker adhered thereto, and which does not touch the skin. Without limitation to other embodiments foreseen by this disclosure, to recapitulate, the important salient optional features of the textured food or other item handling tongs with in situ applied textured stickers (or in situ applied other textured bearing members) include optionally at least as follows:

A. a textured sticker with a central glue adhesive back, a textured multilayer sticker, with at least one zip lock tracks
B. at least one novelty or shell cracker or utensil accessory which locks onto a sticker having three dimensional support members;
C. at least one textured sticker with an elastic or stretchable rubber band which goes over tong to hold a textured sticker in place without adhesive contact with the tong;
D. at least one textured sleeve jacket goes over the tongs;
E. a completely sealed (or partially sealed) tong before use can have a peelable, perforated release tab to keep the inside surfaces of the tong recesses free of contaminants so that when peeled, there are revealed recess pockets;
F. at least two tongs, joined together with a tearable, perforated connection;
G. an open, weighted dispenser for a plurality of tongs manufactured from a single sheet of flexible material, with pre-perforated separation lines therebetween;
H. a pull dispenser with connected tongs for dispensing tongs; or,
I. all tongs can be rounded, angled, shaped into a finger(s), etc., all can be covered with poly coated material, of a flexible material, such as paper, plastic or fabric, or combinations thereof, and can be coated on both sides, multi layered, with paper, material wax, synthetic wax and poly wax, wherein a minimal margin, to no margin, can be created by adjusting the position of the fold lines of the paper or coated poly, flexible material, where the pockets' sides are a natural fold and seam of a flexible material and seal, at locations, such as, for example, on bottom of pockets and on top or bottom center, like a manila envelope.

The optional textured sticker to start with has a predetermined design so when the user's thumb meets fingers, it mimics a bird beak to pick up pieces of food, such as meat or other food products, to be grabbed and consumed.

The tongs can have more than one sticker with protruding, abrasive textures, and the texture can be of a fanciful but abrasive texture, such as the face of a character, such as a design where two stickers meet to make a character on the tong's surfaces.

A male part on open sticker can insert into another sticker's female part when two stickers become hinged or solid locked, with an ability to become or hold fanciful and/or functional accessories, such as characters which can function as shell crackers, meat tearers, etc.

The textured stickers can be embossed with a product such as known as poly 2301 Pioneer WI54868, 800-319-2477-751-234-9186.

The tong's pockets and respective food touching surface and/or entire back and front can be coated, printed, dipped, etc., in rubber, plastic, acrylic, etc., with or without pieces of crushed nutshell, processed corn bits, etc., to create a gripping surface with a bonding ability, that is sanitary and digestible.

Exterior paper on the bottom of each pocket can be shorter on top or back of each tong pocket so that a finger and thumb can find themselves into the recess of the pocket, because the pockets can be provided with a different size of FDA approved material on each side and top opening of pocket on food touching side where it meets the tab, which may be longer than the back or pocket. This allows for easier finding of the openings of each pocket of each tong. A shorter back side can still be sealed, glued, etc., anywhere on the respective folded edges thereof.

In the coating process, a multicoated paper, such as aluminum is coated with paper, and then the paper is coated with poly wax.

In this process, at least a portion of the product can have textured, coated, multi coat surface.

Although adhesives, glue and heat sealing can be used, a cold seal method can also be used. Additionally joints can be sealed when the flexible FDA approved material forming the tongs is rolled, crimped, sewn, knurled, etc.

Coatings help strengthen the paper tongs, which when used, break down quickly, with use and handling food. A paper water shield can be added from the minimum amount to the maximum amount to get the tong stronger when it is wet. Water strength depends upon the amount of adhesive sprayed on at the time of turning pulp.

Multiple coatings can be applied with or without increased water resistance strength. The more adhesive applied, the more crinkly the paper is, which is undesirable for a napkin use. But in the use of a finger tong, it will add a needed strength to hold up against moisture and to keep the ink print on paper. Without the paper strength, any indicator or decorative ink tends to dissolve into the tissue, which then grossly dissolves into foods, although food-compatible, non-printed, coated FDA approved material and/or edible ink can touch the food.

Tongs can also be made with FDA approved material such as used in making paper towels, i.e., for example, paper of two plys or more, or one ply paper. Although Kraft chemical pulping adds more dry strength by allowing chemical bonds, which can be enhanced with more dry strength additives, such as cationic starch in the form of bleach, bleach pulp of a paper napkin tissue, but it may still need wet strength by the aforementioned coating. Although wet strength and process are still in the experimental stages in the chemical pulp, wet strength additives such as polyamidoamine-epichlorohydrin resins may be added at a point in processing where the pH level is good, such as between 6-9, is then mixed with good negative charged amounts and without excessive positive charge when adding resins. In some cases, cationic wet strength resins can be improved by adding carboxymethykellulose or other negatively charged additives.

Heat or glue sealers can make the tongs of any size, so as to be any size or geometric shape, with a function, for example, the tongs may be sealed in the shape of being rounded around fingers and/or a thumb and in front of or tips of fingers or thumbs. This will allow for when fingers and/or a thumb grab an article of food or other item. It allows for the things to be grabbed by the tongs, as the jaws of the tongs are brought together by the fingers and thumb acting cooperatively. This creates a region for food grabbing, which helps hold on to food within a contoured conformational shape around the food article being held therein.

The tongs can be sealed anywhere to create different food nesting shapes and/or finger stability enhancement methods. The jaw pockets can be equal sized, or two different sized pockets or one universal pocket, where the user places the pockets over both the thumb and finger to grab foods. The tongs are coated to form a stronger FDA approved material to hold up against moisture-laden foods, for example, moist fruit salad or chow mein, to prevent the tongs from breaking down and dissolving into foods that are moist.

Each tong's pockets' respective seams can be provided on the outside and/or on the inside of the tong's pockets, which can have a seamless edge, frayed edges and/or edges cut in any shape or shapes, or turned inside out, like socks, and be produced with an air suction method or other methods.

Each set of foldably joined tongs can have multilayer paper and/or poly plastics, with poly or paper in between, and/or poly coated FDA approved material, to stop grease penetrations. With heat, glue or other sealer, the closed end of the pockets are sealed, but the open ends can be opened from a sealed state where the user tears a perforated line of the tongs, either partially or fully around the tongs, to remove a sanitary seal covering the pocket opening of the jaws of the tongs, which the user removes, which reveals the pocket for insertion of the finger, fingers or thumb therein.

If made of paper, the tongs can have wet strength glue that is poly based and other additives that are food compatible, but of synthetic and/or natural FDA approved material, and which may be coated or not coated, such as by being embedded in the paper FDA approved material to be folded and formed into the tongs.

Mylar, which is more flexible than paper, more durable and has an oil resistance feature, can be used as an alternate embodiment for the flexible sheet FDA approved material, from which the tongs are made from.

An example of a machine for processing flexible sheet materials can be a FLEXO® machine, which is rotary-line operational. The optional permanent glue can be NCR ink adhesive. The flexible material may be MYLAR® (film) under the TYVEK®® trade name. The Mylar material is processed in layers with adhesives, and cut to reveal a second layer.

When the tongs produced has a top connector (tab), the process of making is still the same, except in that the tab is left, then cutter cuts the material and adhesive is added. To insert a drawstring from a reel of string, insertion starts at the beginning of the insertion process, then is placed in between sheets before a needle pulls through a length of the draw string to form a pull string which then can close the mouth of pocket, until opened by the user to reveal the finger insertion recesses in the tongs, or just pre-sewn into the material.

Optional steel dies can start the tong forming process for three dimensionally shaped tong pockets process, which are then optionally crimped or otherwise shaped to provide the textured surface, which can be a pattern, a random accumulation of texturization, or can be contacted with a glob, or squirt of silicone glue placed on the food grabbing side of the tongs, which glob of silicone Is formed into shapes, tools, logos, characters, which are then adhered to the surface texturization of the tongs.

In an alternate embodiment, a food handling product is made from suitable materials, and has an important feature to help prevent injury, wherein at least one functional tab connector provides a functional use and/or feature for the user, where in at least one functional finger/thumb accommodation area is presented and at least one finger/thumb stability area is optionally provided. Furthermore, in certain circumstances, at least one additional functional connecting tab can be provided to assist another connecting tab where in at least one functional finger/thumb accommodation area is presented and at least one finger/thumb stability is optionally provided.

As shown in FIG. 5A and in the alternate embodiments, the tab between the two jaws can be provided outside the palm area, because it allows for a universal size finger accessibility entrance into the pocket, which allows the tong to open wide, top, central and bottom. In other words, since the tab is outside the palm area, between the thumb and the fingers it alleviates the situation where when a user with small hands/fingers uses the universal fitting tongs, it creates an unstable condition for the smaller hand user because the free-swinging pockets do not allow any allowance of adjustment or control or stability of the pocket, and the optional stability holes on the tab shorten the small hand fingers of the user from going into the finger accommodation area. Therefore, there is a need for a width allowance for the connecting stability tab that adds a pocket adjustment, stability feature and control for users with small hands. The length of this tab will determine the distance and ratio of stability snugness from the distance in-between the tab and palm. In addition, this width allowance tab allows less spreading apart of the pockets and it also allows the finger/thumb accommodating areas to pull back snugly on the user's fingers/thumb when the user spreads his or her fingers and thumb away from each other. For any given reason or task, a user wants their hand to open or close naturally and freely for their own comfort, function and/or performance, even if the task only requires the use of fingers. So, another tab can be introduced to include medium sized users to receive the advantages and to prolong the life of the tong by introducing an extra stretch tab to help prevent stress tears and/or rips, while also enhances the performance during usage. It is also important for the reader to understand that although a person slips on, for example, a knitted, rubber, plastic glove that covers entire hand and wrist area and although it may be sized in the wearer category, the wearer still has to adjust the glove continuously before, after, and sometimes during the act of grabbing objects such as cups, shovels, balls, tools, etc. Even though the object might be small enough to fit in the wearer's hand, the object is still held awkwardly and/or difficult to get a good grip on it, because naturally there's nothing like the user's bare hands for getting hold of something, because it just feels and can get an instant secure grabbing grip. The object of this example is to show that it is even much tougher to maintain and secure pockets and/or finger/thumb accommodating areas of a tongs' item, on only the bare fingers/thumb while giving control, stability, comfort and proper usage. It is urgent that a protective, comfortable item, such as a pair of tongs, be custom fit for one particular user size category with an accommodating and a connecting feature only is offered and to save on cost for certain situations a multiple sizes of user's item is provided so multiple users of the tongs can get the protective advantages and feel, grab and maintain integrity of a particular item, with at least one accommodating and at least one connecting feature. It is also important that when presenting a set of tongs for a multiple sizes to, that the tongs can be provided, with at least one finger accommodation area and at least one connecting tab area and/or an individual user size category with a particular accommodating area, and a particular connecting tab feature area. It is also preferable that the tongs use a flexible yet firmer material for stability, durability and other enhancement, since it is already known that injuries such as paper cuts can happen and if a user is using item around face/mouth area, it is urgent that finger, mouth or lip cut injuries are prevented. Therefore, it is very important that an optional soft ragged peripheral edge and/or at least a portion be determined to be less sharp. In addition, this soft ragged feature assists by adding a familiar identification and recognition of the item with or without the enhancement material to prevent paper cuts of the finger or thumb of the user.

When grabbing different-shaped foods such as a turkey drumstick, which is wide at the top, meaty part and gets narrower at the bony section and then wider at the cartilage end; or a rib, which is wider at the meaty top and narrower at the bone and wider at the sternum connection or any other cuts or slabs of meat, or when grabbing objects such as pear-shaped fruits and vegetables that are narrow at the top and wide at the bottom and also odd/oblong-shaped fruits like mango and avocados. When grabbing different-sized objects such as a cam shaft, in which the lobes on the shaft are positioned at different points and lobe positions on shaft are apart with wider, then narrower lobes, then back to wider, in series on the shaft. Another example is a painter painting a doll's leg where the doll's calves are wide and the ankle is narrow and then wide again at the feet.

All tabs and tongs can optionally have a logo. Another example of an object to be held are candlestick holders that are hour-glass shaped to narrow, to wider, to narrow, to round or square base. The tongs are optionally made to hold different shapes and sizes of tools, picture frames, Christmas ornaments, dishes, foods, cups, wine glasses, etc., as for examples. For grabbing the varying contour pieces, then individual adjustment, stabilizing, connecting, accommodating features and methods, can be introduced in the tongs for grabbing that particular item, and/or user size, etc. When the usage of a pair of tongs is needed for holding an object requiring particular adjustment, stabilizing, or at least one connecting and accommodating features for the task of users is needed, the FDA approved and/or food service culinary customarily used materials forming the tongs can be manufactured by physical and/or mechanical set up and/or use of different raw FDA approved and/or food service culinary customarily used materials of liquids, chemicals, acids, glues, solid roll/sheet FDA approved and/or food service culinary customarily used materials coated, extruded, brushed, squeezed, layered, textured, sprayed, splattered, mist, loosely felted, spandex, knitted, woven, parchment silicone, laminated, air/gas applied/cured and other known methods in the arts, etc. In addition to paper formation methods described in wwwpaperontheweb.com, Encyclopedia Britannia, Wikipedia and such, the tongs being made are prepped and prepared in a full and/or partial manner, with desired FDA approved and/or food service culinary customarily used materials, on any sides and/or just left unworked.

In order to grab the aforementioned varying contoured and dimensioned items being held by the tongs, the single function or multi-function tabs between the two jaws of the tongs can allow, for example, a stretchability feature in the connecting tab, which is presented on the tongs for extra stretch as needed. A second tab, which can be a different size than the other tab, for example, shorter, when combined with the larger tab, will allow smaller hands to have a stable width opening allowance. For example, a wide-open tab can also be presented to accommodate large hands. At least one tab can be presented anywhere on the tong for a specific purpose, size, user, job, feature, task, comfort, etc., so that the aforesaid pair of two tabs can be determined, and also be less sharp to prevent paper cuts.

All tabs as mentioned include a tab selected from the group consisting of a universal entrance wide open connecting tab, a universal extra wide open connecting tab, a width and stability allowance connecting tab, a stretch connecting tab, super stretch connecting tab, a crisscross venting width and stability allowance connecting tab, a crisscross venting stretch connecting tab, a perforated tearable connecting tab, a theme connecting tab, a game connecting tab, a tearable napkin accommodating connecting tab, a tear allowance connecting tab, a perforated bendable connecting tab, an ergonomic connecting tab, a slit stretch connecting tab, etc. The one or more tabs can be any geometric shape and include shapes such as an oval, wings, people, a place, a thing, a character, slit, slits, cuts, diamonds, and/or decorative origami folds.

All tabs can be in or out of the palm area between the thumb and finger jaws, and/or with a full closure, partial closure or no closure between finger accommodating areas. Each manufacturing process of making the respective connecting tabs each can requires its own and unique method and type of different tool design, mold, dies, machine set-up, procedures, etc., and the method of setting up, in addition to uses of mentioned tools, dies, molds, etc., or in combination with each other.

A further option includes a finger accommodating making tab, where a set of tongs is formed from a foldable template, that has one or more insertion tabs (on one or more sides of the template) that connect two parts of the flat template to forma three dimensional pocket or other finger accommodating feature of a set of tongs.

All versions of the tongs can optionally have a breakable seal anywhere in the pocket, which can be heat-sealed or glued, can be at least perforated, heat/glue sealed in/or around the entrance of the pocket and/or inside the pocket. Seals can be provided in singles, doubles, channels so when fingers are inserted into the pocket, it tears the seal, therefore hugging the untorn portion of the seal around fingers. Also, each pocket of the tongs can be fully-sealed at the mouth with a breakable, perforated portion. Therefore, a person can pierce their finger/thumb into the perforation at the mouth and into the pocket, where the untorn perforation hugs around the fingers/thumb and/or a pull string/thread can be pre-glued/sealed in the pocket, with at least a portion protruding out of the pocket in which the string/thread is pulled to reveal the pocket entrance. Any of these versions can be made from a single sheet/roll of FDA approved and/or food service culinary customarily used material.

The tongs can also be provided optionally with a logo or print, be coated, layered and/or textured, shape, cut and feel recognition.

When needed for grasping certain objects, such as pieces of food, the tongs can be presented with connecting tabs, which can function on their own and/or become supplemental assisting tabs, which can assist each other, to improve the life of the tong, by reducing stress on the tong under different sized users doing different functions at the same time. The tong can have tabs between the jaws, which can have perforations, which separate them to be used on individual fingers/thumb. Each individual portion can have a stability method feature, for example, a hole can be provided where a finger is initially inserted into and then into a finger/thumb accommodating area.

Another method of stability can be an entire wall/strip of a different FDA approved and/or food service culinary customarily used material, where at least a portion of that roll/sheet FDA approved and/or food service culinary customarily used material is of a different gauge, thickness, strength, rigidity, flexibility, coated, layered, weight expressed in pounds, etc., and is pre-worked with texture/ glue and/or prepped for sealing and is laid on a second sheet of FDA approved and/or food service culinary customarily used material that is of a second gauge or thickness, etc., of FDA approved and/or food service culinary customarily used material. This method will make at least one wall different from the others.

Another stability/control method can be a peelable glue strip at the top of the pockets, where after inserting fingers into pockets of the jaws of the tongs, a user can peel the glue strip and press against the user's fingers and/or hands.

Another method of stability is a strap/band that extends from one side of the tong to the other side, which can secure itself on the hand or on the other side of the tong. It is securable by a peelable glue strip and/or sewn through at least one hole and/or locked in grooves/slits. These side-to-side straps/ bands can be stretchable or non-stretchable and can wrap around hand/wrist areas and/or fork off to at least two bands which can go around wrist areas.

All tabs as aforesaid mentioned, and including stretch tabs and extra-stretch tabs, super stretch tabs, width allowance tab, wide open tab, extra wide open tab, crisscross allowance tab, tear allowance tab, etc., can be configured in any geometric shape, including, for example, shapes of ovals, people, places, things, characters, and can optionally have slits, cuts, diamond folds, and/or origami folds. All tabs can be a frill closure, partial closure or no closure between finger and thumb accommodating areas.

The tongs can be optionally manufactured by hot foil stamping, heat crimping, hot stamping, heat-sealing, gluing, etc., which are some of the procedures useful in making tongs of the present invention. Although it is known of other methods may be used, such as RF, ultra sonic, vibration, etc., the related set up costs, materials, etc., may be different at different costs.

With respect to the tongs, optionally the tongs have at least one finger/thumb accommodating area for finger insertion therein, including the following:
 A. pocket;
 B. one or more flexible straps;
 C. one or more straps;
 D. an in-between finger(s) vertically extending tab wall;
 E. an in-between finger(s) vertically extending wall I-beam tab;
 F. an in-between free finger(s) tabs is a pocket;
 G. in-between free finger(s) tab is a strap;
 H. free finger(s) being dimples;
 I. free finger(s) jaws; or,
 J. a combination thereof.

In another preferred embodiment, the tongs include at least "one or no" finger stability method, including the following:
 A. a hole in the tab;
 B. a strap;
 C. a plurality of straps;
 D. one or more flexible straps
 E. a pierceable seal in a pocket of a finger(s)/thumb accommodating region;
 F. a pierceable seal at a mouth of a pocket of finger(s)/ thumb accommodating region;
 G. a pierceable perforation around an open mouth area in a pocket of finger(s)/thumb accommodating region;
 H. a full stability wall with a separate material;
 I. a partial stability wall prepped onto an original material;
 J. a layered wall;
 K. a stretchable wall;
 L. a draw-string in a pocket of a jaw;
 M. a huggable pocket;
 N. an allowance tab;
 O. a clip with a hook/ring ability;
 P. a plurality of finger stability methods;
 P. a combination thereof; or,
 Q. none of the above.

In another preferred embodiment, the jaws are connected by a tab extending therebetween, including at least one finger-accommodating connecting tab of one or more of the following configurations:

A. a universal entrance wide open connecting tab;
B. an extra wide open connecting tab;
C. a width and stability allowance connecting tab;
D. a stretch connecting tab;
E. a super stretch connecting tab;
F. a crisscross venting with width and stability allowance tab;
G. a crisscross venting stretchable connecting tab;
H. a perforated, tearable tab;
I. a tab that has the configuration of a theme or character;
J. a game tab;
K. a tearable napkin accommodating tab;
L. a perforated, bendable tab
M. an ergonomic tab;
N. a slit stretchable tab;
O. a tear allowance connectors tab;
P. a tearable cut in the connecting tab;
Q. a tearable tab for independent use of a stability pocket;
R. a notch at a hardened pocket sealed to promote tearing from a continuous tearable tab cut in which the cut presents a tearable soft edge in finger accommodating areas;
S. a tab acting as a puppet;
T. a plurality of tabs connecting the finger accommodating areas;
U. at least one perforation in one or more connecting tabs;
V. a combination thereof.

The tongs are disposable, and made of at least one type of material, which may be one of the following:
A. coated;
B. uncoated;
C. layered;
D. textured with a manufactured texturization;
E. textured with an adhesively attachable textured sticker;
F. knitted;
G. woven;
H. fabricated; or,
I. a combination thereof.

When optionally prepared as multiple sets of tongs for one or more sheets of forming material, such as paper, the tongs are each separable from each other by a perforation of at least one type of optionally soft, less sharp, type of cut as follows:
A. a perforated edge;
B. a fragmented edge;
C. a frayed edge;
D. a segmented edge;
E. a straight edge;
F. a zig-zag edge;
G. a teethed edge;
H. a serrated edge;
I. a jagged edge;
J. a rounded teeth edge;
K. a tearable edge;
L. a reference to botany Plants and leaves for edges; or,
M. a combination thereof.

All versions of the alternate embodiments can accommodate at least one finger/thumb, or a plurality of fingers and a thumb.

To make double or more tabs connecting the pairs of jaws, materials can be folded as many times as needed to make as many tabs as needed, and/or be layered as many times as needed to make multiple tabs.

At least one finger tab accommodating area can have a free finger ability, wherein there is a strap(s) and/or pocket(s) to accommodate at least a finger/thumb and then a free open finger accommodating area for an additional finger to rest against, without being confined.

As noted above, the tabs can be vertically extending walls or I-beam shaped walls.

The in-between Finger(s) at least one tab versions can be curved or can be flat vertical. Another example is an "I" beam structure that is textured to accommodate the side of a finger. This accessory can have a peelable glue or be pre-made on the tongs from a factory. This version can also accommodate dimpled/textured areas.

Slit/cut stretch tab can have slits/cuts at any angles and/or directions and a slit can be part of another slit in another direction ex. Letter I, it also allow for expandability while still having enough protective FDA approved and/or food service culinary customarily used material to protect hands from getting soiled.

The tear allowance connectors tab prevents a tear from traveling because individual finger accommodating area connectors are connected separately side by side from each other so if a stress tear starts on one of the connectors and rips through fully there will always be another to maintain the integrity of the tong.

Another tab can be a puppet tab, wherein die-cut images are not fully cut out, leaving the uncut image still on the tab, so when the tab is stretched or in use, the uncut images become moveable. Images can be printed and/or die-cut.

In an alternate embodiment, the set of tongs can have tight shut mouth stabilizing jaws, such as pockets, each having an optional "stabilizing tight body" with a closed mouth shut finger(s)/thumb insertion opening, preferably with an injury preventive soft cut feature in which the soft cut style in addition adds an identification familiarity recognition visual appearance to the tongs and the soft cut additionally and furthermore, the tongs allow for an easy tearable connecting tab so that each of the pair of the individual tight shut-mouth stabilizing pockets can be independent in use of each other, by tearing apart, in which each individual tight shut-mouth stabilizing pocket can independently stabilize itself on a finger(s)/thumb. In this version the tongs have at least one finger/thumb accommodating area and at least one connecting tab, as well as optionally at least one additional stability feature beyond the tight shut mouth and/or stabilizing body of each pocket of the tongs.

In this embodiment, a deeper or longer soft cut feature can be provided anywhere on the connecting tab and be used to tear the tongs in two pieces. This at least one soft cut can be deeper/longer to emphasize a separation point on the tongs for each tight shut mouthed jaw of the tongs to be used individual freely, and optionally, where one or more of the jaws, preferably pockets, can have tight shut mouth stabilizing features, and at least one pocket can optionally have a front bulge.

BRIEF DESCRIPTION OF THE DRAWINGS

The present invention can best be understood in connection with the accompanying drawings. It is noted that the invention is not limited to the precise embodiments shown in drawings, in which:

FIG. 1 is a perspective view of one embodiment of the tongs of this invention showing the location of an elastic or stretchable member in each finger recess to aid in insertion, tight fit and withdrawal of a finger from a recess, wherein the elastic or stretchable member can be one or more elastic or stretchable strips inside or outside of each finger/thumb insertion tong, or can be a closed loop ring, either formed by joining two linear strips at respective end pairs, to form a closed loop when two laid parallel strips are on a folded portion of a sheet of material and the fold line is parallel to each strip, whereby folding over the intermediate fold line causes the strips to lay co-terminus on top of each other, where they are spot sealed at each end to form a closed loop, or alternatively, a prefabricated ring is inserted flattened into each tong and sealed in location at opposite ends thereof, wherein beaded glue will stick to the paper and allow for stretching.

FIG. 2 is a side elevation of the tongs of FIG. 1.

FIGS. 2A, 2B show strips of tear-off tongs with smaller offset open thumb accommodating portions and a knife and thumb forming region associated with forming same.

FIGS. 2C, 2D show strips of tear-off tongs with smaller centered open thumb accommodating portions, and a knife and thumb forming region associated with forming same.

FIG. 3 is a perspective view of the elastic or stretchable ring which is located by illustration in FIGS. 1 and 2.

FIG. 3A is a perspective view of an elastic or stretchable linear strip cut from a roll of elastic or stretchable material.

FIG. 5A is flat plan view of an alternate embodiment for a ring structure of FDA approved and/or food service culinary customarily used material with finger insertion openings where two rings are joined by a strip region at a common edge, and have extending therefrom the textured finger grabbing portion, or use of a textured sticker as in FIGS. 4, 5 and 7. Optionally, sleeve pockets or holding bands can be added to the finger grabbing portion.

FIG. 5B is a top plan view of contoured die cut hole with contoured figure outline shapes of an alternate embodiment of the ring structure of FIG. 5.

FIG. 5C is a top plan view of an alternate embodiment for a cover for the ring hold of the ring structure shown in FIG. 5, with perforatable attachments to a holding band of the ring structure of FIG. 5A.

FIG. 5D is a top plan view of a ring hole with serrated or undulating projections to snugly grip a finger in the ring hole of the ring structure of FIG. 5A.

FIG. 5E is a cushioned layer overlapping an edge of the ring structure of FIG. 5A.

FIGS. 5F and 5G are perspective views of a single ring embodiment finger tool.

FIG. 5H is a detail view of an auxiliary textured tool attachable to a finger tool.

FIG. 5I shows an optional second ring 301*c* to hold a distal end of a second finer for stability and strength.

FIG. 7 is a perspective view of a three-dimensional multi-layer sticker with a C-side shape and ridges on the top and bottom inner surfaces for accepting an assembly consisting of a toy temporarily attached to top and bottom ridged blocks which mate with those in the sticker.

FIG. 8 is a front view of a toy with a press-in protrusion on its back.

FIG. 9 is a side elevation of the toy of FIG. 8.

FIG. 10 is a side elevation of a screw-engagement protrusion next to a perspective view of a flat sticker with a central threaded hole.

FIG. 11 shows two side cross sections of deep stickers, one with a central recess to engage a press-in toy and the second with a threaded central hole to accept a threaded protrusion on the toy.

FIGS. 19 D, 19E and 19F show an alternate embodiment where the tongs are produced by only a single sheet of folded paper, as opposed to the two paper sheet layers of FIGS. 19A, 19B and 19C.

FIG. 20A is a close-up front view showing a pocket with soft, irregular edges cut or torn off during production.

FIGS. 20B and 20C are detail views of different soft, irregular edges.

FIG. 20D is a close-up view of a tongs with a tearing tag and soft, irregular edges.

FIG. 20E is a close-up perspective view of two separated jaws being joined with food contact areas adjacent to each other.

FIG. 20F is a close-up perspective detail view showing a messy food contamination on both the front and back of respective pockets of the tongs.

FIG. 22 is a perspective view of a nested stack of tongs of this invention having conical recesses for finger insertion.

FIG. 22A is a sanitary lid for insertion over the top cap of a stack of tongs.

FIG. 23 shows a perspective view of tongs with conical recesses having crimped facing food-contact areas.

FIG. 24 is a perspective view of tongs with truncated cone finger recesses with facing crimp seals which form the food contact areas.

FIG. 25 is a flat plan view of a flat cutout which can be formed to produce tongs with conical finger recesses; two distal rectangular sections with a stripe of adhesive at one edge are formed into the cones.

FIG. 26 is a perspective view of tongs made from the plan cutout of FIG. 25.

FIG. 27 shows a perspective view of a coated paper cone and a conical heated mold used to bond the cone.

FIGS. 50 and 51 are detail views of venting and/or stretchable connector tabs for toys with crisscrossed straps.

FIG. 52 is a detail view of a connector tab with perforation line and finger insertion holes.

FIG. 56 is a detail view of an ergonomic tab with unequal length portions.

FIG. 57 is a detail view of a connector tab with slits.

FIG. 60 is a detail view of a clip with a hook attachable to a connector tab of a pair of tongs.

FIG. 61 is a detail view of a clip with a half-ring hook attachable to a connector tab of a set of tongs.

In FIG. 62I, optional edge cuts (as described previously) are shown.

FIG. 63 is an exploded diagrammatic view of an alternate embodiment with male and female dies for producing tight, shut mouthed jaws (such as pockets) of the set of tongs, optionally with a bulging portion of the food touching side of the jaws of the tongs.

DETAILED DESCRIPTION OF THE INVENTION

Figure 5:
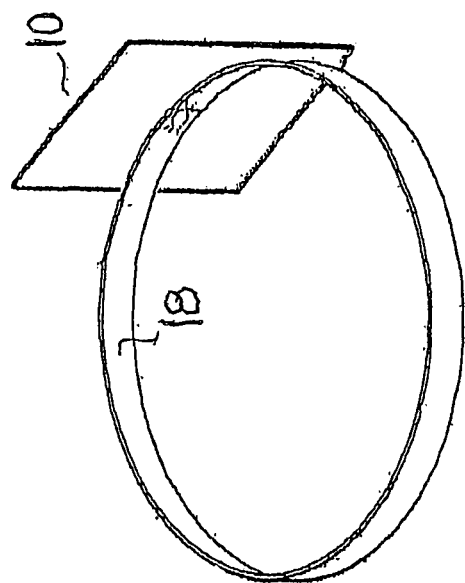
FIG. 5 is a perspective view of a sticker attached to an elastic or stretchable band capable of attaching the sticker to a finger recess by the tensile force of the elastic or stretchable band.

The present invention has broad applications to many technical fields for a variety of articles. For illustrative purposes only, a preferred mode for carrying out the invention is described herein.

FIGS. 1 and 2 show one embodiment of the tongs 1 of this invention showing the location of an elastic or stretchable member 5 or 5*a*, such as one or more strips 5*a* or a ring 5 in each finger recess 2,3 to aid in insertion and withdrawal of a finger from a recess 2 or 3.

The tongs are formed from a flat folded sheet of flexible heat sealable FDA approved and/or food service culinary customarily used material, such as coated paper, plastic, fabric or combinations thereof, such as cotton/polyester, or fabric strand strengthened paper, such as linen paper, for example. One side of a finger insertable tong can optionally be made of one FDA approved and/or food service culinary customarily used material, such as coated paper, and another side can be made of coated plastic or coated fabric. Each closed finger sleeve 2 and 3 has a closed distal region 6 and an open finger insertion region 4, with an optional draw string for tighter fit around the finger or fingers. The draw string can be pre-sewn, or sewn in during folding, heat sealing and cutting processes of producing the tongs. Die cut perforated holes at the mouth of each pocket can be imparted for improved stability of the tongs holding a finger, thumb or fingers therein. The elastic or stretchable member 5 or 5*a* can be one or more elastic or stretchable strips 5*a* inside or outside, or both, of each finger insertion tong, or can be a closed loop ring 5 inside or outside, or both, of each finger insertion tong. Ring 5 can be a pre-formed closed loop ring, which can be an in situ formed ring 5, either formed by joining two linear strips 5*a* at respective end pairs, to form a closed loop when two laid parallel strips 5*a* are on a folded portion of a sheet of FDA approved and/or food service culinary customarily used material and the fold line is parallel to each strip, whereby folding over the intermediate fold line causes the one or more strips 5*a* to lay co-terminus on top of each other, where they are spot sealed or spot/beaded glued at each end to form a closed loop ring 5, or alternatively, ring 5 can be a prefabricated ring 5 which is inserted flattened into each tong pocket recess 2 and/or 3 and sealed or glued in location in situ at opposite ends thereof, within the respective pockets 2 and/or 3. Additionally, the elastic or stretchable member 5, in the form of one or more strips 5*a* or one or more rings 5, can extend the full width of the jaw tong pocket 2 or 3, or, as shown in FIG. 2, can extend partially within each jaw tong pocket recess 2 or 3. As also shown in FIG. 1, either the ring 5 or the strip 5*a* can extend partially across the recess pocket 2 or 3, or can extend the full width of recess pocket 2 or 3. For example, FIG. 1, while not being limited in scope, shows elastic or stretchable member 5 extending partially across the recess pocket 2, and shows elastic or stretchable member 5*a* extending the full width of recess pocket 3. It is assumed that the reverse can occur, where either recess pocket 2 or 3 can have one or more interior or exterior partially extending or full width elastic or stretchable members 5 or 5, either as one or more rings 5 or one or more strips 5*a*.

For sanitary reasons the flat folded sheet of coated paper has a release liner covering open regions 4 before use. Alternatively multiple elastic or stretchable straps may be used.

FIGS. 2A, 2B show strips 100 of tear-off tongs 101 (or cut into individual tongs) with smaller offset thumb accommodating portions 102, and a knife 110 and thumb forming region 103 associated with forming same. Although knife 110 is shown with a perforation gap, it can be a continuous edged knife without a gap. FIGS. 2C, 2D show strips 100*a* of tear-off tongs 104 with smaller centered thumb accommodating portions 105, and a knife 111 and thumb forming region 103*a* associated with forming same.

In one embodiment shown in FIG. 3, internal ring 5 is attached within each respective finger recess 2 and 3 to press against the finger while the tong goes from a flat pre-insertion state to an opened billowed state with a finger, thumb or fingers therein. Alternatively the elastic or stretchable member 5 or 5*a* may be an internal elastic or stretchable strap attached instead of a ring, either attached on the wall at two ends thereof, or sealed or beaded (glued) into the edge of the pocket Optionally a second ring or strap can be provided on the outside surface of each tong, for better stability of the tongs over the finger, thumb or fingers.

FIG. 3A shows an elastic or stretchable linear strip 5*a* cut from a roll 5*b* of elastic or stretchable FDA approved and/or food service culinary customarily used material, to be inserted or fabricated as one or more strips 5*a* on the inside or outside of each pocket 2 or 3 of the tongs 1 of FIG. 1.

Figure 4:
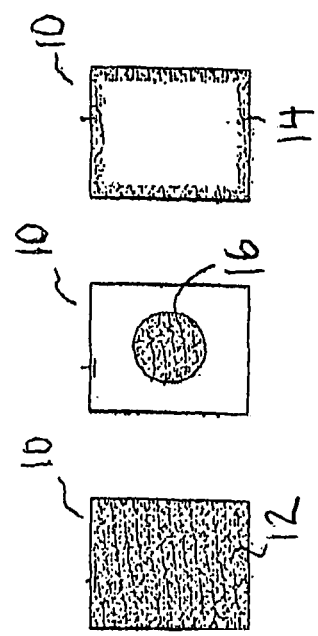
FIG. 4 shows a back elevation of a sticker with three variations of adhesive patch; full adhesive is shown in the left illustration, a central round patch is shown in the middle illustration, and a perimeter adhesive, seal or glue region is shown in the rightmost sticker illustration.

FIG. 4 shows a back elevation of a textured, food engaging sticker 16 with three variations of adhesive patch; full adhesive 12 is shown in the left illustration, a central round patch 16 is shown in the middle illustration, and a perimeter adhesive region 14 is shown in the rightmost sticker illustration. The advantage of central round patch of adhesive 16 is that it minimizes contact with paper finger recesses 2 and 3, so that free edges on the reverse food grabbing side can contact food without ripping the paper walls of finger recesses 2 and 3.

FIG. 5 shows an alternate sticker attached to an elastic or stretchable band 18 capable of attaching the sticker 10 to a finger recess 2 or 3 by the tensile force of the elastic or stretchable band 18. This embodiment can also be used without tongs, where the textured sticker is applied to a food grabbing side a finger while the elastic or stretchable band directly hold the textured sticker directly on the finger, wherein a disposable food grabbing accessory comprises a flexible substrate having a flat skin contact side and an opposite textured side. The flexible substrate is attached to an elastic or stretchable band placed over a finger, wherein the textured substrate is attachable by the tensile force of the elastic or stretchable band over the finger, so that the elastic or stretchable band directly holds the textured substrate directly on the finger, without any tongs.

FIG. 5A shows a flat plan view of an alternate embodiment for a ring structure 301 of FDA approved and/or food service culinary customarily used material with finger insertion openings 302, 303 where two rings 304, 305 with holes 304*a*, 305*a* are joined by a strip region 306 at a common edge 302, and have extending therefrom the textured finger grabbing portion, instead of a textured sticker 10 as in FIG. 5. Optionally, sleeve pockets 308 or one or more holding bands 309 can be added to the finger grabbing portion.

FIG. 5B shows a die cut hole 305*b* with contoured finger shapes 306*a*, 306*b*, 306*c* and 306*d* for holding one or more fingers shown in dashed phantom lines in crossection.

FIG. 5C shows ring hole cover 307 connected by perforatable attachments 308 connectable to, and releasable from ring 309.

Figure D is an alternate embodiment for ring hole 310 with serrated or otherwise undulating projections 311 to snugly grab a finger.

Figure E is a cushioned layer 312 for edge 313 of ring 14.

FIGS. 5F and 5G are perspective views of a single ring embodiment finger tool 301*a* with ring 301*b* with band 302 and base 303 for finger insertion therebetween. Ring 301*b* helps keep the finger tool 301*a* upon the user's finger without falling off.

FIG. 5H is an auxiliary textured tool 320, such as a cake frosting knife, attachable by an adhesive 321 below a release liner 322 to a bottom of base 303 of finger tool 301a. Finger tool 301a can handle or manipulate food or money in a sanitary manner.

FIG. 5I shows an optional second ring 301c to hold a distal end of a second finger for stability and strength.

Figure 6:
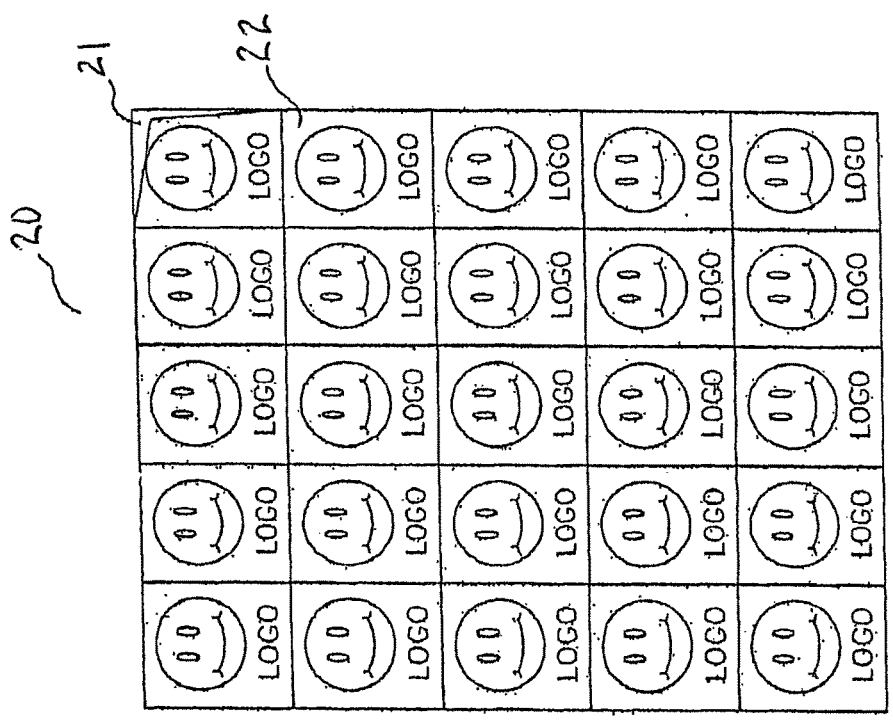
FIG. 6 is a top view of a sheet of kiss cut stickers with a fanciful indicia on a backing sheet for easy single peel-off.

FIG. 6 shows a sheet of kiss cut textured stickers 22 with a fanciful indicia on a backing sheet 21 for easy single peel-off before insertion on the food grabbing surfaces of finger recesses 2 and 3 of disposable paper tongs 1.

FIG. 7 shows a three-dimensional multi-layer sticker 24 with a C-side shape a set of overhanging immovable jaws and ridges on the top and bottom inner surfaces thereof for accepting an assembly 28 including a child's novelty toy 32 temporarily attached to top and bottom ridged blocks 29 which mate with those in the sticker 24. The toy 32 can also function as a shell cracker or meat tearer accessory for cracking shells of food products, such as shrimp or lobster. The toy/shell cracker can be a collectable item adorned with famous characters or other decorations, amusement or restaurant themes and/or sports logos. Finger grips 30 enable detachment of assembly 28 from sticker 24 by pressing finger grips 30 to release the tracks shown.

FIGS. 8 and 9 shows a novelty toy or shell cracker 38 with a press-in protrusion 40 or threaded protrusion 42 on its back, engageable with a textured sticker 36 having a female recess engageable with protrusions 40 or 42 before use, when novelty toy or shell cracker 38 is removed from textured sticker 36.

FIG. 10 shows screw-engagement protrusion 42 next to a flat sticker 36 with a central threaded hole.

FIG. 11 shows two deep stickers 35 and 36, one with a central recess 41 to engage a press-in toy/shell cracker 38 with press-in protrusion 40 and the second with a threaded central hole 43 to accept a threaded protrusion 42 on the toy/shell cracker 38.

Figure 12:
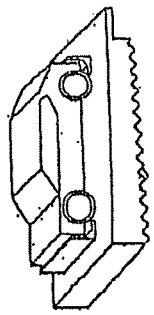
FIG. 12 is a perspective view of a car toy attached to sticker-attaching base.

FIG. 12 shows a car toy/shell cracker attached to sticker-attaching base.

Figure 13:
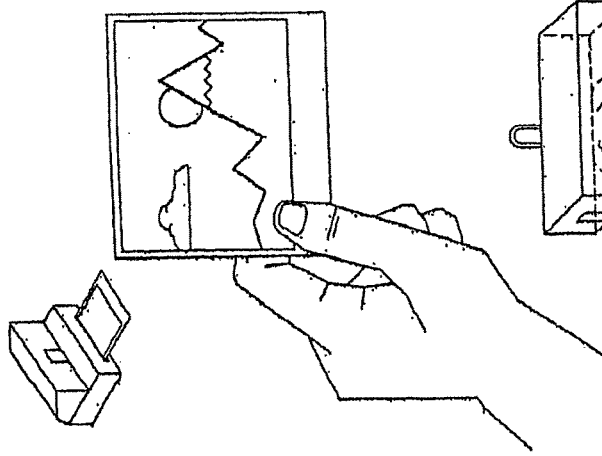
FIG. 13 is a perspective view showing a camera and a hand holding a snapshot created by the camera; this illustrates the option of creating custom art work for decorating a sticker surface.

FIG. 13 is a perspective view showing a camera and a hand holding a snapshot created by the camera; this illustrates the option of creating custom art work for decorating a textured sticker surface.

Figure 14:
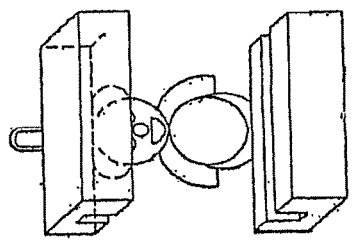
FIG. 14 shows a perspective view of a toy engaged with a sticker having grooves on the inside of top and bottom protrusions.

FIG. 14 shows a toy/shell cracker 38 engaged with a textured sticker having grooves on the inside of top and bottom protrusions thereof.

Figure 16:
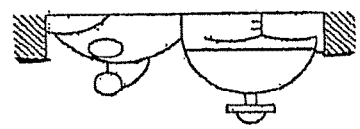
FIG. 16 is a side elevation of the toy and sticker of FIG. 15.
Figure 15:
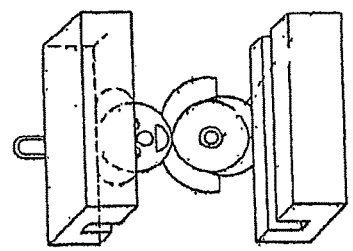
FIG. 15 is a perspective view of a toy with a locket and handle engaged with a grooved sticker.

FIGS. 15 and 16 shows a toy/shell cracker or accessory utensil with a locket and handle engaged with a grooved textured sticker. Optionally the toy/shell cracker/utensil bearing accessory can optionally extend forward with abrasive and/or protruding surface projections, so that it can also contact food, without being removed separately from the three dimensional texture bearing member.

Figure 17:
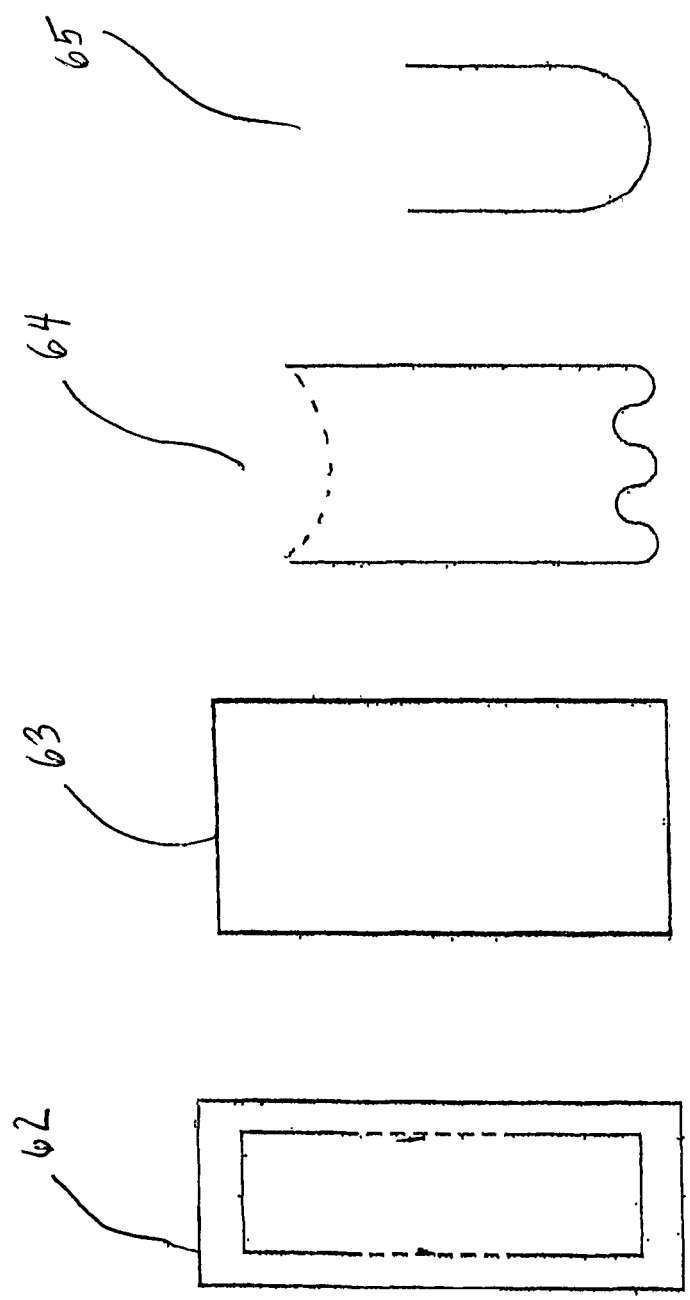
FIG. 17 is a plan illustration of four different heat sealers: double continuous sealer, rectangular sealer, wavy sealer, and semi-circular sealer.
Figures 17A, 17B, 17C, 17D:
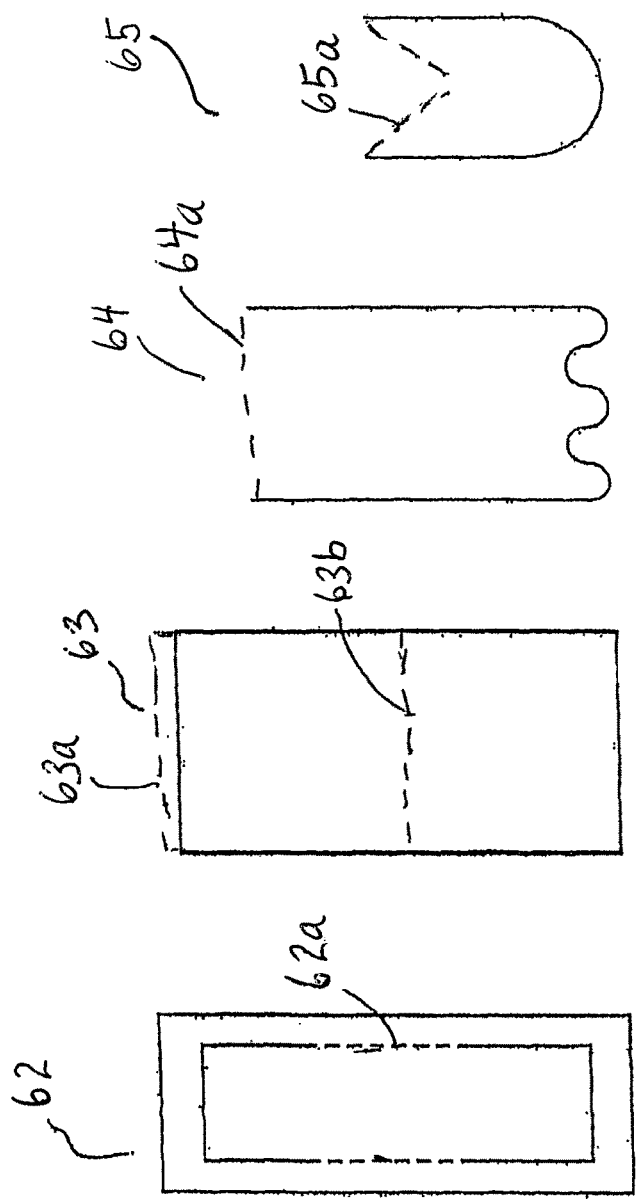
FIGS. 17A, 17B, 17C and 17D are plan illustrations of the four different heat sealers of FIG. 17 with dashed lines indication indentation lines used by the sealers for rendering bendable or tearable lines in the tongs being sealed by the heat sealers shown in FIG. 17.

FIG. 17 is a plan illustration of four different heat sealers: double continuous sealer 62 (or partial sealer), rectangular sealer 63, wavy sealer 64, and semi-circular sealer 65, which can optionally be a guided path for finger insertion, used to seal the edges of tongs 1 with various geometric shaped sealed edges (which can extend inside the pockets with perforated tearable seals) and optionally to also seal inside the finger insertion jaws of the set of tongs. Seals can be of any size or shape and can be double or multiple seals, to facilitate the tongs with a pair of pockets folding onto itself, to increase gripping edge area.

FIGS. 17A, 17B, 17C and 17D show the heat sealers of FIG. 17 with respective indentation lines 62a, 63a, 63b, 64a and 65a used by heat sealers 62, 63, 64 and 65 for rendering optional bending or tearing lines in or on the tongs 1 being sealed by heat sealers 62, 63, 64 and 65.

Figure 18:
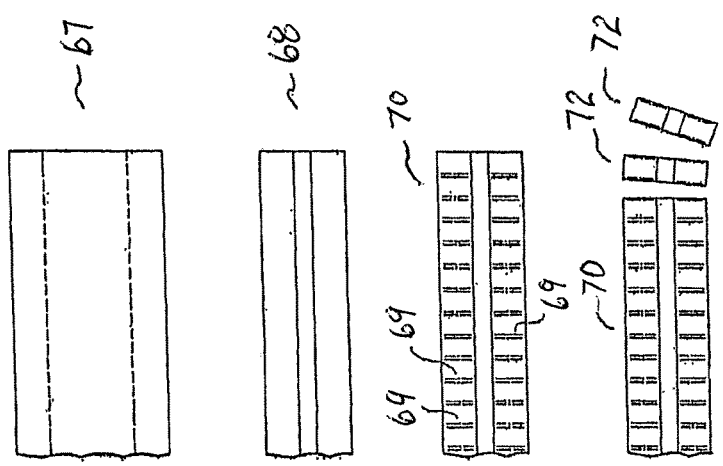
FIG. 18 is a progression of four plan images showing the prior art method of forming tongs by folding a flat sheet top and bottom toward the middle, heat sealing or adhesively bonding the fold-overs, and then cutting the individual tongs produced.

FIG. 18 is a progression of four plan images showing the method of forming tongs 1 by folding a flat sheet 67 at the top and bottom toward the middle to assume the configuration of folded sheet 68, heat sealing or adhesively bonding the fold-overs at areas 69 to form sheet 70 with multiple heat seals 69, etc., and then cutting sheet 70 into multiple individual tongs 72 produced, including optionally fully sealed with double perforations provided for open pockets of the multiple tongs 72 formed.

Figure 19A:
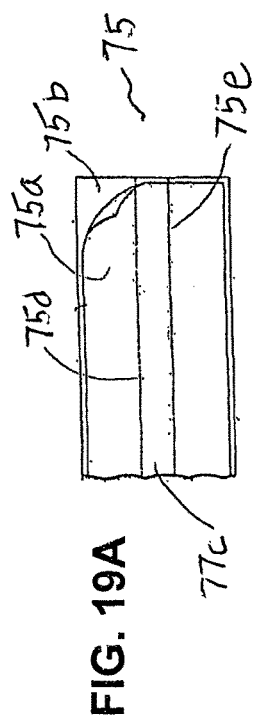
FIGS. 19A, 19B and 19C is a progression of three plan images of a two layer version starting with a flat coated sheet with pre-perforated top layer, heat sealing with optional draw string, and tearing at perforated regions to form individual tongs.
Figure 19B:
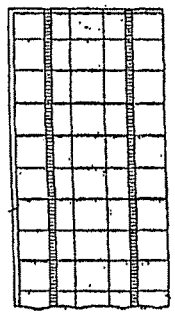
Figure 19C:
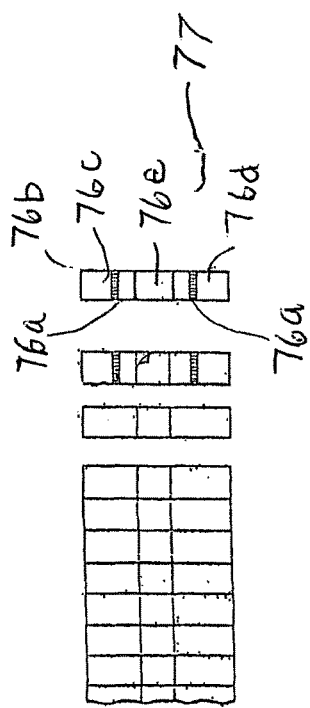

FIGS. 19A, 19B and 19C show a progression for a two sheet layer of forming tongs, with three plan images 19A, 19B and 19C starting with a flat coated sheet step 75 with pre-perforated top layer, heat sealing the paper at step 76 with optional draw string, and tearing sheet at step 77 at perforated regions to form individual tongs 76b. The tongs 76b are preferably pierceable at the opening mouth of the pockets of the jaws. FIGS. 19A, 19B and 19C show steps in making tongs 76b. FIG. 19A shows two layers of overlapping tong material 75a and 75b, of different gauges forming individual tongs 76b. For example, one layer 75a or 75b can be a thicker wall and the other layer can be a thinner, flexible wall, where the thicker wall 75a or 75b can press against the inserted fingers within tong finger insertion pockets 76c and 76d. Since the central tab 76e need be made of only one layer of material, a portion 77c of layer 75a can have edge perforations 75d and 75e, to remove layer 77c, leaving the remaining portion underneath of lower layer 76b as the material for central tab 76e of FIG. 19B.

Further with respect to FIGS. 19A, 19B and 19C, the layer 75a and mid portion 77c, are optional features. The tongs 76b can be made without the overlay layer 75a and mid portion 77c, so that the tongs are made with just the pockets 76c and 76d, connected by connecting central tab 76e.

In another option shown in FIGS. 19A, 19B and 19C, tongs 76b can have having finger stability straps 76a which are mounted against an inside wall of material of the finger accommodation pockets 76c and 76d, which are connected by central tab 76e. Optionally, finger stability straps 76a are attached by separate bead gluing spots, to allow for some unglued areas to stretch when the finger of the user is inserted in pocket 76c or 76d. The material of straps 76a is preferably bendable and flexible. While the straps are preferably made of an FDA approved or culinary standard material, in one option, since the inside of the jaws of the tongs do not touch food being held and manipulated on the outside of the tongs, the straps 76a can be partially or all made of other materials such as plastic or bendable metal.

FIGS. 19 D, 19E and 19F show an alternate embodiment where the tongs 209 are produced by only a single sheet of folded paper 201a, as opposed to the two paper sheet layers of FIGS. 19A, 19B and 19C. For example, optionally a one side edge of the strip forming tong 209 has side perforations 210 so that the tongs 209 are separable from an adjoining strip whereby a plurality of the strips are formed from a single sheet of disposable flexible FDA approved and/or food service culinary customarily used material 201a, the strips being separable by the perforations 210. The perforations at the top of 208a and 209a of tongs 209, when using a single foldable sheet 209a, should optionally be double perforation lines 202a, 203a and 204a, 205a, which will extend perpendicular to the axis of the aligned tongs 209, etc., and located parallel to and close to the pocket mouth of pockets 208a and 209a. The tong pockets 208a and 209a each are optionally sealed for sanitary purposes. When used, the perforations lines 202a, 203a and 204a, 205a, are pulled to reveal the open pockets 208a and 209a from under the sealed portion. The tongs 209 are also optionally pierceable by a finger(s) or thumb at the opening mouth of the pockets of the jaws to piece at least a portion of the pocket, to reveal at least a portion of the opening of the pockets 208a and/or 209a, whereby either the partially open opening hugs around the finger(s) or thumb, or if fully open, fully reveals the pocket interior of pockets 208a and/or 209a.

Figure 20:
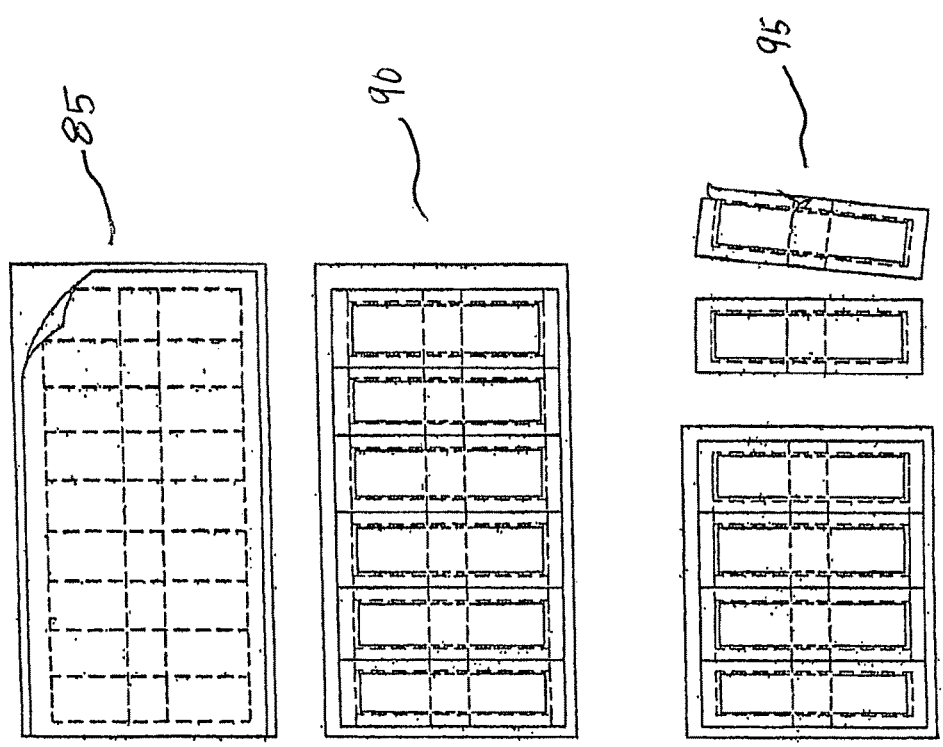
FIG. 20 is an alternate three step process (similar to that of FIG. 19) but producing tongs with border regions around each tongs to prevent choking of children.

FIG. 20 is an alternate three step process 85, 90, 95 (similar to that of FIG. 19) but producing tongs with border regions around each tongs to make tongs too wide for insertion into children's mouths, to prevent choking of children. It is noted that a peripheral region around the tongs shown in FIG. 20 can be torn away to make a smaller tong.

FIG. 20A shows a set of tongs 96 with pockets 96a and 96b separated by a central, tearable tab 97. The outer edges of the pocket 96a, 96b and the central tab 97 each have soft, irregular, tearable edges 98a, 98b, which such edges 98a, 98b are formed when the set of tongs 96 are being cut outside of edge seals 96c, 96d, forming extremely soft peaks 96e and valleys 96f. These extremely soft edges prevent paper cuts into the user's fingers, lips, mouth or tongue when holding food within tongs 96. The valleys 96f of the soft, irregular edges 98a, 98b provide notches for tearing the tongs when disposed into small pieces, as shown in FIG. 20E, where one pocket 99a with a food contact surface 99aa is placed with its food contact surface 99aa directly facing food contact surface 99bb of tong pocket 99b. In that way, the user's fingers are isolated from the messy food 99c of food contact surfaces 99aa and 99bb when the user makes an environmentally sound decision to tear tong pockets 99a and 99b, as well as to tear connecting tab 99d of the tongs 96 into small pieces, preventing wildlife from swallowing large pocket pieces after disposal.

FIG. 20F shows that, if both the front and back of pockets are messy, the clean central tab 99d can be used, and folded over the back and/or front of the messy pockets, thereby keeping the hands, fingers and/or thumb of the user clean during the tear down and disposable of the used set of tongs. In this manner, the hand that is using the torn tongs can press the user's thumb and fingers together, concealing the mess 99c on the front and back of the pockets. Then the hand that is not using the tongs can drag and fold the extended torn connecting tab 99d over the messy front or back of pockets, therefore concealing the mess 99c on the front or back of both pockets. With the same hand, the user can drag the set of tongs off the other hand and start the tearing down process to break the used set of tongs into small, disposable pieces.

FIGS. 20B and 20C show different embodiments for soft, irregular or serrated tearable edges 98a or 98b.

FIG. 20D shows tab 97 being torn at notch 97a from pockets 96a and 96b, each having soft, irregular tearable edges 98a, 98b.

Figure 21:
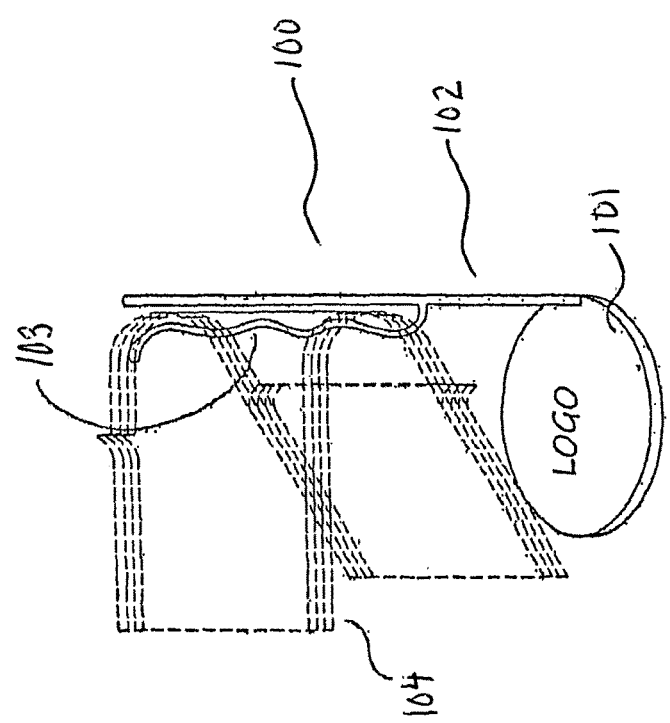
FIG. 21 is a perspective view of a stand with base, column, and clip to hold a supply of tongs on a tabletop.

FIG. 21 shows an alternate embodiment of a stand 100 with base 101, column 102, and clip 103 to hold a stacked supply of tongs 1 on a tabletop. Optionally the support member for the stacked supply of tongs can be a wall mounted hook.

FIG. 22 shows an alternate embodiment of a nested stack 105 of tongs of this invention having conical recesses for finger insertion, which may have a lid cap for the uppermost tongs of a stack of tongs.

FIG. 22A shows a sanitary lid for insertion over the top cap of a stack of tongs.

FIG. 23 shows a perspective view of tongs 107 with conical recesses having crimped facing food-contact areas 108 to provide a textured; linear region on food grabbing surfaces.

FIG. 24 is a perspective view of tongs 110 with truncated cone finger recesses with facing crimp seals 112 which form the food contact areas. While linear regions are shown, it is known that the sealed textured regions can be curved, patterned, crisscrossed or other geometric configuration.

FIG. 25 shows a flat cutout which can be formed to produce tongs 114 with conical finger recesses; two distal rectangular sections 115 connected by strap joint 116, each having a stripe of adhesive at one edge, are formed into the cones and tongs 105 or 107.

FIG. 26 shows tongs 114 made from the plan cutout of FIG. 25.

FIG. 27 shows a coated paper cone 118 and a conical heated mold 120 used to bond the cone 118.

Figure 28:
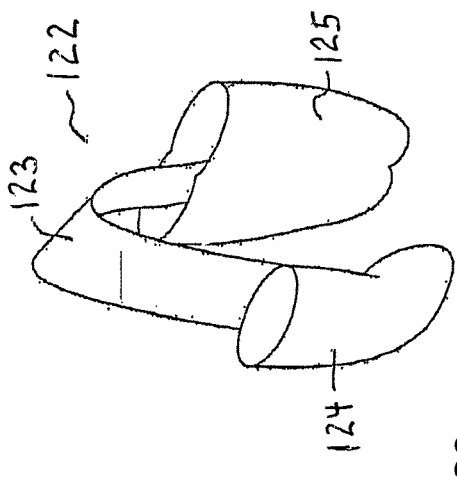
FIG. 28 is a perspective view of molded tongs with a shaped thumb recess and a two-finger recess attached by a strap section.

FIG. 28 shows a further alternate embodiment of molded tongs 122 with a shaped or crimped thumb recess 124 and a two-finger recess 125 attached by a strap section 123.

Figure 29:
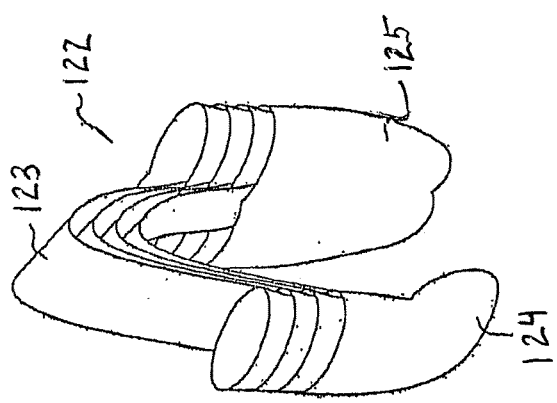
FIG. 29 is a perspective view of a nested stack of tongs of FIG. 28.

FIG. 29 shows a nested stack 122 of tongs of FIG. 28.

Figure 30:
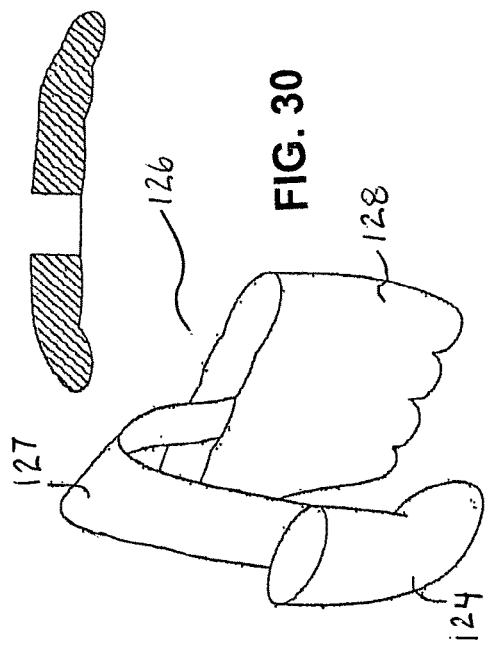
FIG. 30 is a perspective view of molded tongs with a shaped thumb recess and a four-finger recess attached by a central strap section.

FIG. 30 shows molded tongs 125 with a shaped or crimped thumb recess and a four-finger recess 128 attached by a central strap section 127.

Figure 31:
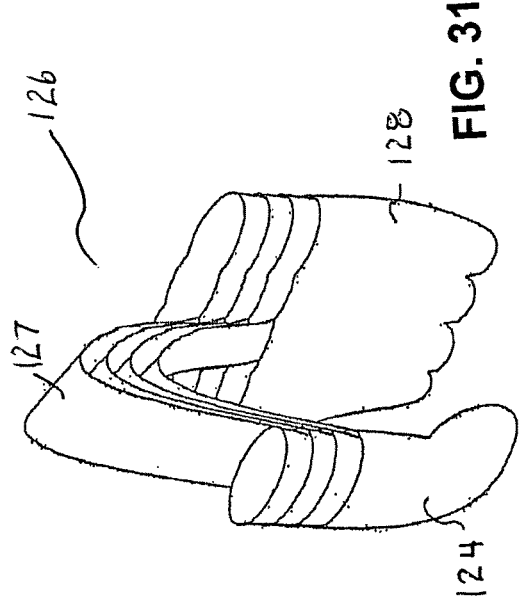
FIG. 31 is a perspective view of a nested stack of tongs of FIG. 30.

FIG. 31 shows a nested stack 126 of shaped and/or crimped tongs of FIG. 30.

Figure 32:
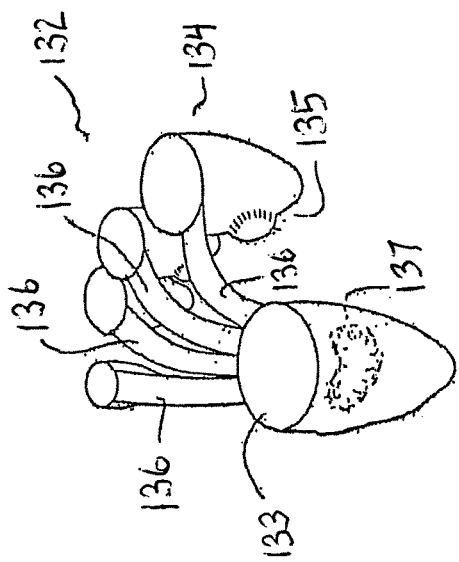
FIG. 32 is a perspective view of yet another embodiment of tongs of this invention comprised of a thumb recess attached to four separate size-appropriate finger recesses each attached to the thumb recess by a separate strap; each of the four finger recesses have protruding food-contact dimples facing the thumb recess which, in turn, has its own elongated protruding dimple (or four separate dimples) facing those of the finger recesses.

FIG. 32 is a perspective view of yet another embodiment of shaped or crimped tongs 132 of this invention comprised of a thumb recess 133 attached to four separate size-appropriate finger recesses 134 each attached to the thumb recess 133 by a separate strap 136; each of the four finger recesses 134 have protruding food-contact dimples 135 facing the thumb recess 133 which, in turn, has its own elongated protruding dimple 137 (or four separate dimples 135 of finger recesses 134) facing those of the finger recesses 134.

Figure 33:
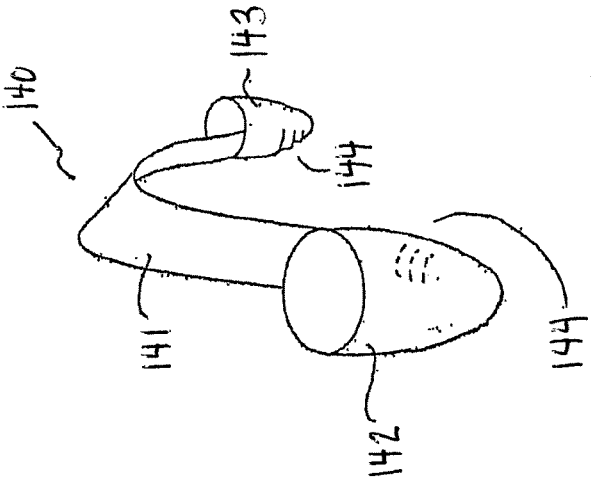
FIG. 33 is a perspective view of tongs with a thumb recess and a smaller finger recess attached by a strap section with facing side food-contact crimped patterns on the two recess sections.

FIG. 33 shows tongs 140 with a thumb recess 142 and a smaller finger recess 143 attached by a strap section 141 with facing side food-contact crimped patterns 144 on the two recess sections.

Figure 34:
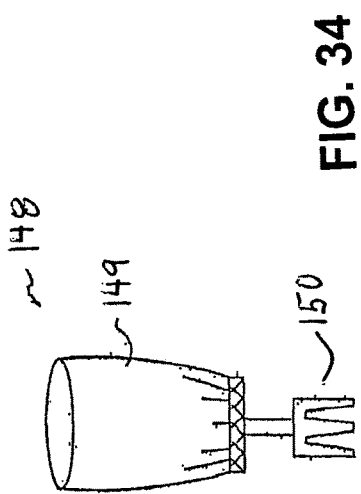
FIG. 34 is perspective view of a food handling accessory with a hand recess attached to a rigid food-contact tool such as the fork illustrated.

FIG. 34 shows an alternate embodiment a food handling accessory 148 with a hand recess 149 attached to a rigid food-contact tool 150 such as the fork illustrated, or other food handling implements, such as knives, spoons or chop sticks.

Figure 35:
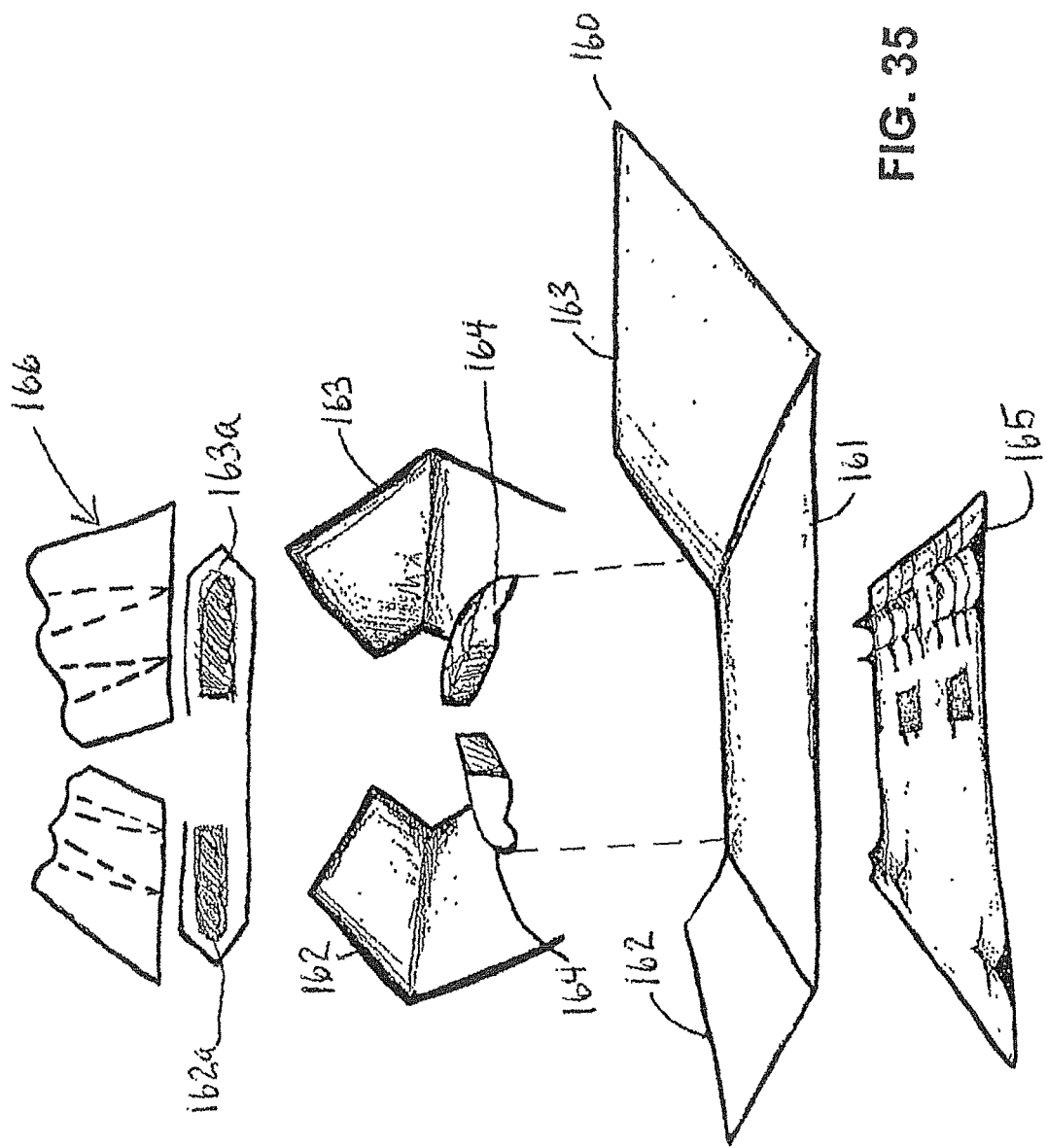
FIG. 35 is an exploded diagrammatic view of the steps used in forming disposable flexible plastic or reinforced paper tongs with textured surfaces.

FIG. 35 shows disposable finger holding tongs for handling a food product including a sheet 160 of disposable flexible coated plastic, plastic or fabric FDA approved and/or food service culinary customarily used material, or combinations thereof, such as, for example, MYLAR®, or reinforced paper FDA approved and/or food service culinary customarily used material, having a central folded region 161 with opposite foldable distal end wings 162, 163. The distal end wings 162, 163 of the strip 160 form open jaws of the tongs wherein each folded distal end wing 162 and 163 forms a pocket 162a or 163a to accommodate a thumb or at least one finger of a person using the tongs to hold food. A removable seal covers at least the central region of the openings of the disposable finger tongs (or the entire tongs) prior to use. Respective textured surfaces are provided on grabbing surfaces of the jaws to assist in holding the food product; wherein the tongs are formed from the folded sheet 160 of flexible FDA approved and/or food service culinary customarily used material folded over a set of female dies 164 pressed by a male die 165 to form crimped open three dimensional finger and thumb portions with textured surfaces, such as those shown in FIGS. 28-31 or FIGS. 32 and 33. The folded FDA approved and/or food service culinary customarily used materials and the complementary dies 164 and 165 are provided under a shroud 166 providing a heat sealing of the tongs.

FIGS. 36-61 show further alternate embodiments for the food handling tongs.

For example, in addition to the pockets 2, 3 shown in FIGS. 1 and 2, the pocket 308 shown in FIGS. 5A and 5F, other finger accommodating areas include the internally extending straps 5a of FIG. 1 or the strap 309 of FIG. 5A (which may be flexible and stretchable, or just flexible), other finger accommodating areas are shown in the following drawing FIGS. 36-61.

Figure 36:
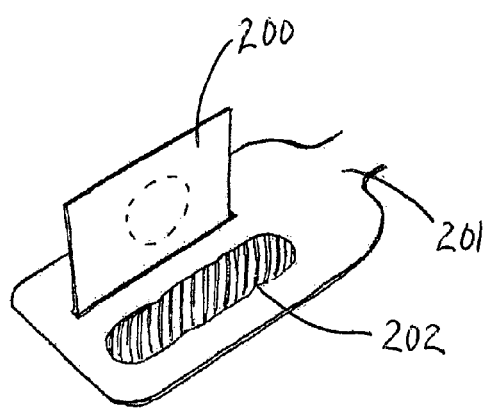
FIG. 36 is a detailed view of a tab connecting two finger accommodating areas of a pair of tongs, where the tab has a vertical wall to rest fingers against.
Figure 37:
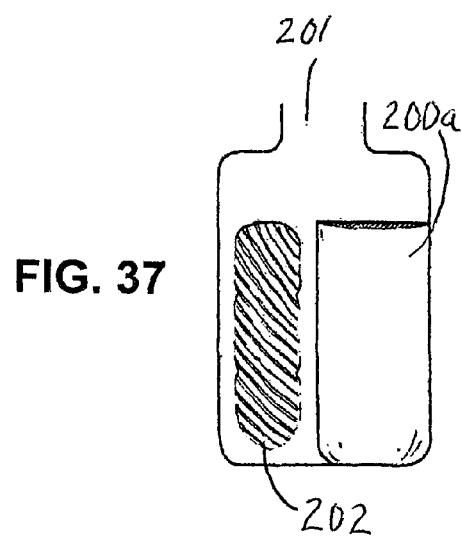
FIG. 37 is a detailed view of a tab connecting two finger accommodating areas of a pair of tongs, where the tab has a vertical wall to rest fingers against and a tubular insertable area.
Figure 38:
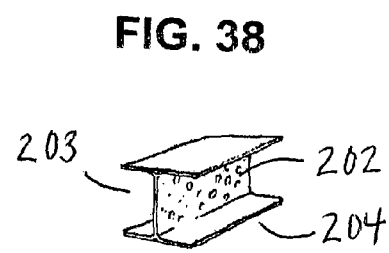
FIG. 38 is a detail view of a tab with an I-beam connection.

As shown in FIGS. 36-38, the two jaws 2, 3 of the tongs can be connected by a tab 201, wherein the in-between finger(s) tab can be at least one vertical tab 200, with or without dimple areas or can be have textured surface region 202 instead and/or a combination thereof. These areas can also be at least in combination and/or an extension of a finger accommodating pocket 200a, as shown in FIG. 37, and/or strap area, and/or having I beam and/or vertical wall tab shape.

For example, as shown in FIG. 38, the in-between finger(s) tab 200 can be at least one I-beam structure 203 with or without a textured region 202, dimples, etc., on the finger touching sides. The tab 200 can optionally have an adhesive 204 with a peelable cover, to secure an accessory 38 (shown in FIG. 8) and/or be provided on the accommodation side(s).

Figure 40A:
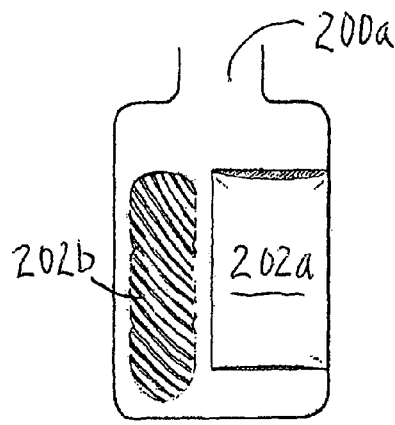
FIG. 40a is a detail view of a set of tongs with a textured area and a pocket.
Figure 40:
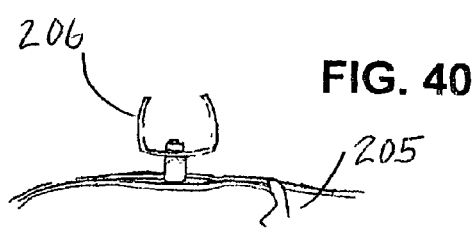
FIG. 40 is a detail view of an accessory accommodating post on a tab of a set of tongs.
Figure 39:
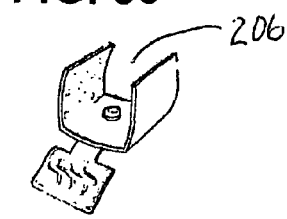
FIG. 39 is a detail view of a finger rest area of a tab of the set of tongs.

As shown in FIGS. 39 and 40, the in-between free finger tab accommodating area connected to pocket 205, shown in FIG. 40, for at least one utensil support cradle area 206, such as the U-shaped cradle 206 shown in FIG. 39, to hold utensils, such as chopsticks or light plastic utensils. The U-shaped cradle can be attached by an adhesive tab to the tongs, or can be sealed to the tongs.

FIG. 40a is a close up detail view of a tab 200a showing a finger pocket 202a or a dimpled, textured finger rest area 202b.

Figure 41:
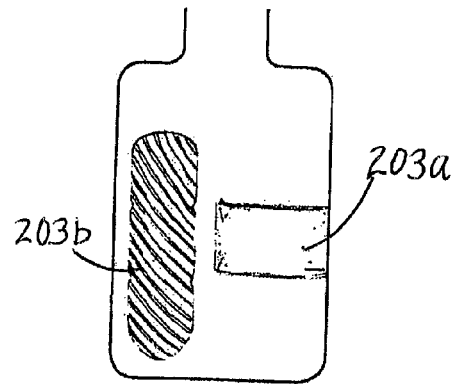
FIG. 41 is a detail view of a set of tongs with a textured area and a strap.

As shown in FIG. 41, instead of having pocket 202a, the in-between free finger tab accommodating area can be a strap(s) 203a for at least one finger/thumb and at least one free finger rest area 203b.

It is further noted that the in-between free finger tab accommodating area versions of FIGS. 40a and 41 can have similar suitable areas 203a, 203b for thumb accommodation.

Figure 42:
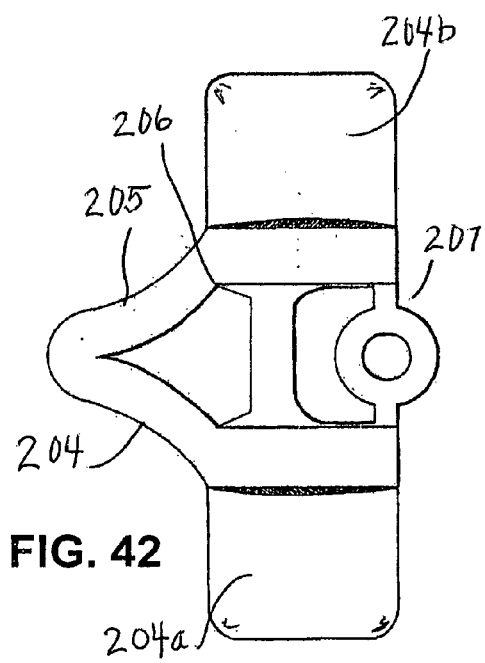
FIG. 42 is a front view of a set of tongs with multiple connector tabs.

FIG. 42 shows a set of tongs 204 having finger accommodating pockets 204a, 204b (which can alternatively be straps, like straps 203a of FIG. 41), wherein pockets 204a, 204b are connected by one or more connecting tabs, such as tab 205 extending outside of the user's palm contact area, width allowance or width adjustable tabs 206 or stretchable tabs 207.

Figure 43:
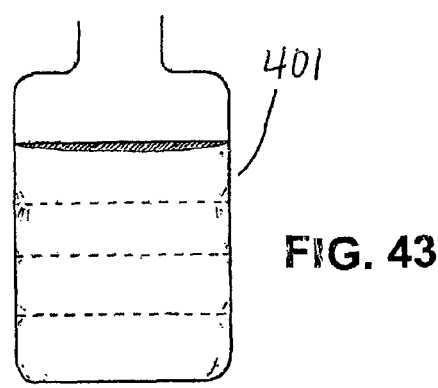
FIG. 43 is a detail view of a jaw of a set of tongs with double sided pockets.

FIG. 43 shows one jaw 401 of tongs with pockets 402, 402a on both sides of jaw 401. Pockets 402, 402a can also be replaced by straps, like straps 203a shown in FIG. 41.

The jaws of the tongs can have free finger accommodation "I beam" shaped tab 203 of FIG. 38 and/or other mentioned finger accommodation methods on at least on one side. For example, the jaws of the tongs can also can have a features of recessed dimples and/or textured surfaces 202 being the finger accommodation areas, or, as shown in FIG. 5A, can be in combination with at least one finger stability hole 208 on the tab connecting the jaws of the tongs, and optionally, when separated, can be used as a single individual finger jaw, such as shown, for example, in Figures 5F, 5G, 5H and 5I.

Figure 44:
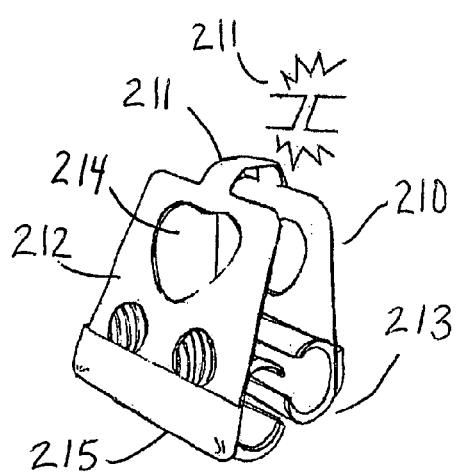
FIG. 44 is a perspective view of a set of tongs with a breakaway feature.

As shown in FIG. 44, a user can optionally twist or break at least one bendable connecting perforated line 211 on the jaws 210 to break the jaws into two pieces 212, 213, in which each piece 212 or 213 can be used separately, wherein a user takes one piece and inserts at least one finger/thumb into a stability hole 214 and then into finger accommodating area 215.

The inside or outside object/food touching side of each of the jaws of the set of tongs can be in combination so that the entire jaws are configured to be a theme, or to depict a character, person, place, thing, animal, sports, tool, etc., wherein the tabs in-between the finger accommodation areas can be of different size/shapes of each other.

These jaws 210 can be molded, injected, stamped, punched, formed, etc., so that the object/food touching side can be shapes and/or functioning tool, utensils, crushers, meat tearers, etc. (as shown in FIGS. 7, 8, 9, 12), or can be an combination of other jaws. For example, when the set of tongs are used on fingers of the user, the thumb side can have clamp like jaw and the finger side jaw (or vice versa) can have textures and a bird beak shaped jaw for dissecting food into small pieces. Optionally this can also apply to individual fingers using independently and/or independently used jaws can be made and presented separately. Also, the respective jaws of the set of tongs can be presented to interact with each other. For example one finger/thumb can have a particular fanciful shape, print, logo, etc., such as a fanciful depiction of a shark's upper jaw teeth and another finger/thumb has the features of the lower jaw teeth, so when they combine they mimic a shark taking a bite.

The tabs connecting both finger(s) or thumb accommodating areas, such as, for example, the closed ended pockets 2, 3 as in FIGS. 1, 2, pocket 308 of FIG. 5A, and pocket 204a, 204b of FIG. 42, are connected by tabs, such as tab 205 of FIG. 42, can have many different configurations.

Figure 45:
FIGS. 45-49 are close up views of various connector tabs to accommodate various sized fingers.

The universal entrance wide open connecting tab 220 of FIG. 45 can optionally be out the palm area of the set of tongs, which allows the finger accommodating areas to be accessibly by multiple size users and allows the two free swinging finger accommodating areas connected by tab 220 to perform at their maximum for including an user with large or extra large hands and fingers. As shown, tab 220 extends out of the palm area, similar to tab 307 of tongs 301 of FIG. 5A. Tab 220 has a single peak 220a in the middle of tab 220.

Figure 46:

As shown in FIG. 46, a universal entrance extra wide open connecting tab 222 can optionally be out the tongs which thereby allows the finger accommodating areas to be accessibly by users with different fingers of multiple sizes and allows the free swinging finger accommodating area (such as pockets 2, 3 of FIG. 1, pockets 308 of tongs 301 of FIG. 5A), and the tab area 222 to perform its maximum for including the user with large or extra large hands and fingers, whose fingers can be larger. To make tab 222 extra wide, as in FIG. 46, it may be constructed of a plurality of peaks 222a, 222b extending out of the palm area of the tongs.

Figure 47:
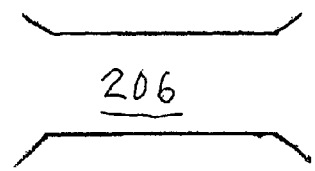

Width and stable allowance tabs 206 of FIG. 47 can have changeable and functional FDA approved and/or food service culinary customarily used material characteristics, such as stretchability, ventability and the capacity to return to an original state even if subject to stress, such as being pulled apart widely or having a full contents. Before the alteration of the width, the two ends of tab 206 are the same as a hardy accommodation connector, wherein both ends perform the same function of width and stability for a particular size allowance usage, when the state of the FDA approved and/or food service culinary customarily used material subject to stress, such as being able to return to its original state. The FDA approved and/or food service culinary customarily used material can also have FDA approved and/or food service culinary customarily used material splits, resulting in a desired ventilation ability, which can be presented and altered characteristics of stretchability can be provided as desired.

The set of tongs, with a tab of FIG. 47 connecting finger insertion portions (i.e. pockets, finger accommodating straps and/or finger stability insertion holes, can all be provided with straight edges. Optionally, the set of tongs, with the tab connecting finger insertion portions can also be optionally provided with injury prevention edges on all or part of the set of tongs, where the tab and pockets do not have sharp paper edges, which can cause paper cuts not only to the user's finger's, but, more importantly, to the sensitive mouth and lip area of the user's face, which can also be subject to paper cuts. To solve this potential injury producing result, the exposed edges of the tab and pockets can be provided with non-sharp edges, such as being soft serrated, ruffled, rounded edged, radially ribbed, deckled and/or soft blunted, to prevent paper cuts to the user's sensitive finger skin and sensitive face area. It is also noted that these injury preventive features can be optionally included on any edges of any of the embodiments of the present invention, where the one or more tabs allow for a continuous connection between the two opposite finger accommodating areas.

The tab 206 can extend in or out of the finger accommodation area, but optionally which allows for a continuous use of the tongs for a particular size of a customer user, without the disadvantages of being torn and/or stressed with a clumsy fit by the user's hands, and avoids being an unstable, unsuitable fit for another sized user with different sized fingers and hands. The tab 206, whether or not it has the aforementioned changeable and functional FDA approved and/or food service culinary customarily used material characteristics, can optionally have at least one central ventilation hole or stretchable holes, or both, or an area with a hardier finger/thumb accommodation that is connectable and that is less resilient than its other family member, but with more resilience than its other personality, yet having a less hardy connectability than the other personality. The other changeable material characteristics of the tongs' material can be at least one of the changeable characteristics, for example ventilation ability because when the altered embodiment is presented, it physically and literally weakens the strength of the other personality of the material.

Figure 48:
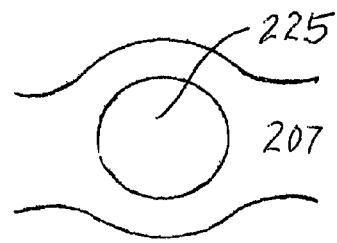

FIG. 48 describes a stretch tab 207, having at least one hole 225 in the connecting tab 207 and/or finger accommodating area. This hole 225 allows the jaws of the set of tongs to stretch out further from each other, for users with larger hands and to grip larger items of food. Optionally, a plurality of eye holes 225 can be of different height, width, circumference of each other and of the rest of the tab. Eye holes 225 can be any size, shape, length, pattern, or fanciful outline shape of a character, people, places, things, etc. All tabs 207 can be in and/or out of the palm and/or accommodating area of the tongs, or in or out of the top edges of the palm, out of pocket area, top and inner pocket area and/or lower in/out, and/or central area and/or entire in-between area of the tongs.

Figure 49:
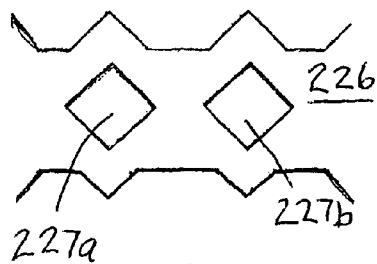

As shown in FIG. 49, a super stretch connecting tab 226 includes a plurality of holes 227a, 227b in the body of the connecting tab 226 and/or finger accommodating area of the tongs. These holes 227a, 227b allow the jaws of the set of tongs to stretch out even further from each other. Eye holes 227a, 227b can be of a different height, width and circumference of each other and of the rest of the tab 226. Eye holes 227a and 227b can be cut of any size, shape, length, pattern, character or design, such as in the outline form a person, place, thing, etc.

All tabs noted above in FIGS. 45-48 can be in and/or out of the palm and/or accommodating area of the set of tongs, and in or out of the top edges of the palm area of the wearer, out of the pocket area of the tongs, or in or out of the top and inner pocket areas and/or lower in/out, and/or central and/or entire in-between areas of the tongs.

As shown in FIG. 50, tabs can have a crisscross shape, with crossing straps 228a, 228b, in a stability allowance tab 228 for particular sized user, wherein this tab 228 of the crisscross configuration provides for sturdy connection to the finger accommodating areas at opposite ends of crisscross tab 228, while having large ventilation areas to prevent sweating when in prolonged use and to allow a width allowance to accommodate different sized fingers of a user. Venting areas 229a, 22b, 229c and 229d between the crossing straps 228a, 228b allow for ventilation and adaptable hand motions.

Figure 51:
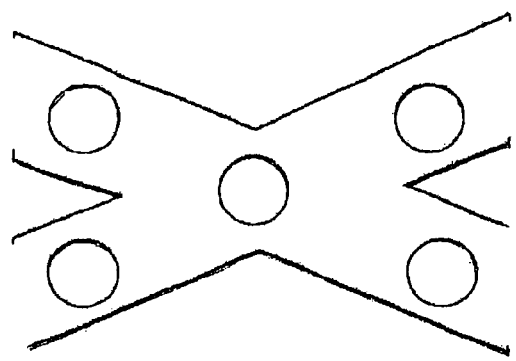

As shown in FIG. 51, tabs 230 are crisscross stretch tabs for multiple uses, which can be partially stretchable at opposite ends of tab 230, with extra stretch and super stretch capabilities, where this tab 230 allows for sturdy connection to finger accommodating areas of the respective jaws, while having large ventilation areas 231a, 231b, 231c and 231d adjacent to crisscrossing straps 232a, 232b, to prevent sweating when in prolong use and allow a width allowance for a user. Holes 233 further enhance the stretchability of crisscrossed tab 230.

As shown in FIG. 52, the tongs may be separated by tearable perforations into two separate finger accommodating tongs (such as also shown in FIGS. 5F, 5G, 5H and SI). The perforated tearable tab 235 allows the tong to have an individual usability to accommodate individual fingers/thumb so that these perforated portions 235a, 235 can be at least one perforated and made to be easily torn apart along perforation line 236. Optionally, tear-apart tab portions 235a, 235b can be stretched by presenting larger spaces in between perforated areas 235a, 235b. This version can have stability holes, in which when being used individually the user insert at least one thumb/finger through stability hole(s) 208 for finger insertion, before subsequent finger insertion into pockets or straps, in each finger accommodating area.

Figure 53:
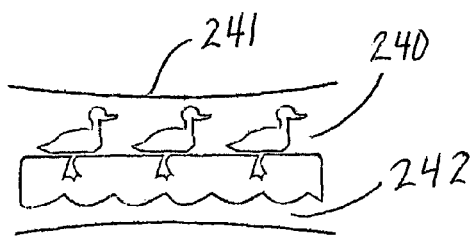
FIG. 53 is a close-up detail view of a connector tab with theme features.
Figure 53A:
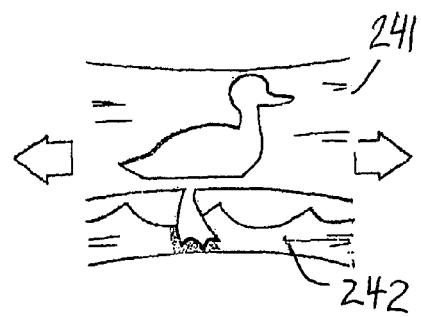
FIG. 53A is a close-up detail view of the connector tab of FIG. 53, showing the elements of FIG. 53 converging upon each other.

As shown in FIGS. 53 and 53A, tabs can be theme tabs 240, which can be stretchable, having decorative themes formed by cutouts and interconnecting protrusions, where at least a portion 241 of the tab 240 interacts with another portion 242 for example by having a theme at the upper portion of the tab 240 with a die-cut of any length or shape and the lower or opposing side of the tab has another theme die-cut. When tab 240 is used, stretched, for example the lower portion 242 interacts with the upper portion 241, and the die-cut portion allows the entire tab to stretch out further. For example, the lower portion 242 of the tab 240 can be die cut with each hole representing a pond with ripples of water around a hole, and the upper part 241 of the tong is die cut with a fish facing down or up so when the tab is stretched out, the upper portion 241 will fold onto the lower portion 242, therefore, the theme of tab 240 can be the fish diving out of or into water. FIG. 53A shows elements 241 and 242 converging on each other to form a subsequent image of the fish in the water. Tab 240 can also be a net. It is known that such a theme can be part of a sporting events, story, book, movie, an interaction with, etc. Another example of a theme can be that the entire apparatus is a continuous wing and/or wings with at least an optional central connection, such as in-between wings connectors and/or out of wings area connectors where the wing connectors are reciprocating, like upper portion 241 and lower portions 242 of tab 240. This apparatus can be presented along with a theme of being on and/or part of an animal, human, place, thing, etc.

Figure 54:
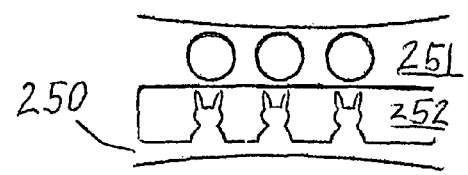
FIG. 54 is a detail view of a connector tab with game features.
Figure 54A:
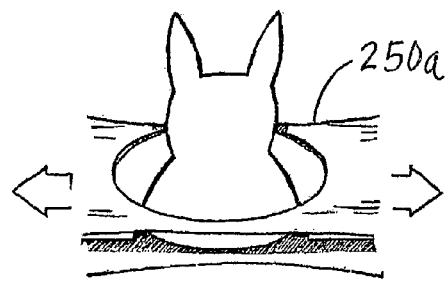
FIG. 54A is a close-up detail view of another connector tab with game features.
Figure 54B:
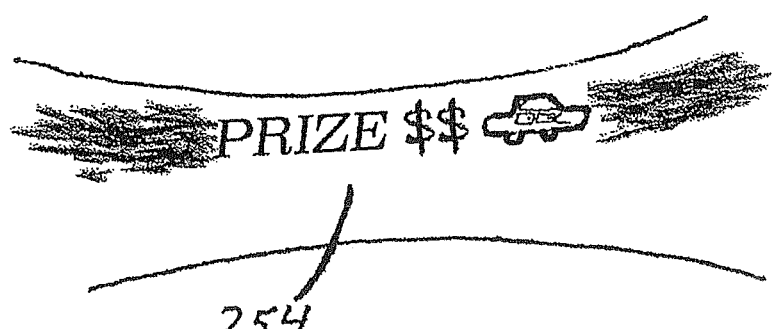
FIG. 54B is a close-up detail view of another connector tab with scratch-off lottery prize features.

As shown in FIG. 54 and FIG. 54A, a game tab 250 or 250a, can be, for example, formed with the upper portion 251 of the tab has eye holes with a target/bull's eye and the bottom portion 252 can have die-cut shapes such as arrows, which, when the tong is stretched, it will fold in on itself. Therefore an arrow shape can strategically be inserted into the target/bull's eye, which is equivalent to a game's point and/or a missing part, which can be filled by another portion to make those portions one which can be the answer to a question. Also, as shown in FIG. 54B, any connecting tab can alternately have scratch-off lottery type features 254 to form a lottery ticket. FIG. 54A is a close-up detail view showing another connector tab 250a with game features.

Figure 55:
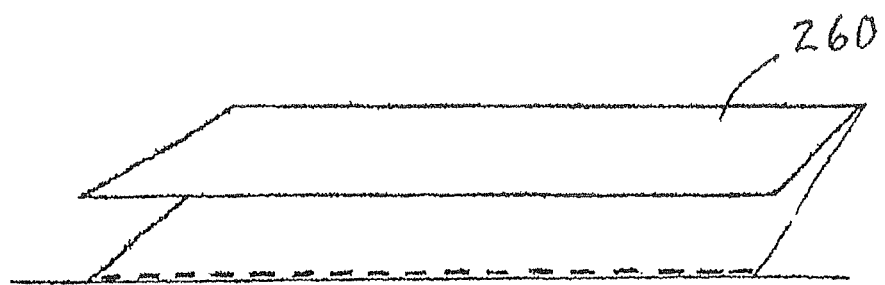
FIG. 55 is a detail view of a napkin detachably connected to a set of tongs.

As shown in FIG. 55, tongs can be manufactured in combination with a napkin 260. To make tongs with napkins 260, a prepared piece of FDA approved and/or food service culinary customarily used material is perforated and/or cut into shapes, then worked (glued) and/or ready to be sealed, folded and the perforated napkin attachment can be folded at the same time. This attached napkin version can be partial and/or around the entire tong, much like the child-proof version. The napkin can be folded as many times as desired, or in a pattern. The entire combination tongs and napkin 260 can be folded to accommodate an individual sample package. The napkin can be made to be optionally tearable. Another method is for example the tearable napkin is only on one side of tong, instead of partial or all around. A bottom sheet or roll of FDA approved and/or food service culinary customarily used material is pre worked with a line of perforations separating the tong and napkin 260, pre-glued and/or ready to be sealed, then another sheet or roll the width of the tong is pre worked with perforations which is then laid on top of the pre worked bottom FDA approved and/or food service culinary customarily used material so that when they come together, there is provided a finished item it can be folded to accommodate packaging. To use, the user unfolds, then tears, the connecting perforation in-between the pockets of the tongs to reveal the pocket's respective mouths, although the user can pierce the user's finger/thumb through the connecting perforation at the pockets mouth therefore making a huggable pocket. The user can also tear away the perforated connected napkin 260 to use it as a napkin.

As noted before with respect to FIG. 44, a perforated bendable tab 210 can be scored and/or with less space in between the perforations, which allows the tab 210 to be bendable while still having integrity connection which can perform more vigorous clamping work, or, as shown in FIG. 44, the two jaws 42 can be separated into single finger pockets, such as shown in FIGS. 5F, 5G, 5H and 5I. The jaws of FIG. 44 can be either disposable, or if made of plastic, reusable.

As shown in FIG. 56, an ergonomic tab 270 version allows for an off centered fold in the tab area and this off centered fold allows the hand of the user to do less work by allowing the natural shorter thumb into a short distance moving thumb accommodating area, and a longer finger(s) area to easily function in a more distal finger accommodating area. In this version of tab 270, the tab fold line 271 divides the tab 270 into two unequal length sections.

As shown in FIG. 57, a slit/cut stretch tab 280 can have slits/cuts at any angles and/or directions. Also, a slit 281 can be part of another slit in another direction. This also allow for expandability while still having enough protective FDA approved and/or food service culinary customarily used material to protect hands from getting soiled while using the set of tongs with slit tabs 280.

Figure 58:
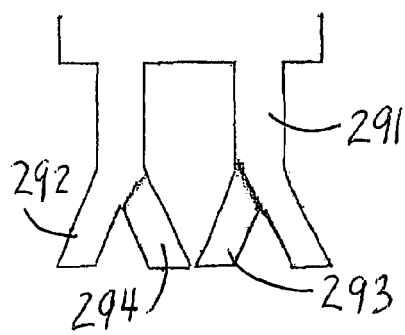
FIG. 58 is a detail view of a connector tab with tear allowance, auxiliary connectors.

As shown in FIG. 58, a tear resistant tab 290 can prevent a tear from traveling because individual finger accommodating area connectors 291, 292 are connected separately side by side from each other, with extra auxiliary connectors 293, 294, so if a stress tear starts on one of the connectors 291 or 292 and rips through fully, there will always be another auxiliary tab 293 or 294 to maintain the integrity of the connection of the jaws of the set of tongs.

Figure 59:
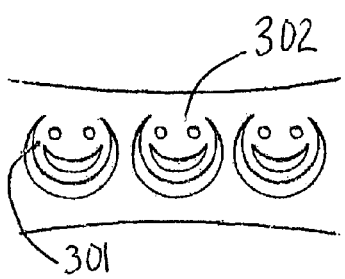
FIG. 59 is a detail view of a tab with movable puppet features.

FIG. 59 shows that a tab 300 can be a puppet tab, wherein die-cut images are not fully cut out, leaving the uncut images 301, 302, etc., still on the tab, so when the tab 300 is stretched or in use, the uncut images 301, 302, etc., become movable. These images 301, 302, etc., can be printed and/or die-cut.

As shown in FIG. 60 and FIG. 61 all versions of tongs can accommodate a clip 350 with a hook 352, in which the hook 352 secures itself to the tong and the hook 352 secures itself on the user's hand/fingers. In FIG. 61, the hook 353 can be extended to form a half ring.

As noted above and as shown in FIGS. 18, 19A-19F and 20, multiple tongs can be made from a single sheet of paper and cut to separate each tong.

All cuts and/or peripheral edges or at least a portion of tongs can optionally have soft, less sharp frayed, zig-zag, uneven, fragmented, torn edges, perforated edges, segmented, straight, ragged, teeth, rounded teeth, ripped, burst, serrated, jaggered, other methods known in the arts, also to include reference to serrated edges of botany plants and leaves for edge configurations. This is to prevent sharp edges when necessary to prevent the user from getting injuries such as paper cuts, it is already known that when materials such as paper brazes, rubs against the skin is can cause painful cuts, so there is an urgent need for the mentioned prevention. Methods such as providing soft, feathered deckled, deckling edges and/or mechanical deckling edges, will accomplish frayed, uneven fragmented, torn, jaggered, zig-zag, etc., edges, whereas known methods in industries such as bindery, steel rule die cutting and such will accomplish straight, segmented, perforated, teeth, straight teeth, rounded teeth, serrated, rip, cross-cut, angled teeth, etc., edges in which all methods can be a whole. The irregular, non-smooth sealed edges around the set of tongs, with soft, injury preventive edges with irregular free ends extend beyond a seal parallel to, and in the vicinity of a periphery of a finger(s)/thumb insertion pocket or strap of a set of tongs, to promote tearing.

These soft, injury preventive edges can be formed by folding edges, such as shown in FIGS. 19A, 19B, 19C with two layers, or by folding single sheets of paper forming tongs as in FIGS. 19D, 19E and 19F. To accomplish the soft edges, the folded edges are folded and sealed, but with a peripheral edge extending beyond the seal, formed of two unbonded edges adjacent to each other, but with soft fringed, deckled, serrated or otherwise cut edges that prevent cuts to the fingers, lips or tongue of the user of the tongs. The inner sides of these dual unbonded edges can be adorned with indicia, such as images or words.

From a single sheet of coated uncoated, textured, layered FDA approved and/or food service culinary customarily used material, a stability wall is provided by prepping FDA approved and/or food service culinary customarily used material to accommodate a flexible strip which is bead glued or bead sealed onto the single sheet of FDA approved and/or food service culinary customarily used material.

Then the single sheet of FDA approved and/or food service culinary customarily used material is folded to make pockets. Now there is a pocket with a stability wall from single sheet. Although other described methods can apply.

Full stability walls are accomplished by presenting two sheets or rolls of FDA approved and/or food service culinary customarily used material, prepping, working them it to accommodate each other than the FDA approved and/or food service culinary customarily used materials of a different gauge, to adhere or seal itself onto each other, which is each a different FDA approved and/or food service culinary customarily used material. When the tongs are cut, stability walls are presented of at least one full different wall of different gauge FDA approved and/or food service culinary customarily used materials, then prepping it to accommodate each other the FDA approved and/or food service culinary customarily used materials of a different gauge, to adhere or seal itself onto each other's respective FDA approved and/or food service culinary customarily used materials. When the tongs are cut, stability walls are presented of at least one different wall FDA approved and/or food service culinary customarily used material, with at least one wall in the tongs.

As noted before, the tongs of the present invention optionally includes finger stability elements, to help keep the jaws of the tongs on the thumb, finger or fingers inserted in the respective jaws. These include additional holes in the connecting tab, as in FIG. 5A, or one or more flexible straps attached to the respective wall of the respective jaws of the tongs, as shown in FIGS. 19A, 19B and 19C herein.

Another finger stability element can be a pierceable seal in a pocket. A heat sealer and/or glue can make channels in the pocket, angled, straight or perforated inside the pocket, so a user inserts a finger into the pocket then follows through a channel, thereby bursting the seal on either sides of finger/thumb, which will allow the pocket to hug around the finger.

The pierceable seal is provided at the mouth of pockets in the form of at least one line or dotted, perforated seal/glue located at the mouth of a pocket, so a user can burst the seal by inserting a finger through the unburst seal, which hugs around the finger or fingers.

A pierceable perforation can be provided around the mouth area in the pockets shown in FIGS. 19 and 20. FIGS. 19, 20 shows a full sealed pocket with an unglue/unsealed perforation around the mouth area in the pocket. This perforation can be burst by piercing the user's finger/thumb into the pocket, so that an unburst perforation hugs around finger/thumb.

A full finger stability wall is accomplished by presenting two sheets or rolls of FDA approved and/or food service culinary customarily used material, prepping and working it, to accommodate each other so that the FDA approved and/or food service culinary customarily used materials of a different gauge adheres or seals itself onto each other FDA approved and/or food service culinary customarily used material which is a different FDA approved and/or food service culinary customarily used material, and when the tongs are cut, stability walls are presented with an at least one full different wall of a different gauge FDA approved and/or food service culinary customarily used material.

A partial stability wall can be provided onto an original FDA approved and/or food service culinary customarily used material from a single sheet of coated, uncoated, textured, layered FDA approved and/or food service culinary customarily used material, whereby a stability wall is provided by prepping the FDA approved and/or food service culinary customarily used material of the tongs, to accommodate a flexible strip which is bead glued or bead sealed onto the single sheet of FDA approved and/or food service culinary customarily used material. Then the single sheet of FDA approved and/or food service culinary customarily used material is folded to make pockets, with the stability strip is firmly against the wall, and is not a freely suspended, loose ring as in the glove of the Albert patent. As a result, now there is a pocket with a stability wall formed from single sheet, although other described methods can apply to make the pocket interior have a stability strip.

A layered wall of two or more sheets of FDA approved and/or food service culinary customarily used material can be layered/laminated with other FDA approved and/or food service culinary customarily used materials to form at least one wall.

A stretchable wall is accomplished by gluing/sealing a poly/rubber spandex FDA approved and/or food service culinary customarily used material with coated/uncoated loosely felted FDA approved and/or food service culinary customarily used materials, which are stretchable and which create hugging abilities of the wall of the pocket, in combination with non-stretchable materials.

Also, a draw string/thread can be sealed/glued in or around the pocket during the FDA approved and/or food service culinary customarily used material folding procedure so that a user can wrap the string/thread and secure it. The thread/string can also be sealed/glued into the pocket with a length of it provided out of the pocket, so it can be used to pull across to rip or cut and reveal the finger insertion opening into the pocket. The string can also be used to lock the user's finger into finger accommodation area (such as a jaw or finger accommodating strap).

FIG. 42 shows the option of multiple tabs 205, 206, and/or 207 connecting finger accommodating areas, such as pockets 204a, 204b of FIG. 42, or other finger accommodating features, such as straps 309 shown in FIG. 5A or straps 203a in FIG. 41. Also each connected tab can be used alone as a single connecting tab.

It is noted that there are two kinds of straps used in the present invention. First, straps can be open ended finger accommodating straps, like straps 309 shown in FIG. 5A or straps 203a in FIG. 41. In contrast, the present invention also optionally includes finger stability straps, such as straps 76a shown in FIGS. 19A, 19B and 19C, where the straps hug and/or are connected in part or in full, to an interior wall of the pockets of the set of tongs.

On the other hand, straps can be the variable width and stability one or more tabs of FIGS. 45, 46, 47 and 48 allow for an optional additional user controllability, optional soft ragged edge cut and also allow a custom size fit, by adding a stable snug pocket to pull back when a user spreads a finger and thumb away from each other, for a customized fit regardless of the size of the user's hands. This width and/or stability allowance tab 206, 207, 220 or 227 are configured to be whole and continuous in strength and performance, rather than have any weakened and/or altered stages, and can be used singularly, when used by itself, or in combination of multiples.

The clips 350 with hook/rings 352 or 353 can secure onto a tab or pocket of a tongs, then can hook and secure to the user's hand, finger/thumb, etc., and/or the ring can insert onto a finger to be combined with at least one clip.

The perforated tab 235 version of FIG. 52 can be made with a hole 208 in the tab 235, with the finger accommodating regions being pockets and/or straps and/or free finger features, so that when the perforated tab is torn in two or more individual sections 235*a*, 235*b* along tear line 230, a user can insert an individual finger into a hole 208 and then into an adjacent pocket connected to an end of perforated tab 235. Each section of the tongs can separately accommodate at least one thumb/finger of the user.

Another accessory to be added to the tongs, as in FIGS. 7-16, can be a nut shell, crab shell cracker where a gripping vice or torque force is required.

In an alternate agricultural embodiment, the set of the tongs can also be made as non-disposable tongs which are tools which are operable by insertion of the fingers and thumb into finger or thumb accommodating jaws, such as pockets or open ended straps. Such tongs can be used in landscape horticulture or other agricultural uses. The accessory can also be a textured surface which sticks onto a connecting tab area of the set of tongs, between the respective jaws, either as one gripping vice or torque force accessory that is bendable and/or individual gripping vice or torque force accessories that accommodate the thumb side and/or finger side of the tab. By attaching these gripping vice or torque force accessories and/or clip/hooks onto the central connecting tab of the jaws of the set of tongs, the user has created an area to establish more pressure per square inch to exert force in tearing food, such as meat or shrimp shells.

In this alternate agricultural embodiment, the gripping vice or torque force accessories allow more pressure per square inch, which can be shaped as shears blades or shaped as a beak shape which is sewn, fused, tacked, housed, etc., onto the jaws or connecting tab of the set of tongs These accessories in the hand apparatus can be mechanically assisted, and can work off a battery pack and/or AC/DC electrical hook up, where in the power can be portable in a backpack, waist belt, body belt, jacket, shoulder straps, and/or in a separate vehicle, etc. The accessory can have a sensor button in beak area and/or trigger elsewhere that, when touched by anything or object, it activates the beak, which can tear at food like a bird's beak. It can also be activated manually and/or have a timer, time clock, counter, communication with a computer, solar panel, etc., to power shears which have the ability to function with thumb and fingers and/or only on, fingers automatically and in between. These beak accessories can be an extension away from palm, hands, fingers, extension and can have a handle. The blades can be continuous, partial, bent, etc., to mimic joints of finger, at least two pairs of beak, at least one curved and/or straight knife, so that blades can be presented at any sides of fingers/thumb anywhere a finger/thumb goes it has the ability to snip, cut, shear, etc., such as for cutting and trimming horticultural bushes. An air pneumatic system can also be presented which consist of housing leather, metals, fabrics, plastics, rubber, etc. It has valves, throttles, drive, grease fitting, bearings, spindles, o rings, gaskets, air hose, compressor, motor, transmission, including known combination in the arts.

All tongs can be made from disposable or non-disposal materials, such as silicone, neoprene, rubber, paper, plastic, fabric, textiles, pulp, wood, textile, petroleum, oil-base, Kevlar, Nomex, Tyvek. Disposable tongs can be made of crepe paper, Bounty Paper Towels™, Scotts™, tissues and other existing FDA approved and/or food service culinary customarily used materials known in the art and in existence at this current time of the state of the art in paper constructions and can include future formulations, etc., and/or combinations thereof.

It is further noted that optionally the tongs can be made of edible paper or other edible FDA approved and/or food service culinary customarily used material. For example, all additional FDA approved and/or food service culinary customarily used materials can be at least one layer and edible and or coated with sugar, flour, doughy liquids, chocolate, wafer, oils, waxes, additives, Rubber, gums, synthetic and or natural, etc., can be provided to make air moisture proof barrier. The edible tongs can have any flavors, scents, smells, food, air, nature, spices, meats, fruits, veggies, candy, floral, cheese, wine, liquor, etc. It is already known that edible paper such as rice paper, sugar paper and others like it already exist. These FDA approved and/or food service culinary customarily used materials can be layered and coated with digestible and or nutritious coatings such as sugar, salts, syrup, oils, gums, waxes, etc. which can also be used to create textures on food touching sides and or hand touching sided and these coatings can work as an method of sealing, making finger accommodating areas of tong. The set of edible tongs can be made of a combination of edible and non-edible FDA approved and/or food service culinary customarily used materials and coatings, layers, etc., wherein only the edible portion is consumed. For example, any release liner that is removed can be made of non-edible FDA approved and/or food service culinary customarily used materials, as long as the final set of tongs to be used is completely edible. Then heat, pressure and other method are applied, the application, it reactivates edible coatings which can cook, heat, press, bond, etc. FDA approved and/or food service culinary customarily used materials which will assist in making tongs. The trademark Wikipearl™ is edible layer, coating, wrapper FDA approved and/or food service culinary customarily used material which is described as being held together by calcium ions and can include particles of chocolate, nuts, seeds, etc. The edible paper can be coated with electro static gel formed by harnessing interaction between natural food particles, nutritive ions, and a poly saccharin. This skin is water and oxygen impenetrable and is inspired by nature itself as inventor and professor David Edwards explain although used in refrigerated imagine the possibilities for burger wrappers, packaging, etc. Companies like Wikicells and Monosol are introducing edible packaging which can make litter a thing of the past such as mixing of starch or co-processing of more than 50% starches with synthetic polymers, thermoplastic extruded starch, etc. Base FDA approved and/or food service culinary customarily used materials and or layer(s) can be bamboo card, rice paper, starch paper, sugar paper, frosting sheet, plastic, paper, etc., and at least one layer can be not edible this layer can be a protective combination so when peeled away edible portions can be consumed. Other starches, such as rice, etc., can be provided in layers, which can be of high to low density FDA approved and/or food service culinary customarily used materials and can activate at cooler temps and or hotter temps. Because the edible layers, such as starch, rice, etc., can get slippery when moisture contacts the edible layers, then other granular, textures surfaces can be introduced and or imbedded in FDA approved and/or food service culinary customarily used materials, layers, etc., such as nuts, shells, seeds, corn, rice, hard candy, etc. The aforesaid FDA approved and/or food service culinary customarily used materials can be used as grip, textures, etc., to prevent slippery surfaces. At lease a layer/portion can be a flavored chewing gum such as mints, spearmints, cherry, etc., and at least a portion of the tong can be peeled and or broken and given to a friend as a gum, candy, mints, sucker. FDA approved and/or food service culinary customarily used materials can be colander to breakdown at hotter or cooler temps. All parts, layers, texture, FDA approved and/or food service culinary customarily used materials coatings, etc., can be natural and or synthetic. Edible coating and/or FDA approved and/or food service culinary customarily used materials can become an edible adhesive to assist in making of the set of tongs by manufacturing steps such as by cooking, pressing, heating, folding, application of radio frequency, vibrations, etc. All tongs and all parts or food accommodating accessories (such as chop sticks, for example, the crab shell cracker or meat tearer, can be edible and can be made of various specific lengths, width for universal fit and or particular size fit. The set of tongs can be combined with commercial displays, offers, prizes, menu pictures, or produced as edible bowl/bucket food, sea food, with thematic packaging, in sealed container, bag, box, etc., with/without non and nutritional and or digestive materials, in accordance with FDA label printing regulations. The edible set of tongs can also have displays printed with food safe digestible edible ink printing logos, etc.

While the aforementioned describes single tabs, each version can have at least one additional length/layer of tab in between and/or edges of the finger accommodating area.

The tong's stability clip of FIGS. 60 and 61 can accommodate anywhere on the tongs and/or can interact with any portion of hands area, and can have open hook and/or full or partial ring. Tongs with clips or hooks can be made with at least a portion of excess material to assist in stabilizing, with, for example, an extra portion off of a main tab, which has a peelable glue area. Each clip can have at least one ring, open or closed, and/or at least one hook and/or at least one clip in combination.

A rigid/semi-rigid tongs can be provided, where at least one side has a finger accommodating area and other side is a free finger in which the tongs have a reopening memory.

Moldable sealers allow for manipulation of finger accommodating areas to become contouring rest areas for holding foods. Sealers can be molded towards the top, having an inner pocket ability to seal inside the pocket. Sealers can do a fill length seal, perforated seal and/or segmented seal anywhere in or out of the pocket.

A stationary and/or swiveling finger rest area as in FIGS. 39 and 40 is provided with the ability to channel, guide, lock, pierce, snap, etc., for optional securing utensils, sticks, etc., in the hooks or rings. The stationary and/or swiveling rest can lock on itself and can be and/or have a neck, body, limbs, etc., and at least a portion of the rest area can be flat and/or any shape and can have holes. This flat extension can have a peel able area exposing glue which can stick/attach anywhere on the tongs. This flat extension can also be glued/sealed, etc., anywhere in and/or out and/or in-between layers of the tong/pockets/tabs. The finger rest area 206 can allow mobility of utensils, sticks, etc., so that those instruments to have a slidability and/or the swiveling, which will allow tools, sticks, utensils, etc., to swivel away from the tongs.

Other versions of the tong can be made with at least portion/layers which are made with heat resistance coating, and/or materials, etc., such as, for example, parchment silicone paper, Kevlar, Nomex, etc. Also in all versions a temperature thermometer sticker can be stuck on and/or presented in at least a portion of the tong to test the temperature of food items to be held by the tongs.

All tongs can have a stability seal at the mouth and/or into the pocket, and burstable seals can be single spaced or provided with doubled angles, etc.

This allows for fingers to enter the pockets of the tongs while bursting through the seal or glue in which the unbursted seals hug around/against the user's fingers/thumb.

A breathable finger accommodating areas are provided, to prevent sweating fingers, by using a breathable material and/or punching holes in materials before/during making tongs. Punched holes can be any size, pattern, shape, character, people, place, thing, etc.

An automatic dispenser which can make and dispense the tongs or just dispense pre made tongs, is powered by AC/DC to accommodate at least one roll material and/or sheet, motor, rollers, spindles, gears, rewind, unwind, guided features, vacuums, mother board, computer, programmer, kickers, puller, printer, jet, hot stamp, coin acceptance, credit card acceptance, tensioned(s), wheels, heating system, molds, rotary dies, timer, on/off button, knife cutting system, glue stamp, steel rule application, dies, clicker, hydraulic, air, pistons, transmissions, can be a part of known machineries in the arts of binary, printing, etc.

A sheet of disposable flexible material can be physically coated/laminated/splattered/texturized/layered heat/air dried extruded and then winded into rolls, sheets, etc. On that finished flexible material a length and width of flexible or non-flexible material, such as straps, bands, etc., can be presented to form straps in the pockets. It can be bead glued and/or fully glued, heat sealed, etc., to at least one pocket wall to make that pocket wall more firm, rigid, stable, sturdy, etc., so that the wall or strap can press against fingers/thumb. Uncoated/coated textured material is prepped worked, folded to make the pockets of the tongs while leaving at least one other wall to be the original flexible material and free of straps allowing the flexible material, to bend, contour, form, etc., around foods, things. Also the splattered portions of the tong can have different decomposition features, to assist in landfill breakdown.

Optional holes in the central tab can be added during cutting. To make open strap(s) finger accommodating regions at least one length and width of material is used optionally to make tongs with internally mounted flexible straps, bands, straps, etc., which are laid in the finger accommodating areas of a sheet of uncoated, coated, textured material pre glued and/or ready to be heat sealed. Tongs which have in combination pockets and straps can be made of a sheet of material as described, which is pre glued and folded on one side and/or (heat sealed) to make pocket and a separate length(s) of flexible/non flexible material is sealed/glued onto the other side of the sheet in the finger accommodating area, to make a combination of a pocket on one side and finger accommodated straps on the other side, as shown in Figure A.

In an optional embodiment, the pockets are connected by a tab outside the palm area to allow universal size accessibility into pockets, which are coated or uncoated. Pocket adjustment can be made by pulling back on the connecting tab connecting the two finger accommodating areas.

If the tab is located inside the palm area, the palm is optionally coated with texturization of a non-permanent adhesive type of material, to allow a more snug custom fit to a particular finger size, and where the tab also adds a pocket adjustment ability for that custom size, by allowing pockets to pull back snug on the user's fingers by spreading thumb and fingers away from each other.

Each version of the tongs can have at least one additional length of a connector tab in between and/or on the edges of the pockets and/or anywhere in or on the finger accommodating area.

At least a portion of the peripheral edge of the tongs or on all pocket sides, can be made in any shape, cut, design, size, etc., both internal and/or external.

Figure 62A:
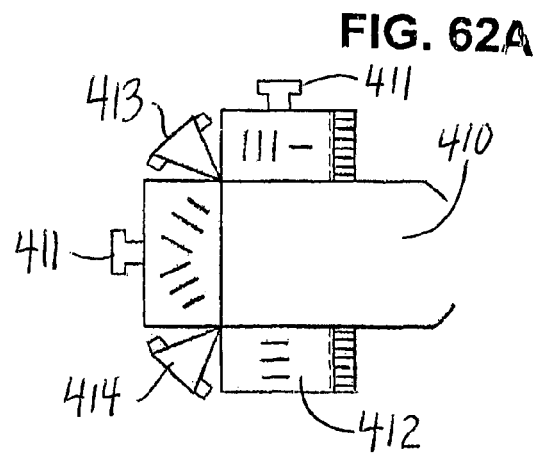
FIGS. 62, 62A, 62B, 62C, 62D, 62E and 62F show various templates for a food package container, that has one or more optional tear off sets of tongs with pockets or other finger accommodating areas, which are formed by folding the portions thereof and connecting them with lockable/unlockable insertion tabs insertable in slits in the set of tongs formed from the torn off portion of the food container template. Optionally, the tear-off tongs can already be partially or fully made with pockets and connecting tabs, with pockets or other finger accommodating areas. In the partially made tongs, the user can choose whether to use a full pocket or an open ended finger accommodating strap. The folds can also optionally have finger stability areas formed to press and constrict the fingers in place. The entire tongs can also have auxiliary fasteners, such as pressure closable fasteners, such as Zip Loc type linear fasteners.
Figure 62:
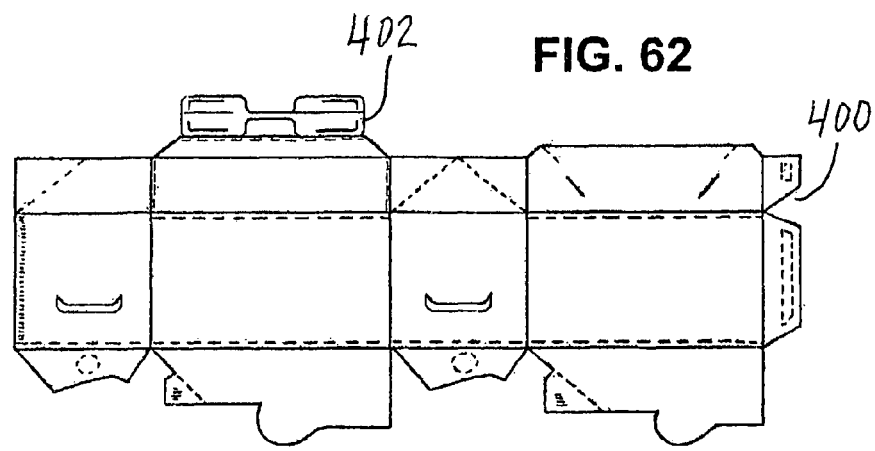

In addition, the aforementioned sets of tongs can optionally be provided in combination with other items. For example, as shown in FIGS. 62-62F, the set of tongs can be provided as part of a sack, bag, cup, French fries serving container, box, tray. etc. Additionally, the connecting tabs can be permanently attached, such as being sewn or adhesively attached, or can be temporarily attached by other means, such as by zip lock fasteners, or can be removable by perforations provided anywhere on the tabs or jaws of the set of tongs. Excess tab material can be torn and or tucked away. The set of tongs, including the jaws and connecting tabs can be printed, textured, layered, knurled, embossed, etc., on any sides. All seams can be continuous, rounded to follow through edges, corners, sides, etc. Stability holes, such as shown in FIG. 5A, can be holes, or can be slits with or without further breakable perforates for insertable tab and or finger portions. The set of tongs can be made for right and or left hand sides.

In this embodiment shown in FIGS. 62-62F, the tongs can start as a template that is foldable with lockable/unlockable insertion tabs insertable in slits on opposite sides of the template to form hollow pockets or other finger accommodation areas, such as open ended straps, with optional side tabbed portions to enclose the sides of the pockets thus formed.

Slits can be any length and or angles and accommodate other silts at other lengths and or angle. Locking seam sealer tabs can be optional. Foldable stability features can be perforated, provided with slits, die cuts of the finger tongs can take the shape of fingers and or just bend and hug against fingers. Anywhere on tong can have scores, bends, etc., that when in use it mimics the bending joints of fingers/thumb, these bending joints can be at any angles to each other which can contour, hinge around foods, objects and enhance the firm grasp of hands. Entire tongs can be in individual parts and then assembled by someone. While FIGS. 62-62F show tongs associated with packaging, as shown in FIG. 62G, it is noted that a tong in general (associated with or without packaging) can have the same foldable stability features, such as being perforated, provided with slits and foldover insertable tabs and can take the shape of fingers, or just bend hug against fingers.

Figure 62B:
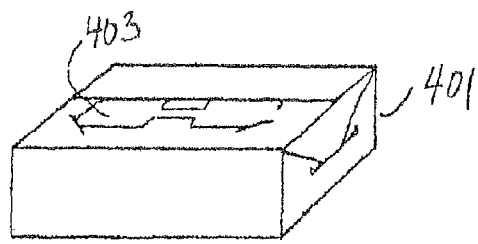
Figure 62F:
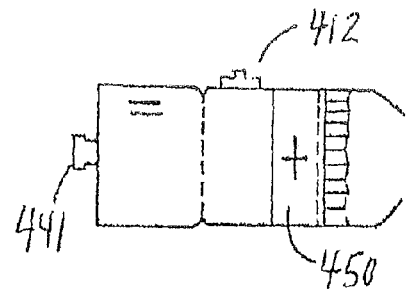
Figure 62D:
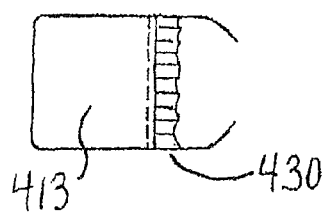
Figure 62E:
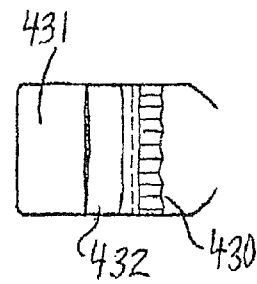
Figure 62C:
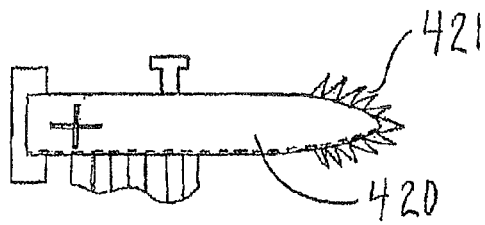

For example, FIG. 62 shows template 400 for a food container assembled as a box 401 in FIG. 62B, with tear-off sets of tongs 402 or 403. FIG. 62A shows another template 410 with insertion tabs 411, insertable in slits 412, with tear-off tongs 413, 414. FIG. 62C shows tongs 420 with a converging ratchet end 421 for insertion within a slit, wherein the ratchet end enables varying tightness of fits. FIGS. 62D-62F show tongs 430 with foldover straps 442 or finger/thumb pockets 431, or with insertion tabs 441 and slits 442 of tongs 450.

Although the tongs 402 or 403 on the box 401 shows glue or other sealing methods in an L-shape and pocket folds top to bottom, it can also seal bottom to top and the sealing or gluing can be parallel to each other, and also, the pockets can fold left side to right side or vice versa. A shortened pocket can be an open strap or straps.

Accommodating areas on either sides of the tongs 402 or 403 (front, back, left, right, etc.,) and/or an accessory accommodating area can hold a toy, prize, food item, etc.

For packing and sheet arrangement to fit more tongs 402, 403 with insertable tabs/pockets or other finger accommodating areas, such as open ended lockable straps, can be provided separate or all together. The tongs 402 or 403 can be made of multiple layers and materials, to accommodate packaging features, where the tongs are associated with food containers. Also, the sheets of tongs can be used to make larger food containers and covers from the multiply attached tongs 402, 403. For example the insertable tab has locking T base and locking zip head so the individual tab/pocket can be incorporated with hole/slit to secure. All edges can have securing slits at any angle, or at any location, to accommodate a securing/biting point on tong. Insertable tabs can be wider or narrow at top and or bottom to adjust lopsided fitting. Insertable tabs/pockets can be sewn through set of slits/holes where either end or at least one end ends up on top of finger accommodating area and not the food touching side although an end can end up anywhere inside tong, sides, up, down, etc. To avoid printing on both sides of material knurling, embossing, stamping, etc., can give a texture and or provide a logo, etc., on any side. Accommodation areas, and/or areas located anywhere on tong 402, 403, can have bends, creases, scores, seams, beaks, etc., to assist in fitting, graspability, a contour forming ability around objects, foods, etc., in any angles and/or patterns. The insertable tabs can also have slit/holes in which it can be given as a toy, ring with/without a diamond shape. The tab portions can be a theme or depiction of fanciful characters. Tongs 402, 403 can have peel away layers to reveal images, change texture, surfaces, feel usage, etc. As mentioned, the entire tongs 402 or 403 can be provided in parts, which can be assembled to become a functioning tong 402, 403. Furthermore, extensions, tools, features, themes, toys, etc., can be assembled as accessories to the tongs 402 or 403.

FIG. 62G shows a tong finger accommodating area 600, which can be a closed ended pocket as shown, or an open finger accommodating strap(s) area, with a connected tab 601, as well as a finger stability member 602 including a locking tab end 603 attached to an extension body 604, wherein the locking tab end 603 is insertable a slit 605 to tighten the mouth or body of the finger accommodating area 600.

Figure 62H:
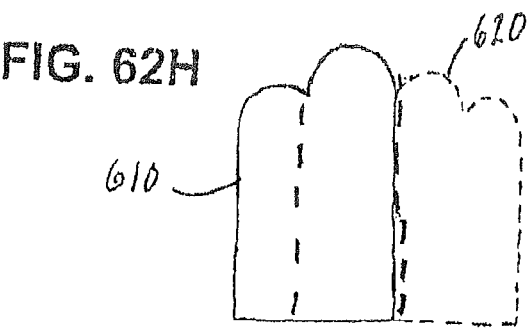
FIGS. 62H and 62I are close-up detail views of finger top versions of tongs wherein the contour of one or more finger accommodating areas follows the contour of one or more fingers tip areas of the user.
Figure 62I:
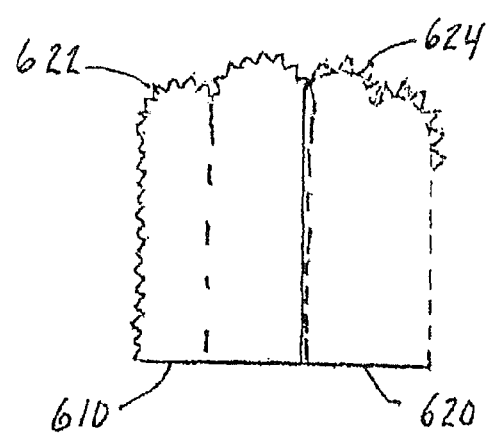
Figure 62G:
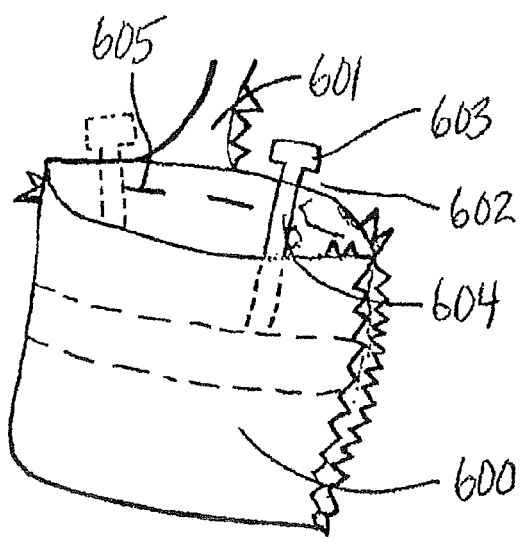
FIG. 62G is a close-up detail view of a tongs with slits and foldover insertable tabs for stability.

FIGS. 62H and 62I show close-up detail views of finger top versions 610, 620 of tongs wherein the contour of one or more finger accommodating areas follows the contour of one or more fingers tip areas of the user. In FIG. 62I, optional edge cuts 622, 624 (as described previously) are shown.

Figure 63A:
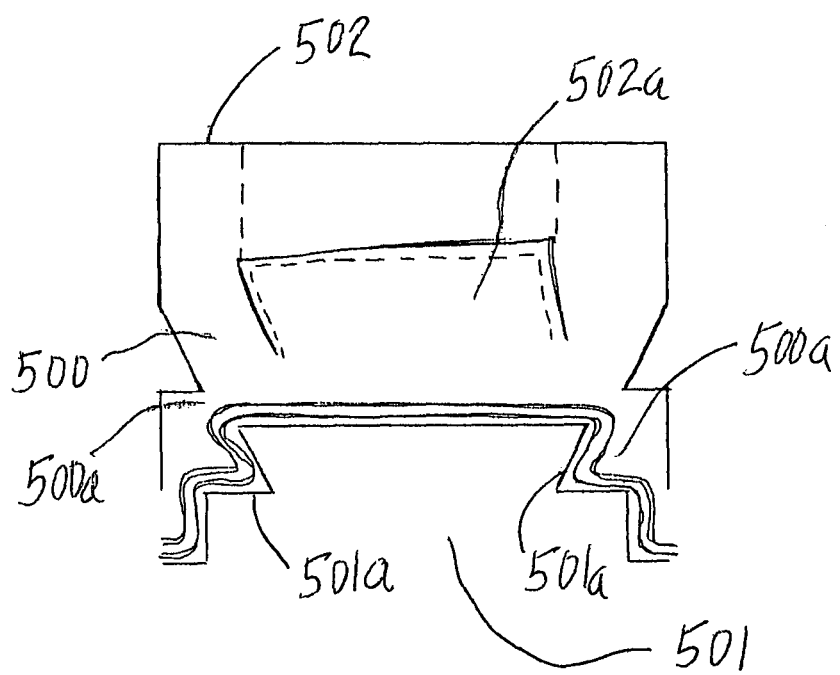
FIG. 63A is a diagrammatic side view of the male die and female die of FIG. 63, shown engaged together.
Figure 63B:
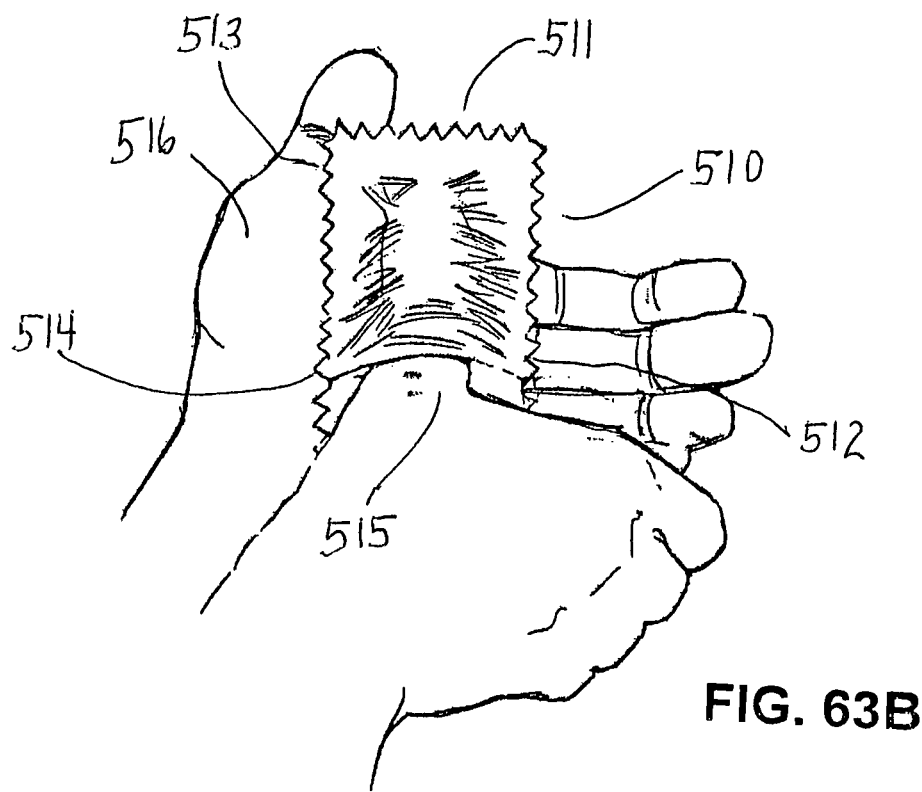
FIG. 63B is a perspective view of the tight, shut mouth jaws of the tongs produced with the male and female dies of FIG. 63 and FIG. 63A, showing two hands of the user, with one hand holding the tongs for tight insertion of the thumb into one of the tight, shut mouth jaws of the tongs.

As shown in the alternate embodiment of FIGS. 63, 63A and 63B, in an alternate embodiment, the set of tongs 510 can have tight shut mouth stabilizing jaws, such as pockets 511, each having an optional "stabilizing tight body" with a closed mouth shut finger(s)/thumb insertion opening 512, preferably with an injury preventive soft cut feature edge 513 in which the soft cut style in addition adds an identification, providing visual familiarity or recognition to the visual appearance to the tongs 510. The soft cut edge 513 additionally allows for an easy tearable edged connecting tab 514, so that each of the pair of the individual tight shut-mouth stabilizing pockets 511 can be independent in use of each other, by tearing apart the tongs into separate pockets, in which each individual tight shut-mouth stabilizing pocket 511 can independently stabilize itself on a finger(s)/thumb 515. In this version the tongs 510 have at least one finger/thumb accommodating area and at least one connecting tab, as well as optionally at least one additional stability feature beyond the tight shut mouth and/or stabilizing body of each pocket 511 of the tongs 510.

In this embodiment of FIG. 63, a deeper or longer soft cut feature can be provided anywhere on the connecting tab 514 and be used to tear the tongs 510 in two pieces. This at least one soft cut edge 513 can be deeper/longer to emphasize a separation point on the tongs 510 for each tight shut mouthed jaw 511 of the tongs 510, to be used individually freely, and optionally, where one or more of the jaws, preferably pockets 511, can have tight shut mouth stabilizing features, and at least one pocket can optionally have a front bulge. The front bulge and optional loose body can be provided for less entrapment of the fingers, and to prevent finger nails or nail accessories from ripping thru pockets when the pockets are under stress.

The jaws 511 of the tight, shut mouthed tongs 510 be made from a single sheet of material in which the folded material is placed over a set of convex or flat dies 500, 501 that have the shape of the jaw's pocket 511, in which the respective peripheral edges of the dies have a female concave valley 501a, which accommodates a male convex foot 500a on the shroud 502 associated with the dies 500, 501, which can also have multiple feet. Male die 500 can be attached by fastener 506 (such as a screw, bolt or nut) to shroud 502.

So, as shown in FIG. 63B, when the folded paper or other material to be used to form tongs 510 is placed over the dies 500, 501, then the convex male foot 500a on the shroud 502 pulls the material tight into the female concave valley 501a and seals the pulled tight jaws of the tongs being formed between the dies 500, 501. At this point, the mouth of the selected pocket or pockets is rendered tight and flat, and which allows minimal light to enter each selected pocket, or pockets. So, as shown in FIG. 63, before the use of respective jaws of the tongs, the user has to use both hands, as shown in FIG. 63B to put on the tight shut mouthed jaw or jaws 511 of the tongs 510, in which the held tong jaw 511, held in one hand 516 of the user, now assists the user to manipulate and wiggle the other hand/finger(s) thumb 515 into the tight shut mouthed fit pocket 511. Then the second pocket 511 (not shown) is held by one hand and the user also manipulates and wiggles the other hand/finger(s)/thumb into the other pocket 511 of the tongs.

The tensile pull on the material transfers to the inserted finger 515, which forces the material to constrict back on the finger(s)/thumb 515, therefore stabilizing itself on the finger(s)/thumb 515. The peripheral edges 513 of the female concave valley 501a can have ledges 501b in any direction, length, section, angles, etc. Furthermore, the ledges 501b can have deeper valleys to further stretch the paper material of the tongs 510. The male convex foot 500a on the shroud 502 can have a corresponding shape an opposite side of the female die 501, so that when the dies 500, 501 come together they lock into each other. Furthermore, the male die 500 can have additional ridges, crests or peaks 500b which can go further into the deeper female valleys 501b. The male and female dies 500, 501 can be manipulated to pull more or less, therefore they can produce pockets 511 with multiple mouth accessibility.

The convex male feet 500a can be continuous or in pieces and can be changeable and/or interchangeable on slidable tracks consisting of different size, height, placement, etc. The male peaks, crest, ridges, 500a, 500b which accommodate female ledge accommodating valleys 501a, 501b and can go further into the female deeper valleys 501a, 501b. Different size, width, depth of the pocket mouth opening 512 and the tensile pull is determined by the valleys, depth, ledges, deeper valleys, ridges, peaks, and or their placement. The female die 501 can be continuous or in pieces and can be changeable and/or interchangeable on slidable tracks 503 consisting of depths, valleys, deeper valleys, ledges, etc.

A very important features of the ridges, peaks, etc., of the soft, irregular edges 513 is whether they are single, continuous, wavy, etc., and that they have the ability to make many different sized pocket openings 512, and therefore also can make the aforementioned tight shut mouthed entrance 512 of the tongs' pocket 511, for stability with deeper valleys, and be less tight along the length of each pocket 511, with a valley, which gives the finger(s) a free feeling insertion into the pocket 511. This free insertion movement of the finger(s) is in contrast to an entirely tight pocket 511 which is designed to tightly traps the whole finger 511. The formation of the tongs between the dies 500, 501 can also make the pocket 511 less tight on one side of pocket 511 and conversely, being pulled tight on the other side of pocket for a custom deformed pocket, for use when necessary such as with twisted knuckles, bent fingers, illness, birth features, or other physical finger or hand deformities, etc. The pockets 511 can also optionally have an hour glass stability shape.

Another important feature of the female die 501 is that it can make tongs have a frontal bulge for enlarged or meaty finger(s) to nest in. Optionally there can be provided at any strategic area(s), such as sharp particles 504, air suction area 505, sticky surfaces, micro particles, metal shaving, pins, etc., which can be permanently glued, welded (as weld attachment 507) compounded, screwed, imbedded, etc., and/or temporarily imbedded in wax into any surface of the tongs to enhance food graspability. Optionally, these sharp particles 504/air suction members 505 bite the food touching side of the jaw of the tongs, preventing this side from moving or being pulled by the aforementioned peaks. Therefore, as also shown in FIG. 20E as aforesaid, when the male peak 500a goes into the female valley 501a, more of the loose non-food touching side material (pocket back wall) pulls tighter and after the shroud completes in making the seal with sealer 502a, the end result is a pull tight pocket with a firm back wall and a loose food touching side. Because of the tight firm back wall, the loose front wall will bulge making a natural nesting area for the larger or fatter meaty frontal finger/thumb. The loose optional pocket associated with the huggable mouth of the pocket reduces tight entrapment of the fingers or thumb in the pocket, and prevents finger nails and finger nail accessories from ripping through pockets when the pockets are under stress. This process also eliminates the extra step of dimple texturizing materials before use. Optionally other stability feature can be presented.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A triple use finger protecting, environmentally and wildlife friendly food handling product made from disposable materials and having a feature to help prevent paper cut injury to the fingers, thumb, mouth, lips and tongue of the user comprising:

a set of tongs including pair of finger(s)/thumb accommodating pockets with at least one exterior food contact surface on each pocket;
each said pocket having a respective finger(s) or thumb accommodating interior, said pockets connected by at least one connecting tab,
at least a portion of at least one tearable seal closing a mouth entrance of said at least one pocket of said pair of finger(s)/thumb accommodating pockets;
said pocket having a perforation line adjacent to said tearable seal, said perforation line also closing said mouth entrance of said at least one pocket;
wherein further an inserted finger(s) or thumb of the user pierces said perforation line to open at least a portion of said interior of said at least one pocket, wherein an area around said pierced perforation line at said mouth entrance of said pocket hugs and stabilizes the finger(s)/thumb in one of said pockets with at least one finger(s) accommodating area,
wherein said pockets of said set of tongs are pierceable by the finger(s) or thumb at the opening mouth entrance of the pockets of the jaws to pierce at least a portion of the pocket, to reveal at least said portion of the opening of the pocket, whereby the partially open opening hugs around the finger(s) or thumb, or if fully open, fully reveals the pocket interior;
further comprising a peripheral edge of each of said pockets and said connecting tab includes an unbonded free edge beyond a peripheral sealed edge, wherein respective soft, irregular, non-smooth sealed peripheral edges are provided around the edges of the set of tongs, with said soft, injury preventive edges having irregular free ends extending beyond a seal parallel to, and in the vicinity of a periphery of a finger(s)/thumb insertion pocket or strap of a set of tongs, and/or said connecting tab, to promote tearing at the seal to make said soft, irregular, non-smooth sealed peripheral edges, and thereby providing a an injury preventive soft, irregular non-smooth sealed finished peripheral edge to prevent paper cuts on the fingers, thumb or mouth of the user;
wherein after use, said tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs.

2. The triple use finger protecting, environmentally and wildlife friendly food handling product of claim 1 wherein a further finger stability member is provided inside of each said pocket to stabilize the finger(s) or thumb of the user within each said respective pocket.

3. The triple use finger protecting, environmentally and wildlife friendly food handling product of claim 1 wherein said soft edged pocket is provided with at least one in situ texturized region.

4. The triple use finger protecting, environmentally and wildlife friendly food handling product as in claim 1 further comprising
said pocket is an open strap(s) tong with at least one finger(s) accommodating area connected to at least one connecting tab,
said open strap accommodating a finger(s) or thumb therethrough.

5. The triple use finger protecting, environmentally and wildlife friendly food handling product as in claim 1 wherein said material is edible.

6. The triple use finger protecting environmentally and wildlife friendly food handling product as in claim 1 wherein said material is edible.

7. A triple use finger protecting, environmentally and wildlife friendly food handling product comprising:
a set of tongs including a pair of open finger/thumb accommodating pockets joined by a central connecting tab, said set of tongs produced by at least one sheet of folded paper,
each said pocket being selected from the group consisting of:
a) at least one of an open tong with an open finger or thumb insertion mouth end and an opposite closed distal end or,
b) an open tong with an open finger or thumb insertion mouth end and an opposite open distal end;
said set of tongs further having a burstable seal located within an interior of each said pocket, said burstable seal bonding a front and a back wall of said pocket to create a finger stability area within an interior of said pocket, said burstable seal being burstable by insertion of the user's finger(s) or thumb therethrough, to grip and stabilize said finger(s) or thumb within each said respective pocket of said set of tongs, wherein said unburst portion of said burstable seal hugs around the finger(s) or thumb of the user,
wherein said connecting tab is selected from the group consisting of being stretchable; or having multiple length portions, or is vented, or is provided with at least one additional connecting tab, or is made of two intersecting portions.

8. A triple use finger protecting, environmentally and wildlife friendly food handling product made from disposable materials and having a feature to help prevent paper cut injury to the fingers, thumb, mouth, lips and tongue of the user comprising:
a set of tongs including pair of finger(s)/thumb accommodating pockets with at least one exterior food contact surface on each pocket;
each said pocket having a respective finger(s) or thumb accommodating interior, said pockets connected by at least one connecting tab;
wherein said tongs are formed from at least one folded sheet of flexible material folded over a set of female dies pressed by a set of males dies to form finger stability crimped open three dimensional finger and thumb portions, said folded materials and said dies being provided under a shroud providing a sealing of said tongs;
said die crimped, folded finger and thumb portions forming a pair of tight at least partially shut mouth huggable stabilizing pockets, each said pocket having a tight at least partially shut mouth opening stabilizing around said finger(s) or thumb; in which the user manipulates and wiggles the finger(s) or thumb of one hand into said tight shut mouthed pocket while holding said pocket with the other hand.

9. The triple use finger protecting, environmentally and wildlife friendly food handling product as in claim 8, wherein said tongs include a lottery type surface region on at least a portion thereof to form a lottery ticket.

10. The triple use finger protecting, environmentally and wildlife friendly food handling product as in claim 8 wherein said product has a tearable separation point so that each pocket can be used individually freely.

11. The triple use finger protecting, environmentally and wildlife friendly food handling device of claim 8 wherein at least one pocket has tight features to tighten at least around respective fingers or thumb of the user.

12. The triple use finger protecting, environmentally friendly food handling product of claim 8 wherein one side of each pocket bulges outward.

13. The triple use finger protecting, environmentally friendly food handling product of claim 8 wherein said material is edible.

14. The triple use finger protecting, environmentally friendly food handling product of claim 8 wherein a peripheral edge of each of said pockets and said connecting tab includes an unbonded free edge beyond a peripheral sealed edge, wherein respective soft, irregular, non-smooth sealed peripheral edges are provided around the edges of the set of tongs, with said soft, injury preventive edges having irregular free ends extending beyond a seal parallel to, and in the vicinity of a periphery of a finger(s)/thumb insertion pocket or strap of a set of tongs, and/or said connecting tab, to promote tearing at the seal to make said soft, irregular, non-smooth sealed peripheral edges, and thereby providing a an injury preventive soft, irregular non-smooth sealed finished peripheral edge to prevent paper cuts on the fingers, thumb or mouth of the user;
- wherein after use, said tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs;
- wherein after use, respective tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs.

15. A food handling product comprising:
- a set of tear off tongs including pair of finger(s)/thumb accommodating pockets with at least one exterior food contact surface on each pocket;
- each said pocket having respective finger(s) or thumb accommodating interior, said pockets connected by at least one connecting tab;
- each said pocket being selected from the group consisting of:
  - a) at least one of an open tong with an open finger or thumb insertion mouth end and an opposite closed distal end or,
  - b) an open tong with an open finger or thumb insertion mouth end and an opposite open distal end;
- wherein said tongs are provided attached onto a food package, wherein said tongs are attached to said food package by a perforatable common edge for tear off separation of the tongs from the food package for use in eating the food contained within the food package,
- wherein said tear off sets of tongs are selected from the group consisting essentially of a set of ready to use tongs or a set of tongs formed by folding the portions thereof and connecting them with lockable/unlockable insertion tabs insertable in slits in the set of tongs formed from the torn off portion of the food container template.

16. The food handling product as in claim 15, wherein said tear-off tongs are provided with closed ended pockets and/or open finger accommodating straps, wherein the user can choose whether to use either a full pocket or an open ended finger accommodating strap for insertion of the thumb or finger(s) therein.

17. The food handling product as in claim 15, wherein said pockets further having components selected from the group consisting essentially of at least one finger stability area formed to press and constrict the fingers in place or at least one textured surface component.

18. The food handling product as in claim 15, wherein said disposable materials is edible.

19. The food handling product as in claim 15 wherein said tongs of said package include a lottery type surface region on at least a portion thereof to form a lottery ticket.

20. The food handling product as in claim 15 wherein said tongs of said package is made of multiple layers of different gauge materials, at least a part of both layers being exposed to the food product being grabbed.

21. The food handling product as in claim 20 wherein at least one of said layers being textured.

22. The food handling product as in claim 15 wherein said tongs have at least one score for bending or folding.

23. A triple use finger protecting, environmentally and wildlife friendly food handling product made from disposable materials and having a feature to help prevent paper cut injury to the fingers, thumb, mouth, lips and tongue of the user comprising:
- a set of tongs including pair of finger(s)/thumb accommodating pockets with at least one exterior food contact surface on each pocket;
- each said pocket having a respective finger(s) or thumb accommodating interior, said pockets connected by at least one connecting tab,
- at least a portion of at least one tearable seal closing a mouth entrance of said at least one pocket of said pair of finger(s)/thumb accommodating pockets;
- said pocket having a perforation line adjacent to said tearable seal, said perforation line also closing said mouth entrance of said at least one pocket;
- wherein further an inserted finger(s) or thumb of the user pierces said perforation line to open at least a portion of said interior of said at least one pocket, wherein an area around said pierced perforation line at said mouth entrance of said pocket hugs and stabilizes the finger(s)/thumb in one of said pockets with at least one finger(s) accommodating area,
- wherein said pockets of said set of tongs are pierceable by the finger(s) or thumb at the opening mouth entrance of the pockets of the jaws to pierce at least a portion of the pocket, to reveal at least said portion of the opening of the pocket, whereby the partially open opening hugs around the finger(s) or thumb, or if fully open, fully reveals the pocket interior;
- further comprising a peripheral edge of each of said pockets and said connecting tab includes an unbonded free edge beyond a peripheral sealed edge, wherein respective soft, irregular, non-smooth sealed peripheral edges are provided around the edges of the set of tongs, with said soft, injury preventive edges having irregular free ends extending beyond a seal parallel to, and in the vicinity of a periphery of a finger(s)/thumb insertion pocket or strap of a set of tongs, and/or said connecting tab, to promote tearing at the seal to make said soft, irregular, non-smooth sealed peripheral edges, and thereby providing an injury preventive soft, irregular non-smooth sealed finished peripheral edge to prevent paper cuts on the fingers, thumb or mouth of the user;

wherein after use, said tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs.

24. A triple use finger protecting, environmentally and wildlife friendly food handling product made from suitable disposable materials and having a feature to help prevent paper cut injury to the fingers, thumb, mouth, lips and tongue of the user comprising:
 a set of tongs including pair of finger(s)/thumb accommodating pockets with at least one exterior food contact surface on each pocket;
 each said pocket having a respective finger(s) or thumb accommodating interior, said pockets connected by at least one connecting tab,
 each said pocket being selected from the group consisting of:
  a) at least one of an open tong with an open finger or thumb insertion mouth end and an opposite closed distal end or,
  b) an open tong with an open finger or thumb insertion mouth end and an opposite open distal end;
 a peripheral edge of each of said pockets and said connecting tab includes an unbonded free edge beyond a peripheral sealed edge, wherein respective soft, irregular, non-smooth sealed peripheral edges are provided around the edges of the set of tongs, with said soft, injury preventive edges having irregular free ends extending beyond a seal parallel to, and in the vicinity of a periphery of a finger(s)/thumb insertion pocket or strap of a set of tongs, and/or said connecting tab, to promote tearing at the seal to make said soft, irregular, non-smooth sealed peripheral edges, and thereby providing a an injury preventive soft, irregular non-smooth sealed finished peripheral edge to prevent paper cuts on the fingers, thumb or mouth of the user;
 wherein after use, said tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs.

25. The triple use finger protecting, environmentally and wildlife friendly food handling product as in claim 24 wherein said product has a tearable separation point so that each separate tong can be used individually freely and separated from the other tong of said set of tongs, wherein said at least one pocket having said partially open opening hugging said finger(s) or thumb, forms a huggable pocket, allowing for independent pocket stability in which said free end cut softened edged pocket allows for easy tab separation, so that said pockets may be cut free from said connecting tab.

26. The triple use finger protecting, environmentally and wildlife friendly food handling tongs as in claim 24, wherein when said connecting tab is torn to separate each pocket from the other said pocket, a portion of said connecting tab remains to be foldable over a portion of each respective pocket to hide a food contaminated portion of a respective separated pocket, to provide a clean area to hold said respective pocket.

27. A triple use finger protecting, environmentally and wildlife friendly food handling product comprising:
 a set of tongs including a pair of open finger/thumb accommodating pockets joined by a central connecting tab, said set of tongs produced by at least one sheet of folded paper,
 each said pocket being selected from the group consisting of:
  a) at least one of an open tong with an open finger or thumb insertion mouth end and an opposite closed distal end or,
  b) an open tong with an open finger or thumb insertion mouth end and an opposite open distal end;
 said set of tongs further having a burstable seal located within an interior of each said pocket, said burstable seal bonding a front and a back wall of said pocket to create a finger stability area within an interior of said pocket, said burstable seal being burstable by insertion of the user's finger(s) or thumb therethrough, to grip and stabilize said finger(s) or thumb within each said respective pocket of said set of tongs, wherein said unburst portion of said burstable seal hugs around the finger(s) or thumb of the user;
 further comprising a peripheral edge of each of said pockets and said connecting tab includes an unbonded free edge beyond a peripheral sealed edge, wherein respective soft, irregular, non-smooth sealed peripheral edges are provided around the edges of the set of tongs, with said soft, injury preventive edges having irregular free ends extending beyond a seal parallel to, and in the vicinity of a periphery of a finger(s)/thumb insertion pocket or strap of a set of tongs, and/or said connecting tab, to promote tearing at the seal to make said soft, irregular, non-smooth sealed peripheral edges, and thereby providing a an injury preventive soft, irregular non-smooth sealed finished peripheral edge to prevent paper cuts on the fingers, thumb or mouth of the user;
 wherein after use, said tearable peripheral edges enable the user to tear the used set of tongs before disposal, enabling the user to place the respective food contact surfaces of both tongs against each other, so that both tongs can be jointly torn into small pieces for environmentally friendly disposal while the user's fingers only contact the clean outer side of the tongs.

28. The triple use finger protecting environmentally and wildlife friendly food handling product as in claim 27 wherein said material is edible.

29. A triple use finger protecting, environmentally and wildlife friendly food handling product made from disposable materials and having a feature to help prevent paper cut injury to the fingers, thumb, mouth, lips and tongue of the user comprising:
 a set of tongs including pair of finger(s)/thumb accommodating pockets with at least one exterior food contact surface on each pocket;
 each said pocket having a respective finger(s) or thumb accommodating interior, said pockets connected by at least one connecting tab,
 at least a portion of at least one tearable seal closing a mouth entrance of said at least one pocket of said pair of finger(s)/thumb accommodating pockets;
 said pocket having a perforation line adjacent to said tearable seal, said perforation line also closing said mouth entrance of said at least one pocket;
 wherein further an inserted finger(s) or thumb of the user pierces said perforation line to open at least a portion of said interior of said at least one pocket, wherein an area around said pierced perforation line at said mouth entrance of said pocket hugs and stabilizes the finger(s)/thumb in one of said pockets with at least one finger(s) accommodating area, wherein said pockets of said set of tongs are pierceable by the finger(s) or thumb at the opening mouth entrance of the pockets of the jaws to pierce at least a portion of the pocket, to reveal at least said portion of the opening of the pocket, whereby the partially open opening hugs around the finger(s) or thumb, or if fully open, fully reveals the pocket interior;

wherein said connecting tab is selected from the group consisting of being stretchable; or having multiple length portions, or is vented, or is provided with at least one additional connecting tab, or is made of two intersecting portions.

* * * * *